United States Patent
Dugan et al.

(10) Patent No.: US 9,550,827 B2
(45) Date of Patent: Jan. 24, 2017

(54) METHODS FOR AMELIORATING AND PREVENTING CENTRAL NERVOUS SYSTEM INFLAMMATION

(75) Inventors: Laura L. Dugan, Brentwood, TN (US); Maria Margarita Behrens, Del Mar, CA (US); Sameh S. Ali, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 128 days.

(21) Appl. No.: 12/681,743

(22) PCT Filed: Oct. 18, 2008

(86) PCT No.: PCT/US2008/080402
§ 371 (c)(1),
(2), (4) Date: Jul. 27, 2010

(87) PCT Pub. No.: WO2009/052454
PCT Pub. Date: Apr. 23, 2009

(65) Prior Publication Data
US 2010/0297070 A1    Nov. 25, 2010

Related U.S. Application Data

(60) Provisional application No. 60/999,587, filed on Oct. 19, 2007.

(51) Int. Cl.
| | | |
|---|---|---|
| *A61K 39/395* | (2006.01) | |
| *C07K 16/24* | (2006.01) | |
| *A61K 31/12* | (2006.01) | |
| *A61K 31/192* | (2006.01) | |
| *C07K 16/28* | (2006.01) | |
| *A61K 39/00* | (2006.01) | |

(52) U.S. Cl.
CPC ............ *C07K 16/248* (2013.01); *A61K 31/12* (2013.01); *A61K 31/192* (2013.01); *C07K 16/2866* (2013.01); *A61K 2039/505* (2013.01)

(58) Field of Classification Search
None
See application file for complete search history.

(56) References Cited

U.S. PATENT DOCUMENTS

| | | |
|---|---|---|
| 7,935,340 B2 * | 5/2011 | Garcia-Martinez et al. .................. 424/133.1 |
| 2003/0045570 A1 | 3/2003 | Posmantur et al. |
| 2005/0095246 A1* | 5/2005 | Shafer ................... 424/145.1 |
| 2006/0135449 A1 | 6/2006 | Sawa et al. |
| 2007/0142272 A1 | 6/2007 | Zlokovic et al. |

FOREIGN PATENT DOCUMENTS

WO    WO/2004/080478    9/2004

OTHER PUBLICATIONS

Nishimoto et al., Arthritis & Rheumatism, 2004, 50(6), pp. 1761-1769.*
Nishimoto et al., Blood, 2000, 95(1), pp. 56-61.*
Ding et al., Reviews on Recent Clinical Trials, 2006, 1(3):193-200.*
Mihara et al., Expert Opin. Biol., 2005, 5(5):683-90.*
Frei et al., J. Neuroimmunology, 1991, 31:147-53.*
Dorothee Mulhausen, Apr. 20, 2010, WIPO, International Preliminary Report on Patentability Chapter I (IB/373) for PCT/US2008/080402.
Patrick Wilson, EPO, May 19, 2010, Rules 161/162 Communication for EPO application EP-08840259.9.
Jung Min Park, KIPO, Jul. 23, 2009, International Search Report for PCT/US2008/080402.
Jung Min Park, KIPO, Apr. 19, 2010, Written Opinion of the International Search Authority for PCT/US2008/080402.
George Varigos, et al., Sep. 23, 2004, WO/2004/080478 publication for PCT/AU2004/000300.
Hill, Response to Rule 161, European Patent Application No. EP08840259.9, European Patent Office, Jun. 28, 2010.
Li, "Transfection with Anti-p65 Intrabody Suppresses Invasion and Angiogenesis in Glioma Cells by Blocking Nuclear Factor-κB Transcriptional Activity,"Clinical Cancer Research, 2007, 13:2178-2190.
Loo et al., "Inhibition of transcription factor NF-κB in the central nervous system ameliorates autoimmune encephalomyelitis in mice," Nature Immunology, vol. 7, No. 9, Sep. 2006, pp. 954-961.
Perez-Mato, Extended European Search Report, European Patent Office, European Patent Application No. 08840259.9, Jul. 11, 2012.
Rafati et al., "Nuclear Factor-κB Decoy Amelioration of Spinal Cord Injury-Induced Inflammation and Behavior Outcomes," Journal of Neuroscience Research, 86:566-580 (2008).
Wang et al., "Co-Stimulation of Cyclic-Amp-Linked Metabotropic Glutamate Receptors in Rat Striatum Attenuates Excitotoxin-Induced Nuclear Factor-κB Activation and Apoptosis," Neuroscience, vol. 94, No. 4, pp. 1153-1162, 1999.
Yi et al., "Role of transcription factors in mediating post-ischemic cerebral inflammation and brain damage," Neurochemistry International, 50 (2007) 1014-1027.
Frei et al., "On the cellular source and function of interleukin 6 produced in the central nervous system in viral diseases", Eur. J. Immunol. 1989 19:689-694.

(Continued)

*Primary Examiner* — Olga N Chernyshev
(74) *Attorney, Agent, or Firm* — Gregory P. Einhorn; Greer Burns & Crain, LLP

(57) ABSTRACT

The invention provides compositions and methods for ameliorating, treating, reversing or preventing pathology or inflammation in the central nervous system (CNS), or the brain, caused or mediated by NFkB, IL-6, IL-6-R, NADPH oxidase (Nox), and/or superoxide and/or hydrogen peroxide production by a NADPH oxidase, including for example ameliorating, treating, reversing or preventing schizophrenia, psychosis, delirium, e.g., post-operative delirium, drug-induced psychosis, psychotic features associated with frailty syndrome (FS), aging, depression, dementias; traumatic war neurosis, post traumatic stress disorder (PTSD) or post-traumatic stress syndrome (PTSS), Amyotrophic Lateral Sclerosis (ALS, or Lou Gehrig's Disease), and/or Multiple Sclerosis (MS). The invention also provides methods for purifying a C60 fullerene, $C_3$ (tris malonic acid C60) or malonic acid derivatives.

20 Claims, 44 Drawing Sheets

(56) References Cited

OTHER PUBLICATIONS

Lieberman et al., "Production of tumor necrosis factor and other cytokines by astrocytes stimulated with lipopolysaccharide or a neurotropic virus", Proc. Natl. Acad, Sci. USA, vol. 86, Aug. 1989, pp. 6348-6352.

Pizzi et al., "Prevention of neuron and oligodendrocyte degeneration by interleukin-6 (IL-6) and IL-6 receptor/IL-6 fusion protein in organotypic hippocampal slices", Mol. Cell. Neurosci. 25 (2004) 301-311.

Qiu et al., "Chronic Interleukin-6 Alters NMDA Receptor-Mediated Membrane Responses and Enhances Neurotoxicity in Developing CNS Neurons", The Journal of Neuroscience, Dec. 15, 1998, 18(24): 10445-10456.

Sparkman et al., "Interleukin-6 Facilitates Lipopolysaccharide-Induced Disruption in Working Memory and Expression of Other Proinflammatory Cytokines in Hippocampal Neuronal Cell Layers", The Journal of Neuroscience, Oct. 18, 2006, 26(42):10709-10716.

Viviani et al., "Interleukin-1B Enhances NMDA Receptor-Mediated Intracellular Calcium Increase Through Activation of the Src Family of Kinases", The Journal of Neuroscience, Sep. 24, 2003, 23(25):8692-8700.

\* cited by examiner

Regis C₃ before cleanup max (485)/min(415) = 2.0

METHODS FOR AMELIORATING AND PREVENTING CENTRAL NERVOUS SYSTEM INFLAMMATION

RELATED APPLICATIONS

This application is a national phase patent utility filing under 35 USC §371, for international application no. PCT/US2008/080402, filed on Oct. 18, 2008, which claims the benefit of priority to United States utility provisional patent application Ser. No. 60/999,587, filed Oct. 19, 2007. The aforementioned applications are explicitly incorporated herein by reference in their entirety and for all purposes.

TECHNICAL FIELD

This invention relates to molecular and cellular biology, biochemistry and medicine. The invention provides compositions and methods for ameliorating or preventing pathologies or inflammation in the central nervous system (CNS), or the brain, caused or mediated by NFkB, interleukin-6 (IL-6), NADPH oxidase ("Nox"), superoxide dismutase (SOD), and/or superoxide and/or hydrogen peroxide production by an NADPH oxidase, including e.g., ameliorating or preventing schizophrenia, psychosis, delirium, drug-induced psychosis, psychotic features associated with these conditions, frailty syndrome (FS), cognitive, learning or memory impairments associated with frailty syndrome (FS), aging, depression and/or dementias; traumatic war neurosis, post traumatic stress disorder (PTSD) and/or post-traumatic stress syndrome (PTSS), and/or Amyotrophic Lateral Sclerosis (ALS, or Lou Gehrig's Disease) and/or Multiple Sclerosis (MS); and cognitive, learning or memory impairments resulting therefrom. The invention also provides methods for purifying a C60 fullerene, $C_3$ (tris malonic acid C60) or a malonic acid derivatives.

BACKGROUND

Schizophrenia, psychosis, delirium, drug-induced psychosis, psychotic features associated with depression and dementia, and dementias are increasingly prevalent and important medical condition. Although the neural circuitry changes that are believed to be responsible for these deficits have been well described in humans, and are reproduced in primate and rodent models of these same disorders, there are currently no therapies directed at the underlying causes of these neural circuitry changes.

Interleukin-6 (IL-6) is known to be elevated in patients with psychosis, schizophrenia, and many dementing disorders. Recently, a therapeutic humanized monoclonal antibody (tocilizumab, or ACTEMRA™ (F. Hoffmann-La Roche Ltd, Basel, Switzerland)) acting as a specific antagonist (is receptor-inhibiting) for IL-6 receptors was approved for the treatment of arthritis.

Frailty syndrome (FS) has become increasingly recognized as a major predictor of co-morbidities and mortality in older individuals. While definitions of FS vary, most experts agree this syndrome is characterized by reduced functional reserve, impaired adaptive responses resulting multi-system decline, which results in increased vulnerability to adverse events.

SUMMARY

The invention provides compositions and methods for preventing or ameliorating an inflammation, pathology or condition in the central nervous system, e.g., the brain, caused or mediated by NFkB, interleukin-6 (IL-6), interleukin-6 (IL-6) receptor (IL-6-R) and/or any member of the NADPH oxidase enzyme family (collectively referred to as "Nox"; e.g., Nox1, Nox2, Nox3, Nox4 or Nox5) or the superoxide dismutase (SOD) enzyme family, and/or superoxide and/or hydrogen peroxide production by a NADPH oxidase, including preventing or ameliorating e.g. schizophrenia, psychosis, delirium, e.g., post-operative delirium, drug-induced psychosis; psychotic features, frailty syndrome (FS), cognitive, learning or memory impairments associated with frailty syndrome (FS), aging, depression and/or dementias (e.g., from Alzheimer's disease, Lewy Body Disease, Parkinson's Disease, Huntington's Disease, Multi-infarct dementia, senile dementia or Frontotemporal Dementia); preventing or ameliorating Amyotrophic Lateral Sclerosis (ALS, or Lou Gehrig's Disease), Multiple Sclerosis (MS), traumatic war neurosis, post traumatic stress disorder (PTSD) or post-traumatic stress syndrome (PTSS), and cognitive, learning or memory impairments resulting therefrom, frailty syndrome (FS), aging, inflammation from CNS infections such as bacterial, yeast or viral infections, e.g., HIV infection (e.g., HIV-1 infection, or AIDS) or meningitis, including *Haemophilus, Cryptococcus, Filobasidiella, Neisseria, Rickettsia* or *Borrelia* infections, and the like. The compositions and methods of this invention can be used to inhibit the activity of or decrease levels of superoxide and/or hydrogen peroxide production by inhibiting or decreasing the activity of NFkB, IL-6, IL-6-R and/or the enzyme NADPH oxidase. In one embodiment, compositions of the invention (e.g., superoxide dismutase (SOD) mimetics) and methods of this invention are used as superoxide dismutase (SOD) mimetics (to mimic the activity of SOD) to decrease levels of superoxide and/or hydrogen peroxide production.

The invention provides methods for ameliorating or preventing schizophrenia, psychosis, delirium, e.g., post-operative delirium, drug-induced psychosis, psychotic features, frailty syndrome (FS), or cognitive, learning or memory impairments resulting from or associated with frailty syndrome (FS), aging, depression, dementias; ameliorating or preventing Amyotrophic Lateral Sclerosis (ALS, or Lou Gehrig's Disease), Multiple Sclerosis (MS), trauma, traumatic war neurosis, post traumatic stress disorder (PTSD), post-traumatic stress syndrome (PTSS), and cognitive, learning or memory impairments resulting therefrom, and inflammation from CNS infections in an individual comprising:

(a) (i) providing a composition that
(1) inhibits or decreases the in vivo activity of NFkB, interleukin-6 (IL-6), interleukin-6 receptor (IL-6-R) or a member of the NADPH oxidase enzyme family (Nox), and/or inhibits or decreases superoxide and/or hydrogen peroxide production by a member of the NADPH oxidase enzyme family, or
(2) acts as a superoxide dismutase mimetic to decrease superoxide and/or hydrogen peroxide; and
(ii) administering an effective amount of the composition of (a) to the individual in need thereof;
(b) the method of (a), wherein the individual is a human;
(c) the method of (a) or (b), wherein the composition comprises a pharmaceutical formulation;
(d) the method of (c), wherein the pharmaceutical formulation is formulated for delivery to the brain or a neural cell, or for passing through the blood brain barrier (BBB);

(e) the method of (d), wherein the pharmaceutical formulation is formulated for delivery to a parvalbumin-positive GABA-ergic interneuron;

(f) the method of any of (a) to (c), wherein the pharmaceutical formulation comprises a therapeutic monoclonal antibody specific for and inhibitory to the activity of NFkB, an IL-6 or IL-6-R and/or an NADPH oxidase enzyme;

(g) the method of (f), wherein the therapeutic monoclonal antibody is a humanized or a human antibody; or (h) the method of (f) or (g), wherein the therapeutic monoclonal antibody against the IL-6-R is tocilizumab, or ACTEMRA™, or the therapeutic monoclonal antibody is against IL-6, or is CNTO-328, a human-mouse chimeric monoclonal antibody (Mab) to IL-6;

(i) the method of (a) or (b), wherein the composition comprises a small molecule;

(j) the method of (i), wherein the small molecule comprises an o-methoxycatechol, an apocynin, a diapocynin, 4-(2-aminoethyl)-benzenesulfonyl fluoride (AEBSF), 4-hydroxy-3'-methoxy-acetophenon, N-Vanillylnonanamide, staurosporine or related compounds;

(k) the method of (a) or (b), wherein the composition comprises an inhibitory nucleic acid molecule to NFkB, IL-6 or NADPH oxidase;

(l) the method of (k), wherein the inhibitory nucleic acid molecule comprises an RNAi molecule, a double-stranded RNA (dsRNA) molecule, an siRNA, a miRNA (microRNA) and/or a short hairpin RNA (shRNA) molecule, or a ribozyme, or a fragment of an NADPH oxidase-encoding nucleic acid;

(m) the method of any of (a) to (l), wherein the member of the NADPH oxidase enzyme family (Nox) is a Nox1, Nox2, Nox3, Nox4 or Nox5 enzyme;

(n) the method of any of (a) to (l), wherein the infection is a viral, bacterial, yeast and/or fungal infection, or a *Haemophilus, Cryptococcus, Filobasidiella, Neisseria, Rickettsia* or *Borrelia* infection;

(o) the method of any of (a) to (n), wherein the composition that inhibits or decreases the in vivo activity of NFkB, interleukin-6 (IL-6) or IL-6R is an antibody against NFkB IL-6 or IL-6-R, respectively;

(p) the method of (o), wherein the composition that inhibits or decreases the in vivo activity of interleukin-6 (IL-6) is interleukin-10 (IL-10);

(q) the method of (p), wherein the composition that inhibits or decreases the in vivo activity of interleukin-6 (IL-6) is ilodecakin or TENOVIL™; or (r) the method of any of (a) to (n), wherein superoxide dismutase mimetic that decreases superoxide and/or hydrogen peroxide comprises a C60 fullerene, $C_3$ (tris malonic acid C60) or a malonic acid derivative.

The invention provides methods for protecting the function of, or maintaining the level of activation or activity of cortical inhibitory neurons, or parvalbumin-positive GABA-ergic interneurons, comprising:

(a) (i) providing a composition that (1) inhibits or decreases the in vivo activity of NFkB, interleukin-6 (IL-6), interleukin-6 receptor (IL-6-R) or a member of the NADPH oxidase enzyme family (Nox), and/or inhibits or decreases superoxide and/or hydrogen peroxide production by a member of the NADPH oxidase enzyme family, or (2) acts as a superoxide dismutase mimetic to decrease superoxide and/or hydrogen peroxide; and (ii) contacting the composition of (a) with the cortical inhibitory neuron or parvalbumin-positive GABA-ergic interneuron;

(b) the method of (a), wherein the contacting is in vivo or in vitro;

(c) the method of (b), wherein the contacting is in vivo and the composition of (a) is administered in an effective amount to an individual in need thereof;

(d) the method of (c), wherein the contacting is in vivo to the CNS, or brain cortex, of the individual;

(e) the method of (c) or (d), wherein the individual is a human;

(f) the method of any of (a) to (e), wherein the composition comprises a pharmaceutical formulation;

(g) the method of (f), wherein the pharmaceutical formulation is formulated for delivery to the brain or a neural cell, or for passing through the blood brain barrier (BBB);

(h) the method of (f) or (g), wherein the pharmaceutical formulation is formulated for delivery to a cortical inhibitory neuron or a parvalbumin-positive GABA-ergic interneuron;

(i) the method of any of (a) to (h), wherein the composition or the pharmaceutical formulation comprises a therapeutic monoclonal antibody specific for and inhibitory to the activity of NFkB, an IL-6 or IL-6-R or an NADPH oxidase enzyme;

(j) the method of (i), wherein the therapeutic monoclonal antibody is a humanized or a human antibody; or (k) the method of (i) or (j), wherein the therapeutic monoclonal antibody against the IL-6-R is tocilizumab, or ACTEMRA™, or the therapeutic monoclonal antibody is against IL-6, or is CNTO-328, a human-mouse chimeric monoclonal antibody (Mab) to IL-6;

(l) the method of any of (a) to (h), wherein the composition or the pharmaceutical formulation comprises a small molecule;

(m) the method of (l), wherein the small molecule comprises an o-methoxycatechol, an apocynin, a diapocynin, 4-(2-aminoethyl)-benzenesulfonyl fluoride (AEBSF), 4-hydroxy-3'-methoxy-acetophenon, N-Vanillylnonanamide, staurosporine or related compounds;

(n) the method of any of (a) to (h), wherein the composition or the pharmaceutical formulation comprises an inhibitory nucleic acid molecule to NFkB, IL-6, IL-6-R, or NADPH oxidase; or (o) the method of (n), wherein the inhibitory nucleic acid molecule comprises an RNAi molecule, a double-stranded RNA (dsRNA) molecule, an siRNA, a miRNA (microRNA) and/or a short hairpin RNA (shRNA) molecule, or a ribozyme, or a fragment of an NADPH oxidase-encoding nucleic acid; or (p) the method of any of (a) to (o), wherein the member of the NADPH oxidase enzyme family (Nox) is a Nox1, Nox2, Nox3, Nox4 or Nox5 enzyme;

(q) the method of any of (a) to (p), wherein the composition that inhibits or decreases the in vivo activity of NFkB, IL-6, IL-6-R, or NADPH oxidase is an antibody against NFkB, IL-6, IL-6-R, or NADPH oxidase, respectively;

(r) the method of (q), wherein the composition that inhibits or decreases the in vivo activity of interleukin-6 (IL-6) is IL-10;

(s) the method of (r), wherein the composition that inhibits or decreases the in vivo activity of interleukin-6 (IL-6) is ilodecakin or TENOVIL™; or (t) the method of any of (a) to (h), wherein superoxide dismutase mimetic that decreases superoxide and/or hydrogen peroxide comprises a C60 fullerene, $C_3$ (tris malonic acid C60) or a malonic acid derivative.

The invention provides kits comprising (a) a composition that inhibits NFkB, interleukin-6 (IL-6), interleukin-6 receptor, a member of the NADPH oxidase enzyme family (Nox), and/or superoxide or hydrogen peroxide production by a member of the NADPH oxidase enzyme family (Nox), or a composition that acts as a superoxide dismutase mimetic to decrease superoxide and/or hydrogen peroxide;

(b) the kit of (a) further comprising instructions comprising use of the method of claim 1 or claim 2;

(c) the kit of any of (a) or (b), wherein the member of the NADPH oxidase enzyme family (Nox) is a Nox1, Nox2, Nox3, Nox4 or Nox5 enzyme;

(d) the kit of any of (a) to (c), wherein the composition that inhibits NFkB, interleukin-6 (IL-6), interleukin-6 receptor, a member of the NADPH oxidase enzyme family (Nox), and/or superoxide and/or hydrogen peroxide production by a member of the NADPH oxidase enzyme family (Nox) comprises an antisense nucleic acid, an siRNA, a miRNA or a ribozyme that binds to hybridization to and inhibits or decreases the activity or expression of an antibody the specifically binds to the NFkB, interleukin-6 (IL-6), interleukin-6 receptor, or the member of the NADPH oxidase enzyme family (Nox); or (e) the kit of any of (a) to (c), wherein the composition that inhibits the NFkB, interleukin-6 (IL-6), interleukin-6 receptor, or the member of the NADPH oxidase enzyme family (Nox), and/or superoxide and/or hydrogen peroxide production by a member of the NADPH oxidase enzyme family (Nox) comprises an antibody that specifically binds to the NFkB, interleukin-6 (IL-6), interleukin-6 receptor, or the member of the NADPH oxidase enzyme family (Nox), respectively;

(f) the kit of any of (a) to (e), wherein the composition that inhibits or decreases the in vivo activity of interleukin-6 (IL-6) is an antibody against IL-6;

(g) the kit of (f), wherein the composition that inhibits or decreases the in vivo activity of interleukin-6 (IL-6) is IL-10;

(h) the kit of (g), wherein the composition that inhibits or decreases the in vivo activity of interleukin-6 (IL-6) is ilodecakin or TENOVIL™; or (i) the kit of (a), wherein superoxide dismutase mimetic that decreases superoxide and/or hydrogen peroxide comprises a C60 fullerene, $C_3$ (tris malonic acid C60) or a malonic acid derivative.

The invention provides uses of a composition that inhibits or decreases the level of activation or activity of NFkB, interleukin-6 (IL-6), interleukin-6 receptor (IL-6-R) or a member of the NADPH oxidase enzyme family (Nox), and/or superoxide or hydrogen peroxide production by a member of the NADPH oxidase enzyme family (Nox), for the manufacture of a pharmaceutical for protecting the function of, or maintaining the level of activation or activity of, a parvalbumin-positive GABA-ergic interneuron in the cortex of an individual. In one embodiment of the use: (a) the member of the NADPH oxidase enzyme family (Nox) is a Nox1, Nox2, Nox3, Nox4 or Nox5 enzyme; (b) the composition that inhibits NFkB, interleukin-6 (IL-6), interleukin-6 receptor (IL-6-R) or a member of the NADPH oxidase enzyme family (Nox), comprises an antisense nucleic acid, an siRNA, a miRNA or a ribozyme that binds to or hybridizes to and inhibits or decreases the activity or expression of a nucleic acid encoding NFkB, interleukin-6 (IL-6), interleukin-6 receptor (IL-6-R) or a member of the NADPH oxidase enzyme family (Nox). In one embodiment of the use, the composition that inhibits NFkB, interleukin-6 (IL-6), interleukin-6 receptor (IL-6-R) or a member of the NADPH oxidase enzyme family (Nox) is an antibody the specifically binds to the NFkB, IL-6, IL-6-R or the member of the NADPH oxidase enzyme family (Nox).

The invention provides uses of a composition that acts as a superoxide dismutase mimetic to decrease superoxide and/or hydrogen peroxide, wherein in one embodiment the superoxide dismutase mimetic that decreases superoxide and/or hydrogen peroxide comprises a C60 fullerene, $C_3$ (tris malonic acid C60) or a malonic acid derivative.

The invention provides uses of a composition that inhibits or decreases the level of activation or activity of NFkB, IL-6, IL-6-R, NADPH oxidase, and/or decreases the level of superoxide or hydrogen peroxide production by a member of the NADPH oxidase enzyme family (Nox), and provides uses of a composition that acts as a superoxide dismutase mimetic to decrease superoxide and/or hydrogen peroxide, wherein in one embodiment the superoxide dismutase mimetic that decreases superoxide and/or hydrogen peroxide comprises a C60 fullerene, $C_3$ (tris malonic acid C60) or a malonic acid derivative, for the manufacture of a pharmaceutical for: (a) ameliorating (treating, slowing the progress of or reversing) or preventing schizophrenia, psychosis, delirium, e.g., post-operative delirium, drug-induced psychosis, psychotic features, frailty syndrome (FS), or cognitive, learning or memory impairments resulting from or associated with frailty syndrome (FS), aging, depression, dementias; ameliorating or preventing traumatic war neurosis, post traumatic stress disorder (PTSD) or post-traumatic stress syndrome (PTSS), Amyotrophic Lateral Sclerosis (ALS, or Lou Gehrig's Disease), and/or Multiple Sclerosis (MS), and cognitive, learning or memory impairments resulting therefrom, and frailty syndrome (FS) and aging, and the CNS inflammation of traumas and inflammation from CNS infections; (b) ameliorating (treating, slowing the progress of or reversing) or preventing Alzheimer's disease, Lewy Body Disease, Parkinson's Disease, Huntington's Disease, Multi-infarct dementia (vascular dementia), senile dementia or Frontotemporal Dementia (Pick's Disease), Amyotrophic Lateral Sclerosis (ALS, or Lou Gehrig's Disease), and/or Multiple Sclerosis (MS), and cognitive, learning or memory impairments resulting therefrom, and frailty syndrome (FS) and aging (c) increasing resistance to a CNS neurological pathology, trauma, disease, inflammation from CNS infection; and/or condition caused by and/or associated with an increased amount of inflammation and/or oxidative stress in the CNS, or, ameliorating (treating, slowing the progress of or reversing) or preventing a CNS inflammation caused by a CNS infection or trauma, and cognitive, learning or memory impairments resulting therefrom; (d) ameliorating (treating, slowing the progress of or reversing) or preventing a CNS inflammation and/or injury in a concussive or traumatic injury and cognitive, learning or memory impairments resulting therefrom, and/or in an individual with post-concussion syndrome (also known as postconcussive syndrome or PCS) and cognitive, learning or memory impairments resulting therefrom, in an individual.

In one embodiment of the use: (a) the member of the NADPH oxidase enzyme family (Nox) is a Nox1, Nox2, Nox3, Nox4 or Nox5 enzyme; (b) the composition that inhibits NFkB, IL-6, IL-6-R, a member of the NADPH oxidase enzyme family (Nox), and/or superoxide and/or hydrogen peroxide production by a member of the NADPH oxidase enzyme family (Nox) comprises an antisense nucleic acid, an siRNA, a miRNA or a ribozyme that binds to or hybridizes to and inhibits or decreases the activity or expression of a nucleic acid encoding NFkB, IL-6, IL-6-R or a member of the NADPH oxidase enzyme family (Nox); (c) the composition that inhibits IL-6, IL-6-R, a member of the NADPH oxidase enzyme family (Nox), and/or superoxide and/or hydrogen peroxide production by a member of the NADPH oxidase enzyme family (Nox) comprises an antibody the specifically binds to NFkB, IL-6, IL-6-R or the member of the NADPH oxidase enzyme family (Nox); or (d) the infection ameliorated is a bacterial infection, a viral infection, a yeast or fungal infection, or the infection ameliorated is an HIV infection, or wherein the infection is a *Haemophilus, Cryptococcus, Filobasidiella, Neisseria, Rickettsia* or *Borrelia* infection.

The invention provides methods for ameliorating (slowing, reversing or abating) or preventing neuron or CNS or brain damage in individuals having frailty syndrome (FS), aging, injuries, pathologies, diseases, infections and conditions causing and/or associated with an increased amount of CNS inflammation and/or CNS oxidative stress, or accelerating the recovery of CNS neuron or brain damage in individuals having injuries, pathologies (e.g., Amyotrophic Lateral Sclerosis (ALS, or Lou Gehrig's Disease), and/or Multiple Sclerosis (MS)), and cognitive, learning or memory impairments resulting therefrom, diseases, infections and conditions causing and/or associated with an increased amount of CNS inflammation and/or CNS oxidative stress, and cognitive, learning or memory impairments resulting therefrom, comprising:

(a) (i) providing a composition that inhibits or decreases the level of activation or activity of NFkB, IL-6, IL-6-R, a member of the NADPH oxidase enzyme family (Nox), and/or inhibits or decreases superoxide or hydrogen peroxide production by a member of the NADPH oxidase enzyme family (Nox), or providing a composition that acts as a superoxide dismutase mimetic to decrease superoxide and/or hydrogen peroxide; and (ii) contacting or administering a therapeutically effective amount of the composition of (a) with an individual in need thereof;

(b) the method of (a), wherein the individual in need thereof is a human;

(c) the method of (a) or (b), wherein the composition of (a) is formulated as a pharmaceutical composition;

(d) the method of any of (a) to (c), wherein the contacting or administering is into the CNS, or brain cortex, of the individual;

(e) the method of any of (a) to (d), wherein the individual is a human;

(f) the method of any of (a) to (e), wherein the human has Alzheimer's disease, Lewy Body Disease, Parkinson's Disease, Huntington's Disease, Multi-infarct dementia (vascular dementia), senile dementia or Frontotemporal Dementia (Pick's Disease), Amyotrophic Lateral Sclerosis (ALS, or Lou Gehrig's Disease), and/or Multiple Sclerosis (MS) or cognitive, learning or memory impairments resulting therefrom;

(g) the method of any of (a) to (f), wherein the composition or pharmaceutical formulation is formulated for delivery to the CNS, or brain or a CNS neural cell, or for passing through the blood brain barrier (BBB);

(h) the method of any of (a) to (g), wherein the composition or pharmaceutical formulation is formulated for delivery to a parvalbumin-positive GABA-ergic interneuron;

(i) the method of any of (a) to (h), wherein the composition or the pharmaceutical formulation comprises a therapeutic monoclonal antibody specific for and inhibitory to the activity of an NFkB, IL-6 or IL-6-R or an NADPH oxidase (Nox) enzyme;

(j) the method of (i), wherein the therapeutic monoclonal antibody is a humanized or a human antibody; or (k) the method of (i) or (j), wherein the therapeutic monoclonal antibody against the IL-6-R is tocilizumab, or ACTEMRA™, or the therapeutic monoclonal antibody is against IL-6, or is CNTO-328, a human-mouse chimeric monoclonal antibody (Mab) to IL-6;

(l) the method of any of (a) to (h), wherein the composition or the pharmaceutical formulation comprises a small molecule;

(m) the method of (l), wherein the small molecule comprises an o-methoxycatechol, an apocynin, a diapocynin, 4-(2-aminoethyl)-benzenesulfonyl fluoride (AEBSF), 4-hydroxy-3'-methoxy-acetophenon, N-Vanillylnonanamide, staurosporine or related compounds;

(n) the method of any of (a) to (h), wherein the composition or the pharmaceutical formulation comprises an inhibitory nucleic acid molecule to the expression of NFkB, IL-6, IL-6-R or NADPH oxidase; or (o) the method of (n), wherein the inhibitory nucleic acid molecule comprises an RNAi molecule, a double-stranded RNA (dsRNA) molecule, an siRNA, a miRNA (microRNA) and/or a short hairpin RNA (shRNA) molecule, or a ribozyme, or an inhibitory fragment of an NFkB-, IL-6-, IL-6-R- or NADPH oxidase-encoding nucleic acid;

(p) the method of any of (a) to (o), wherein the member of the NADPH oxidase enzyme family (Nox) is a Nox1, Nox2, Nox3, Nox4 or Nox5 enzyme;

(q) the method of any of (a) to (p), wherein the injury is a concussive or traumatic injury, and/or injury is post-concussion syndrome (also known as postconcussive syndrome or PCS), or cognitive, learning or memory impairments resulting therefrom; or (r) the method of any of (a) to (p), wherein the infection is a bacterial, viral or yeast infection, or the infection is an HIV infection;

(s) the method of any of (a) to (r), wherein the composition that inhibits or decreases the in vivo activity of interleukin-6 (IL-6) is an antibody against IL-6;

(t) the method of (s), wherein the composition that inhibits or decreases the in vivo activity of interleukin-6 (IL-6) is IL-10;

(u) the method of (t), wherein the composition that inhibits or decreases the in vivo activity of interleukin-6 (IL-6) is ilodecakin or TENOVIL™; or (v) wherein superoxide dismutase mimetic that decreases superoxide and/or hydrogen peroxide comprises a C60 fullerene, $C_3$ (tris malonic acid C60) or a malonic acid derivative.

The invention provides methods for increasing resistance to or recovery from a CNS injury, a neurological pathology, a disease, an infection and/or a condition caused by and/or associated with an increased amount of inflammation and/or oxidative stress in the CNS or brain, or cognitive, learning or memory impairments resulting therefrom, comprising:

(a) (i) providing a composition that inhibits or decreases the level of activation or activity of NFkB, IL-6, IL-6-R, a member of the NADPH oxidase enzyme family (Nox), and/or inhibits or decreases superoxide or hydrogen peroxide production by a member of the NADPH oxidase enzyme family (Nox), or providing a composition that acts as a superoxide dismutase mimetic to decrease superoxide and/or hydrogen peroxide; and (ii) contacting or administering a therapeutically effective amount of the composition of (a) with an individual in need thereof; and (ii) contacting or administering a therapeutically effective amount of the composition of (a) with an individual in need thereof;

(b) the method of (a), wherein the individual in need thereof is a human;

(c) the method of (a) or (b), wherein the composition of (a) is formulated as a pharmaceutical composition;

(d) the method of any of (a) to (c), wherein the contacting or administering is into the CNS or brain cortex of the individual;

(e) the method of any of (a) to (d), wherein the individual is a human;

(f) the method of any of (a) to (e), wherein the human has Alzheimer's disease, Lewy Body Disease, Parkinson's Disease, Huntington's Disease, Multi-infarct dementia (vascular dementia), senile dementia or Frontotemporal Dementia (Pick's Disease), Amyotrophic Lateral Sclerosis (ALS, or Lou Gehrig's Disease), and/or Multiple Sclerosis (MS), or cognitive, learning or memory impairments resulting therefrom;

(g) the method of any of (a) to (f), wherein the composition or pharmaceutical formulation is formulated for delivery to the CNS or brain or a neural cell, or for passing through the blood brain barrier (BBB);

(h) the method of any of (a) to (g), wherein the composition or pharmaceutical formulation is formulated for delivery to a parvalbumin-positive GABA-ergic interneuron;

(i) the method of any of (a) to (h), wherein the composition or the pharmaceutical formulation comprises a therapeutic monoclonal antibody specific for and inhibitory to the activity of an NFkB, IL-6 or IL-6-R or an NADPH oxidase (Nox) enzyme;

(j) the method of (i), wherein the therapeutic monoclonal antibody is a humanized or a human antibody; or (k) the method of (i) or (j), wherein the therapeutic monoclonal antibody against the IL-6-R is tocilizumab, or ACTEMRA™, or the therapeutic monoclonal antibody is against IL-6, or is CNTO-328, a human-mouse chimeric monoclonal antibody (Mab) to IL-6;

(l) the method of any of (a) to (h), wherein the composition or the pharmaceutical formulation comprises a small molecule;

(m) the method of (l), wherein the small molecule comprises an o-methoxycatechol, an apocynin, a diapocynin, 4-(2-aminoethyl)-benzenesulfonyl fluoride (AEBSF), 4-hydroxy-3'-methoxy-acetophenon, N-Vanillylnonanamide, staurosporine or related compounds;

(n) the method of any of (a) to (h), wherein the composition or the pharmaceutical formulation comprises an inhibitory nucleic acid molecule to a nucleic acid encoding an NFkB, IL-6, IL-6-R or NADPH oxidase; or (o) the method of (n), wherein the inhibitory nucleic acid molecule comprises an RNAi molecule, a double-stranded RNA (dsRNA) molecule, an siRNA, an miRNA (microRNA) and/or a short hairpin RNA (shRNA) molecule, or a ribozyme, or an inhibitory fragment of an NFkB-, IL-6-, IL-6-R- or NADPH oxidase-encoding nucleic acid sequence;

(p) the method of any of (a) to (o), wherein the member of the NADPH oxidase enzyme family (Nox) is a Nox1, Nox2, Nox3, Nox4 or Nox5 enzyme; or (q) the method of any of (a) to (p), wherein the method increases resistance to a concussive or traumatic injury, and/or the method increases resistance to or ameliorate the effects of post-concussion syndrome (also known as post-concussive syndrome or PCS), or cognitive, learning or memory impairments resulting therefrom;

(r) the method of any of (a) to (q), wherein the composition that inhibits or decreases the in vivo activity of interleukin-6 (IL-6) is an antibody against IL-6;

(s) the method of (r), wherein the composition that inhibits or decreases the in vivo activity of interleukin-6 (IL-6) is IL-10;

(t) the method of (s), wherein the composition that inhibits or decreases the in vivo activity of interleukin-6 (IL-6) is ilodecakin or TENOVIL™; or (u) the method of (s), wherein the superoxide dismutase mimetic that decreases superoxide and/or hydrogen peroxide comprises a C60 fullerene, $C_3$ (tris malonic acid C60) or a malonic acid derivative.

The invention provides methods for purifying C60 fullerene derivatives, including $C_3$ (tris malonic acid C60) and other malonic acid derivatives comprising (i) (a) dissolving an impure powder form of $C_3$ (tris malonic acid C60 fullerene) or other malonic acid derivatives in dilute sodium hydroxide (NaOH) solution at a concentration of between about 1 mM to 400 mM at about 4 degrees C. with stirring;

(b) adding a second solution of NaOH more concentrated than the dilute NaOH solution in step (a) drop-wise to the solution of step (a) to achieve an approximately neutral pH;

(c) incubating the solution of step (b) at 4 degrees C. in the dark for approximately 0.5 to 3 hours;

(d) centrifuging the solution after the incubating of step (c) to produce a clear dark red supernatant and a solid light pink pellet;

(e) removing the supernatant to a different container;

(f) incubating the supernatant removed in step (e) at 4 degrees C. for an additional about 3 to 4 hours; and (g) (1) re-centrifuging to remove substantially all or all undissolved material to generate a pellet and a solution comprising purified $C_3$, wherein the pellet comprises an insoluble waxy material containing contaminant and small amounts of residual $C_3$, or (2) filtering the sample through a filter which allows only aqueous solutions to pass, thereby removing an insoluble waxy contaminant after solubilization in dilute NaOH, thereby generating a solution comprising purified $C_3$; or (ii) the method of (i), wherein the purified $C_3$ solution is further treated to remove a minor amount of volatile contaminant by vacuum distillation or by bubbling an inert gas through the solution.

The invention provides methods for purifying a C60 fullerene derivative, $C_3$ (tris malonic acid C60) or other malonic acid derivatives comprising (a) providing a solution comprising an impure powder form of $C_3$ (tris malonic acid C60) or other malonic acid derivative; and (b) providing an antibody directed against the C60 fullerene derivative, $C_3$ (tris malonic acid C60) or other malonic acid derivative; and (c) isolating the C60 fullerene derivative, $C_3$ (tris malonic acid C60) or other malonic acid derivative by incubating the antibody with the C60 fullerene derivative, $C_3$ (tris malonic acid C60) or other malonic acid derivative under conditions wherein the antibody specifically binds to the C60 fullerene, to $C_3$ (tris malonic acid C60) or to another malonic acid derivative; or (ii) the method of (i), wherein an antibody-C60 fullerene, antibody-$C_3$ (tris malonic acid C60) or antibody-malonic acid derivative complex is purified by gel electrophoresis purification, HPLC, immunoprecipitation, column chromatography, differential centrifugation or affinity column chromatography.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

DESCRIPTION OF DRAWINGS

FIG. 1A, FIG. 1B, and FIG. 1C: Confocal images of representative fields depicting a parvalbumin-positive (PV)-interneuron and surrounding neurons treated in the absence of ketamine (control) (FIG. 1A), the presence of ketamine (FIG. 1B), and co-exposure to ketamine and muscimol (FIG. 1C); FIG. 1D and FIG. 1E: graphic illustration of quantification results for DHE (FIG. 1D), and PV (FIG. 1E) fluorescence; as discussed in detail in Example 1, below.

FIG. 3A illustrates both membrane fractions as analyzed for the expression of the indicated proteins (Nox2, Nox4, $p22^{phox}$, and Actin) by image of Western blots (insert to FIG. 3A), and FIG. 3A bar graph graphically represent the quantification of Western blot data normalized for actin content; FIG. 3B bar graph illustrates data showing increased Nox activity was observed in synaptosomal preparations from ketamine treated animals; as discussed in detail in Example 1, below.

FIG. 4A: confocal images showing parvalbumin and GAD67 expression in PV-interneurons (upper panels are saline controls, with lower panels the ketamine treated samples); FIG. 4B: animals were treated with apocynin in the drinking water for 1 week, or during one month with the SOD-mimetic $C_3$ delivered by mini-pumps before ketamine treatment; as discussed in detail in Example 1, below, as discussed in detail in Example 1, below.

FIG. 5B: graph bar represents the quantification of mean fluorescence/cell as a percent of control, where the "+musci" indicates "+muscimol"; as discussed in detail in Example 1, below.

FIG. 6A illustrates confocal images showing the increase in Nox2 immunoreactivity after 24 h of treatment with ketamine in primary cultured neurons (upper three panels control, lower three panels ketamine treated) with MAP-2 immunoreactivity used as a marker for neurons; FIG. 6B: inset shows image of Western blots prepared form cultures treated as in FIG. 6A, showing increase in Nox2 protein level, with bar graph schematically illustrating-summarizing the data from this study; as discussed in detail in Example 1, below.

FIG. 7A: graphically summarizes data showing oxygen consumption by synaptosomal Nox(s) from cortex of saline or ketamine injected mice was induced by the addition of 5 mM NADPH to samples containing synaptosomal protein; the inset in FIG. 7A graphically illustrates data showing the apocynin dependent inhibition of Nox activity; FIG. 7B graphically summarizes data showing ketamine treatment did not affect synaptosomal mitochondria; respiratory function of synaptosomal mitochondria in the same preparations was then evaluated by the subsequent addition of $NAD^+$-linked substrates followed by the addition of the $F_0F_1$-ATPase inhibitor oligomycin to attain State 4 respiration, and the maximal mitochondria respiration was initiated by the addition of the protonophore uncoupling agent, CCCP, as illustrated in FIG. 7B; as discussed in detail in Example 1, below.

FIG. 27A, four panels illustrating confocal images of cells showing that increasing concentrations of anti-mIL-6 prevented the decrease in parvalbumin (PV) and GAD67 after 24 h of ketamine exposure. Bottom bar graph shows the fluorescence quantification of both antigens in PV-interneurons expressed as % of control; FIG. 27B: four panels illustrating confocal images showing that increasing concentrations of anti-mIL-6 prevented the increase in oxidized DHE cause by ketamine exposure. Bottom bar graph shows results for fluorescence quantification of oxidized DHE expressed as % of control, as described in detail in Example 2, below.

FIG. 28 upper six panels illustrate confocal images of cells showing that increasing concentrations of anti-mIL-6 prevented the decrease in parvalbumin (PV) and GAD67 after 24 h of ketamine exposure; and the bar graph shows results for fluorescence quantification of both antigens in PV-interneurons expressed as % of control, as described in detail in Example 2, below.

30A: EPR assessment of superoxide production in live cultures upon treatment with ketamine; primary cultures were exposed to ketamine for the times indicated in the absence or presence of an anti-mouse IL-6 blocking antibody produced in rat, at the indicated times, the coverslips were transferred to a quartz chamber and superoxide production was followed by EPR spectroscopy using the spin-trap DIPPMPO; FIG. 30B: IL-6 increased basal NADPH oxidase activity in forebrain synaptosomes isolated from 3 month-old mouse forebrains accumulation of superoxide during the first 6 min was analyzed using the spin trap DEPMPO, as described in detail in Example 2, below.

FIG. 31A illustrates four panels of gels of mRNAs for Nox1, Nox2, Nox3, Nox4, Nox5 and p22$^{phox}$ as indicated, showing levels were increased in several brain regions of aged mice; FIG. 31B: Western blot analysis of young and old forebrain proteins demonstrated an increase in Nox2, Nox4 and p22 protein content, with this data also graphically illustrated; FIG. 31C: Western blot analysis showing the specificity of the antibodies used for Nox2 was confirmed in wild type and gp91phox−/− forebrain extracts, as described in detail in Example 3, below.

FIG. 33C illustrates Nox specific activity on young and old animals; FIG. 33D illustrates mitochondrial specific activity; as described in detail in Example 3, below.

FIG. 34A illustrates six confocal image panels showing that the phosphorylation of the protein kinase Jak2 increased; FIG. 34B illustrates nine confocal image panels showing that prolonged exposure to the interleukin increased production of superoxide and increased the expression of Nox2 in neurons; the role of Nox2 activation in the increase in DHE oxidation was confirmed by co-exposure to the Nox inhibitor apocynin (FIG. 34B bottom panels), as described in detail in Example 3, below.

FIG. 35A illustrates a gel RNA image of Nox2 mRNA detected by RT-PCR from four month old mice treated with either saline (left image) or with IL-6(right image), and brains were either processed for RNA or for synaptosomal preparation; FIG. 35 B upper image illustrates immunoblots of Nox2 and p22 (and control actin) synaptosomal proteins in samples with and without IL-6 treatment separated on 10% SDS-PAGE gels, and FIG. 35 B lower image graphically summarizes the data from the immunoblots; FIG. 35 C graphically illustrates Nox activity in synaptosomes with or without apocynin, as indicated; as described in detail in Example 3, below.

FIG. 42A: effect of ketamine on the average mean intensity per cell for each CBP in the PFC region; FIG. 42B: analysis of the mean intensity per cell for GAD67 content analyzed in each CBP stained cell; FIG. 42C: confocal images obtained with a 40× objective depicting the effects of ketamine on the immuno-fluorescence for PV and GAD67 in the PFC region of young and old animals, as described in detail in Example 4, below.

FIG. 43 left image graphically illustrates data showing that there is enhanced vulnerability of the remaining neurons to loss-of-phenotype (and loss of inhibitory function) in old mice (as compared to young mice) in response to even sub-anesthetic doses of an anesthetic; aging also increases the sensitivity of old mice (as compared to young mice) to ketamine at 20, 30 and 40 mg/kg, as graphically illustrated in FIG. 43 right image, as described in detail in Example 4, below.

Like reference symbols in the various drawings indicate like elements.

DETAILED DESCRIPTION

Figure 1:
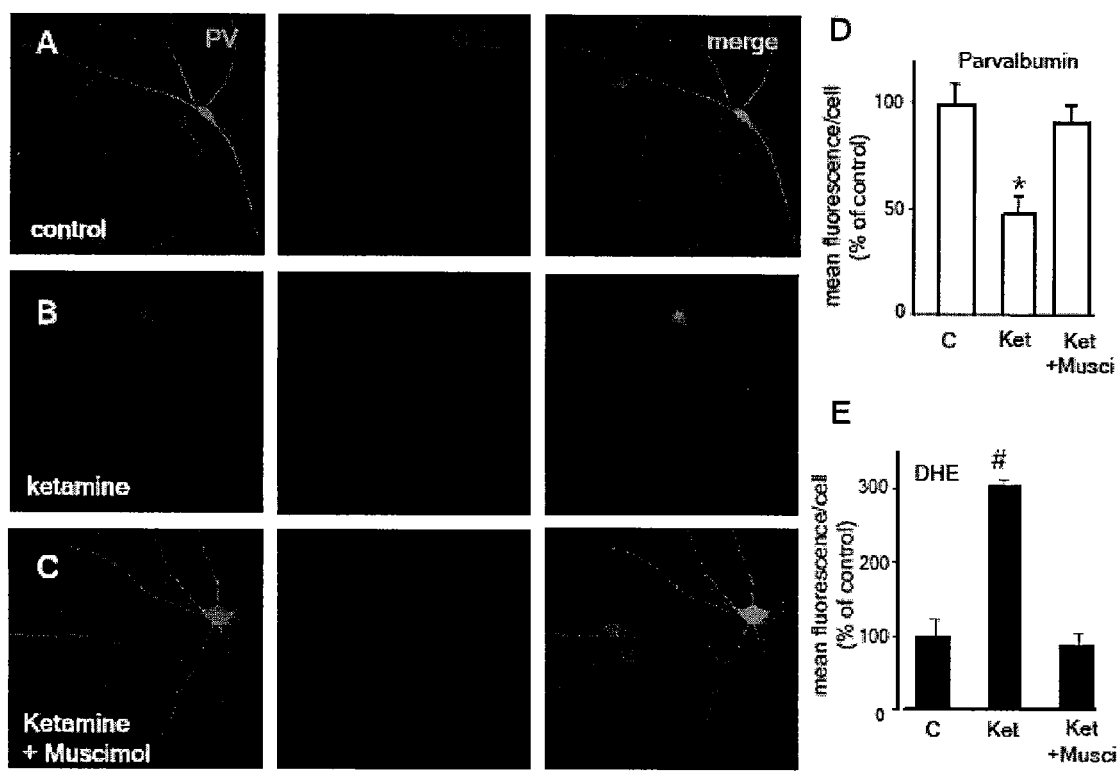
FIG. 1 illustrates experimental results showing that ketamine exposure in primary neuronal cultures increases superoxide and/or hydrogen peroxide production and induces the loss of parvalbumin immunoreactivity, as described in detail in Example 1, below.

The invention provides compositions and methods for the amelioration or prevention, including the treatment of, a CNS inflammation, psychosis, delirium, schizophrenia, depression and/or dementias, traumatic war neurosis, post traumatic stress disorder (PTSD) or post-traumatic stress syndrome (PTSS), and cognitive, learning or memory impairments resulting therefrom, in an individual, e.g., in humans. The invention provides compositions and methods for the amelioration or prevention of diseases or conditions caused by diminished activity of parvalbumin-positive GABA-ergic interneurons in the cortex and which are caused by activation of signaling mechanisms that induce and activate any member of the NADPH oxidase family (Nox). The invention provides compositions and methods to inhibit or decrease (amount or rate of) activation of any member of the NADPH oxidase family (Nox), and/or block or inhibit NFkB and/or interleukin-6 (IL-6)-mediated NADPH oxidase (Nox) activation and induction, thus ameliorating or preventing or treating a CNS inflammation, psychosis, delirium, schizophrenia, depression and/or dementias, traumatic war neurosis, post traumatic stress disorder (PTSD) or post-traumatic stress syndrome (PTSS), Amyotrophic Lateral Sclerosis (ALS, or Lou Gehrig's Disease), and/or Multiple Sclerosis (MS), and cognitive, learning or memory impairments resulting therefrom, and frailty syndrome (FS) and aging. In one embodiment, blocking or inhibiting NFkB or interleukin-6 (IL-6)-mediated NADPH oxidase (Nox) activation and induction comprises blocking or inhibiting interleukin-6-R (IL-6-R) activation by IL-6, which can comprise blocking or inhibiting interleukin-6-R (IL-6-R) binding with an IL-6-R activation ligand, e.g., the IL-6-R ligand IL-6. In one embodiment, the invention provides for administering a superoxide dismutase (SOD) mimetic such as a malonic acid derivative, e.g., the fullerene C60, or the carboxyfullerene-based SOD-mimetic $C_3$ to decrease superoxide levels in a cell of the CNS.

The inventors have discovered and demonstrated that specific inflammatory pathways are involved in alterations in the CNS, e.g., the brain, that are known to be associated with a CNS inflammation, psychosis, delirium, schizophrenia, depression and/or dementias, traumatic war neurosis, post traumatic stress disorder (PTSD) or post-traumatic stress syndrome (PTSS), Amyotrophic Lateral Sclerosis (ALS, or Lou Gehrig's Disease), and Multiple Sclerosis (MS), and cognitive, learning or memory impairments resulting therefrom, in humans. These alterations include dysfunction of a critical set of neurons—the parvalbumin-positive GABA-ergic interneurons—in the cortex of the brain. Using a well-established mouse model of schizophrenia/psychosis the inventors specifically demonstrated that NADPH oxidase, an inflammatory enzyme complex, is induced and activated in neurons in brain in this mouse model. The inventors then demonstrated that NADPH oxidase (Nox) is responsible for dysfunction of the parvalbumin-positive interneurons, and that inhibiting NADPH oxidase rescues these same neurons. The inventors also show that eliminating superoxide/hydrogen peroxide produced by NADPH oxidase or other sources rescues these same neurons; thus, in one embodiment the invention provides compositions and methods for rescuing parvalbumin-positive interneurons by e.g., inhibiting or decreasing the activity of any member of the NADPH oxidase either directly or indirectly, e.g., by directly or indirectly inhibiting or decreasing the activity of IL-6 and/or IL-6-R. The inventors demonstrated that interleukin-6 (IL-6) is responsible for the induction and activation of NADPH oxidase in this model. Finally, the inventors demonstrated that administration of composition that acts as a superoxide dismutase mimetic to decrease superoxide and/or hydrogen peroxide has a cytoprotective effect in the CNS. See e.g. Examples 1 through 3, below.

Thus, the invention provides compositions and methods to decrease NFkB, IL-6 and/or Nox enzyme levels and/or activity, or to decrease superoxide and/or hydrogen peroxide levels in the CNS, to treat patients with psychosis, schizophrenia, and many dementing disorders, CNS inflammation, delirium, depression, traumatic war neurosis, post traumatic stress disorder (PTSD) or post-traumatic stress syndrome (PTSS), Amyotrophic Lateral Sclerosis (ALS, or Lou Gehrig's Disease), and/or Multiple Sclerosis (MS), and cognitive, learning or memory impairments resulting therefrom. The invention provides compositions and methods using a therapeutic monoclonal antibody against IL-6 receptors, e.g., tocilizumab (ACTEMRA™), or the therapeutic monoclonal antibody is against IL-6, e.g., is CNTO-328, a human-mouse chimeric monoclonal antibody (Mab) to IL-6 (Centocor, Inc., Horsham, Pa.). Thus, the invention provides compositions and methods to inhibit any member of the NADPH oxidase enzyme family and/or IL-6 because they are therapeutic targets in psychosis, schizophrenia, dementias, CNS inflammation, delirium, depression, traumatic war neurosis, post traumatic stress disorder (PTSD) or post-traumatic stress syndrome (PTSS), Amyotrophic Lateral Sclerosis (ALS, or Lou Gehrig's Disease), and/or Multiple Sclerosis (MS), and cognitive, learning or memory impairments resulting therefrom.

An additional embodiment comprises compositions and methods for decreasing NFkB or IL-6 levels by using anti-NFkB or anti-IL-6 antibodies, respectively (which can be monoclonal, recombinant, fragments, humanized, and the like), such as CNTO-328, a human-mouse chimeric monoclonal antibody (Mab) to IL-6 (Centocor, Inc., Horsham, Pa.), which recognizes human IL-6 and enhances its degradation. CNTO-328 is reported to have a plasma half-life of roughly 17 days and thus in one embodiment is administered at periods from about 2 to 6 weeks, depending on individual variation in metabolism of the antibody.

An additional embodiment comprises compositions and methods for lowering IL-6 levels or effects is through administration of IL-10. IL-10 regulates production and thus levels of IL-6. In one aspect, the invention provides for direct administration of IL-10, for example as a humanized IL-10 preparation (e.g., ilodecakin, TENOVIL™, Schering-Plough, Kenilworth, N.J.) to lower IL-6 production. An additional embodiment comprises use of small-molecule IL-10 mimetics (as IL-10 agonists—mimics) to lower IL-6 levels or effects.

This invention for the first time identifies novel pathways, including IL-6 to any member of the NADPH oxidase enzyme family, to superoxide and/or hydrogen peroxide production, which leads to dysfunction of the inhibitory neurons associated with these vulnerable circuits, e.g., involved in psychosis, schizophrenia, and many dementing disorders, CNS inflammation, delirium, depression, traumatic war neurosis, post traumatic stress disorder (PTSD) or post-traumatic stress syndrome (PTSS), Amyotrophic Lateral Sclerosis (ALS, or Lou Gehrig's Disease), and/or Multiple Sclerosis (MS), and cognitive, learning or memory impairments resulting therefrom, and frailty syndrome (FS) and aging. This invention provides alternative embodiments using novel therapeutic targets to treat, ameliorate or prevent pathologies or inflammation in the central nervous system (CNS), or the brain, e.g., schizophrenia, psychosis, delirium, e.g., post-operative delirium, drug-induced psychosis, psychotic features associated with frailty syndrome (FS), aging; depression and/or dementias, traumatic war neurosis, post traumatic stress disorder (PTSD) or post-traumatic stress syndrome (PTSS), Amyotrophic Lateral Sclerosis (ALS, or Lou Gehrig's Disease), and/or Multiple Sclerosis (MS), and cognitive, learning or memory impairments resulting therefrom, and frailty syndrome (FS) and aging; wherein the novel therapeutic target include for example: NFkB, IL-6, IL-6-R or any member of the NADPH oxidase, to decrease superoxide and/or hydrogen peroxide production by any member of the NADPH oxidase. In alternative embodiments, the invention for the first time provides mechanistic treatments (as opposed to symptomatic treatments), including compositions and methods, for these important neuropathological conditions.

The inventors have verified these findings on an art-accepted experimental animal model for schizophrenia and psychosis. This model is commonly used to study schizophrenia and psychosis, and reproduces a majority of the positive and negative symptoms associated with these conditions, and also recapitulates much of the neuroanatomical changes found in individuals with schizophrenia, psychosis and in individuals showing greater vulnerability to drug-induced or post-operative psychotic episodes. This invention provides compositions and methods to ameliorate frailty syndrome (FS), aging, schizophrenia, situational psychosis (post-operative, drug-induced, depression-associated, in dementia) and dementia associated with neurodegenerative diseases such as Alzheimer's disease, Lewy Body Disease, Parkinson's Disease, Huntington's Disease, Multi-infarct dementia, senile dementia or Frontotemporal Dementia, Amyotrophic Lateral Sclerosis (ALS, or Lou Gehrig's Disease), and/or Multiple Sclerosis (MS), and cognitive, learning or memory impairments resulting therefrom, and/or neurodegeneration associated with infection or trauma, e.g., human immunodeficiency virus (HIV) infection, or bacterial, yeast and/or viral infections from, e.g., *Haemophilus, Cryptococcus, Filobasidiella, Neisseria, Rickettsia* or *Borrelia* infections.

This invention provides treatments (e.g., formulations and methods) using any monoclonal antibody against IL-6 receptor, e.g., tociluzimab—which is already clinically approved.

This invention demonstrates that selective dysfunction of the parvalbumin-immunoreactive subpopulation of fast-spiking, inhibitory interneurons in cortex is an underlying cause for both the psychotic episodes observed in schizophrenic patients. While the invention is not dependent on any particular mechanism of action, the invention is based in part on the observation that decreased expression of GAD67 and parvalbumin (PV) in these PV-interneurons is a consistent finding in postmortem brain from schizophrenic patients, and that schizophrenic patients exhibit neurocognitive evidence of dysfunctional GABA inhibitory systems. Sub-anesthetic doses of NMDA receptor (NMDA-R) antagonists (e.g. ketamine) were used to model its neurocognitive features because they reproduce both negative and positive symptoms of schizophrenia.

Intraperitoneal (ip) injection of sub-anesthetic ketamine on two consecutive days in mice caused a significant induction of NADPH oxidase (Nox; or Nox2 the respiratory burst oxidase), in brain, and this induction was accompanied by a significant increase in Nox-dependent superoxide and/or hydrogen peroxide production in neurons in vivo and in vitro, and in synaptosomes.

In addition, treatment of mice with a brain-permeable superoxide (SOD) mimetic or the selective Nox inhibitor, apocynin, not only blocked ketamine-induced superoxide and/or hydrogen peroxide production, but fully rescued the phenotype changes in PV-interneurons, thus demonstrating in vivo the efficacy of embodiments of the compositions and methods of the invention.

It was also determined that administration of interleukin-6 (IL-6) reproduced the ketamine effects in vivo and in vitro; IL-6 acts downstream of ketamine, linking known CNS inflammatory changes in schizophrenia with altered inhibitory neurotransmitter systems. The invention demonstrates that ketamine results in induction of Nox2 in neurons through IL-6 signaling, and that Nox2-dependent neuronal superoxide and/or hydrogen peroxide production mediates the loss of phenotype (i.e. decreased GAD67 and parvalbumin expression) and function (altered electrophysiology) of PV-positive interneurons in prefrontal cortex.

Ketamine treatment in animals or neuronal cultures increases expression of Nox2 and Nox-dependent superoxide and/or hydrogen peroxide production, and leads to loss of the GABAergic phenotype of PV-interneurons. Prevention of ketamine-induced disinhibition using the GABA$_{(A)}$ agonist muscimol attenuated these effects in primary cultures, whereas IL-6 exposures reproduced the ketamine effects. Treatment of primary cultures with ketamine increases the expression of IL-6 mRNA, and injection of IL-6 increased Nox2 expression and activity in brain and in synaptosomes. While the invention is not limited by any particular mechanism of action, the invention demonstrates that the following sequence of events can be triggered by sub-anesthetic doses of NMDA-receptor antagonists:

1) NMDA receptor antagonists, in part through inhibition of NR2A-containing receptors in PV-interneurons, induce disinhibition of circuitry in the PFC and other cortical regions, leading to increased glutamate release.
2) This increased glutamate leads to increased IL-6 and to the activation of neuronal Nox, and O$_2$. production.
3) IL-6 induces Nox subunits, which further increase O$_2$. production at synaptic sites.
4) Nox-dependent O$_2$. mediates oxidation of key ion channels (e.g. redox site on the NMDA receptor itself), and key enzymes (i.e. serine-racemase) leading to a secondary hypofunction of cortical circuits.
5) The initial hypoNMDA state, mediated first by the NMDA-R antagonist and then by O$_2$.-dependent inhibition of NMDA-R via its redox site (and possibly through redox-dependent effects on other synaptic proteins), leads to a resetting of excitatory transmission. This decreased glutamatergic transmission is detected by PV-interneurons resulting in reduced expression of parvalbumin, GAD67, nicotinic receptors, GAT-1, and thus in a chronically decreased inhibitory tone in forebrain structures.

This sequence of events (from 1 to 4) appears to be relevant to schizophrenia in its initial phase, when psychotic episodes are more frequent, but can also lead to sustained dysfunction of inhibitory circuits, involving PV-interneurons throughout the brain.

While the invention is not limited by any particular mechanism of action, the invention demonstrates that increased levels of IL-6 in schizophrenic patients are in part responsible for inducing a mild inflammatory state in the CNS (brain) which activates superoxide and/or hydrogen peroxide production by any member of the NADPH oxidase enzyme family ("Nox"), e.g., NADPH oxidase-2, to cause dysfunction and the well-described loss of GABAergic phenotype of PV-interneurons, specifically. This pathway appears to also underlie the reduced antioxidant capacity and decreased glutathione content that has been consistently observed in schizophrenic subjects.

Thus, this invention provides prophylactic and ameliorative treatments addressing the basic pathobiology and pathophysiology of CNS inflammation, schizophrenia, delirium, depression, psychosis, traumatic war neurosis, post traumatic stress disorder (PTSD) and post-traumatic stress syndrome (PTSS), Amyotrophic Lateral Sclerosis (ALS, or Lou Gehrig's Disease), and/or Multiple Sclerosis (MS), frailty syndrome (FS), aging, and cognitive, learning or memory impairments resulting therefrom; and the invention provides compositions and methods comprising use of anti-IL-6 (e.g., tociluzimab, a clinically-approved mAb for IL-6R), anti-NFκB (in clinical development for cancer) and brain-targeted anti-Nox compositions, including anti-Nox inhibitory nucleic acid sequences and anti-Nox antibodies. These compositions and methods of the invention can be optimized using model systems and patients to determine optimal formulations and dosage and treatment regimens for ameliorating or preventing frailty syndrome (FS), aging, psychosis, schizophrenia, depression, delirium, CNS inflammation and the like, and cognitive, learning or memory impairments resulting therefrom, associated with these diseases and conditions. Thus, in alternative embodiments, compositions and methods of the invention target NFkB, IL-6, IL-6-R or any member of the NADPH oxidase enzyme family to provide novel non-neurotransmitter-based therapeutic treatments for frailty syndrome (FS), aging, psychosis, schizophrenia, depression, delirium, CNS inflammation, drug-induced psychosis, psychotic features associated with frailty syndrome (FS), aging, depression and/or dementias; traumatic war neurosis, post traumatic stress disorder (PTSD) and/or post-traumatic stress syndrome (PTSS), and/or Amyotrophic Lateral Sclerosis (ALS, or Lou Gehrig's Disease) and/or Multiple Sclerosis (MS), and the like, and cognitive, learning or memory impairments resulting therefrom.

In alternative embodiments, compositions and methods of the invention are used to ameliorate (including to slow, reverse or abate) the increasing vulnerability to neurodegenerative disorders associated with frailty syndrome (FS), aging, pathologies, diseases (including infections) and conditions associated with an increased amount of CNS inflammation and/or CNS oxidative stress, including Alzheimer's disease, Lewy Body Disease, Parkinson's Disease, Huntington's Disease, Multi-infarct dementia, senile dementia or Frontotemporal Dementia, PTSD, PTSS, Amyotrophic Lateral Sclerosis (ALS, or Lou Gehrig's Disease), and/or Multiple Sclerosis (MS), and the like, and cognitive, learning or memory impairments resulting therefrom. See Examples 3 and 4, below.

Generating and Manipulating Nucleic Acids

In alternative aspects, the invention provides, e.g., isolated, synthetic and/or recombinant nucleic acids encoding inhibitory nucleic acids (e.g., siRNA, microRNA, antisense) that can inhibit the expression of genes or messages of any member of the NADPH oxidase, particularly NADPH oxidase in brain cells such as parvalbumin-positive GABAergic interneurons in the cortex. The nucleic acids of the invention can be made, isolated and/or manipulated by, e.g., cloning and expression of cDNA libraries, amplification of message or genomic DNA by PCR, and the like.

The nucleic acids used to practice this invention, whether RNA, iRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides (e.g., anti-NFkB, anti-IL-6, anti-IL-6-R, anti-Nox antibodies used to practice this invention) generated from these nucleic acids can be individually isolated or cloned and tested for a desired activity. Any recombinant expression system can be used, including bacterial, fungal, mammalian, yeast, insect or plant cell expression systems.

Alternatively, these nucleic acids can be synthesized in vitro by well-known chemical synthesis techniques, as described in, e.g., Adams (1983) J. Am. Chem. Soc. 105: 661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORA- TORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

The invention provides and uses fusion proteins and nucleic acids encoding them. Any polypeptide used to practice this invention (e.g., an antibody inhibitory to Nox, NFkB, IL-6 or IL-6-R activity) can be fused to a heterologous peptide or polypeptide, such as a peptide for targeting an inhibitory compound used to practice this invention to brain cells such as parvalbumin-positive GABA-ergic interneurons in the cortex; or the heterologous peptide or polypeptide can be an N-terminal identification peptide which imparts a desired characteristic, such as fluorescent detection, increased stability and/or simplified purification. Peptides and polypeptides used to practice this invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441-53.

Nucleic acids or nucleic acid sequences used to practice this invention can be an oligonucleotide, nucleotide, polynucleotide, or to a fragment of any of these, to DNA or RNA of genomic or synthetic origin which may be single-stranded or double-stranded and may represent a sense or antisense strand, to peptide nucleic acid (PNA), or to any DNA-like or RNA-like material, natural or synthetic in origin. Compounds use to practice this invention include "nucleic acids" or "nucleic acid sequences" including oligonucleotide, nucleotide, polynucleotide, or any fragment of any of these; and include DNA or RNA (e.g., mRNA, rRNA, tRNA, iRNA) of genomic or synthetic origin which may be single-stranded or double-stranded; and can be a sense or antisense strand, or a peptide nucleic acid (PNA), or any DNA-like or RNA-like material, natural or synthetic in origin, including, e.g., iRNA, ribonucleoproteins (e.g., e.g., double stranded iRNAs, e.g., iRNPs).

Compounds use to practice this invention include nucleic acids, i.e., oligonucleotides, containing known analogues of natural nucleotides. Compounds use to practice this invention include nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156. Compounds use to practice this invention include "oligonucleotides" including a single stranded polydeoxynucleotide or two complementary polydeoxynucleotide strands that may be chemically synthesized. Compounds use to practice this invention include synthetic oligonucleotides having no 5' phosphate, and thus will not ligate to another oligonucleotide without adding a phosphate with an ATP in the presence of a kinase. A synthetic oligonucleotide can ligate to a fragment that has not been dephosphorylated.

In alternative aspects, compounds used to practice this invention include genes or any segment of DNA involved in producing a polypeptide chain (e.g., an anti-IL-6 antibody); it can include regions preceding and following the coding region (leader and trailer) as well as, where applicable, intervening sequences (introns) between individual coding segments (exons). "Operably linked" can refer to a functional relationship between two or more nucleic acid (e.g., DNA) segments. In alternative aspects, it can refer to the functional relationship of transcriptional regulatory sequence to a transcribed sequence. For example, a promoter can be operably linked to a coding sequence, such as a nucleic acid used to practice this invention, if it stimulates or modulates the transcription of the coding sequence in an appropriate host cell or other expression system. In alternative aspects, promoter transcriptional regulatory sequences can be operably linked to a transcribed sequence where they can be physically contiguous to the transcribed sequence, i.e., they can be cis-acting. In alternative aspects, transcriptional regulatory sequences, such as enhancers, need not be physically contiguous or located in close proximity to the coding sequences whose transcription they enhance.

In alternative aspects, the invention comprises use of "expression cassettes" comprising a nucleotide sequence used to practice this invention, which can be capable of affecting expression of the nucleic acid, e.g., a structural gene or a transcript (i.e., encoding NFkB, interleukin-6 (IL-6) or any member of the NADPH oxidase) in a host compatible with such sequences. Expression cassettes can include at least a promoter operably linked with the polypeptide coding sequence or inhibitory sequence; and, in one aspect, with other sequences, e.g., transcription termination signals. Additional factors necessary or helpful in effecting expression may also be used, e.g., enhancers.

In alternative aspects, expression cassettes used to practice this invention also include plasmids, expression vectors, recombinant viruses, any form of recombinant "naked DNA" vector, and the like. In alternative aspects, a "vector"

used to practice this invention can comprise a nucleic acid that can infect, transfect, transiently or permanently transduce a cell. In alternative aspects, a vector used to practice this invention can be a naked nucleic acid, or a nucleic acid complexed with protein or lipid. In alternative aspects, vectors used to practice this invention can comprise viral or bacterial nucleic acids and/or proteins, and/or membranes (e.g., a cell membrane, a viral lipid envelope, etc.). In alternative aspects, vectors used to practice this invention can include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and can include both the expression and non-expression plasmids. In alternative aspects, the vector used to practice this invention can be stably replicated by the cells during mitosis as an autonomous structure, or can be incorporated within the host's genome.

In alternative aspects, "promoters" used to practice this invention include all sequences capable of driving transcription of a coding sequence in a cell, e.g., a mammalian cell such as a brain cell. Thus, promoters used in the constructs of the invention include cis-acting transcriptional control elements and regulatory sequences that are involved in regulating or modulating the timing and/or rate of transcription of a gene. For example, a promoter used to practice this invention can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription.

"Constitutive" promoters used to practice this invention can be those that drive expression continuously under most environmental conditions and states of development or cell differentiation. "Inducible" or "regulatable" promoters used to practice this invention can direct expression of the nucleic acid of the invention under the influence of environmental conditions or developmental conditions. Examples of environmental conditions that may affect transcription by inducible promoters used to practice this invention include the presence of an inducing factor administered to a subject. "Tissue-specific" promoters used to practice this invention can be transcriptional control elements that are only active in particular cells or tissues or organs, e.g., in brain cells. Tissue-specific regulation may be achieved by certain intrinsic factors that ensure that genes encoding proteins specific to a given tissue, e.g., brain, are expressed.

Antisense Inhibitory Nucleic Acid Molecules

In alternative embodiments, the invention provides antisense inhibitory nucleic acid molecules capable of decreasing or inhibiting expression of NFkB, IL-6, IL-6-R, or any member of the NADPH oxidase enzyme family on either a transcriptional and/or translational level. Naturally occurring or synthetic nucleic acids can be used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl)glycine units can be used. Antisense oligonucleotides having phosphorothioate linkages can also be used, as described in WO 97/03211; WO 96/39154; Mata (1997) Toxicol Appl Pharmacol 144:189-197; Antisense Therapeutics, ed. Agrawal (Humana Press, Totowa, N.J., 1996). Antisense oligonucleotides having synthetic DNA backbone analogues provided by the invention can also include phosphoro-dithioate, methylphosphonate, phosphoramidate, alkyl phosphotriester, sulfamate, 3'-thioacetal, methylene (methylimino), 3'-N-carbamate, and morpholino carbamate nucleic acids.

RNA Interference (RNAi)

In one aspect, the invention provides an RNA inhibitory molecule, a so-called "RNAi" molecule, comprising a sequence capable of decreasing or inhibiting expression of NFkB, IL-6, IL-6-R, or any member of the NADPH oxidase enzyme family on either a transcriptional and/or translational level. In one aspect, the RNAi molecule comprises a double-stranded RNA (dsRNA) molecule. The RNAi molecule can comprise a double-stranded RNA (dsRNA) molecule, e.g., siRNA, miRNA (microRNA) and/or short hairpin RNA (shRNA) molecules. The RNAi molecule, e.g., siRNA (small inhibitory RNA) can inhibit expression of a gene of any member of the NADPH oxidase enzyme family, and/or miRNA (micro RNA) to inhibit translation of NFkB, IL-6, IL-6-R, or a NADPH oxidase gene.

In alternative aspects, the RNAi is about 11, 12, 13, 14, 15, 16, 17, 18, 19, 20, 21, 22, 23, 24, 25 or more duplex nucleotides in length. While the invention is not limited by any particular mechanism of action, the RNAi can enter a cell and cause the degradation of a single-stranded RNA (ssRNA) of similar or identical sequences, including endogenous mRNAs. When a cell is exposed to double-stranded RNA (dsRNA), mRNA from the homologous gene is selectively degraded by a process called RNA interference (RNAi). A possible basic mechanism behind RNAi, e.g., siRNA for inhibiting transcription and/or miRNA to inhibit translation, is the breaking of a double-stranded RNA (dsRNA) matching a specific gene sequence into short pieces called short interfering RNA, which trigger the degradation of mRNA that matches its sequence. In one aspect, the RNAi's of the invention are used in gene-silencing therapeutics, see, e.g., Shuey (2002) Drug Discov. Today 7:1040-1046. In one aspect, the invention provides methods to selectively degrade RNA using the RNAi's of the invention. The process may be practiced in vitro, ex vivo or in vivo. In one aspect, the RNAi molecules of the invention can be used to generate a loss-of-function mutation in a cell, an plant tissue or organ or seed, or a plant.

In one aspect, intracellular introduction of the RNAi (e.g., miRNA or siRNA) is by internalization of a target cell specific ligand bonded to an RNA binding protein comprising an RNAi (e.g., microRNA) is adsorbed. The ligand is specific to a unique target cell surface antigen. The ligand can be spontaneously internalized after binding to the cell surface antigen. If the unique cell surface antigen is not naturally internalized after binding to its ligand, internalization can be promoted by the incorporation of an arginine-rich peptide, or other membrane permeable peptide, into the structure of the ligand or RNA binding protein or attachment of such a peptide to the ligand or RNA binding protein. See, e.g., U.S. Patent App. Pub. Nos. 20060030003; 20060025361; 20060019286; 20060019258. In one aspect, the invention provides lipid-based formulations for delivering, e.g., introducing nucleic acids of the invention as nucleic acid-lipid particles comprising an RNAi molecule to a cell, see e.g., U.S. Patent App. Pub. No. 20060008910.

Methods for making and using RNAi molecules, e.g., siRNA and/or miRNA, for selectively degrade RNA are well known in the art, see, e.g., U.S. Pat. Nos. 6,506,559; 6,511,824; 6,515,109; 6,489,127.

Methods for making expression constructs, e.g., vectors or plasmids, from which an inhibitory polynucleotide (e.g., a duplex siRNA of the invention) is transcribed are well known and routine. A regulatory region (e.g., promoter, enhancer, silencer, splice donor, acceptor, etc.) can be used to transcribe an RNA strand or RNA strands of an inhibitory polynucleotide from an expression construct. When making a duplex siRNA inhibitory molecule, the sense and antisense strands of the targeted portion of the targeted IRES can be transcribed as two separate RNA strands that will anneal together, or as a single RNA strand that will form a hairpin loop and anneal with itself. For example, a construct targeting a portion of a gene, e.g., an NADPH oxidase enzyme coding sequence or transcriptional activation sequence, is inserted between two promoters (e.g., mammalian, viral, human, tissue specific, constitutive or other type of promoter) such that transcription occurs bidirectionally and will result in complementary RNA strands that may subsequently anneal to form an inhibitory siRNA of the invention.

Alternatively, a targeted portion of gene, coding sequence, promoter or transcript can be designed as a first and second antisense binding region together on a single expression vector; for example, comprising a first coding region of a targeted NADPH oxidase gene in sense orientation relative to its controlling promoter, and wherein the second coding region of a NADPH oxidase gene is in antisense orientation relative to its controlling promoter. If transcription of the sense and antisense coding regions of the targeted portion of the targeted gene occurs from two separate promoters, the result may be two separate RNA strands that may subsequently anneal to form a gene inhibitory siRNA, e.g., a NADPH oxidase gene-inhibitory siRNA used to practice this invention.

In another aspect, transcription of the sense and antisense targeted portion of the targeted NADPH oxidase gene is controlled by a single promoter, and the resulting transcript will be a single hairpin RNA strand that is self-complementary, i.e., forms a duplex by folding back on itself to create a NADPH oxidase gene-inhibitory siRNA molecule. In this configuration, a spacer, e.g., of nucleotides, between the sense and antisense coding regions of the targeted portion of the targeted NADPH oxidase gene can improve the ability of the single strand RNA to form a hairpin loop, wherein the hairpin loop comprises the spacer. In ones embodiment, the spacer comprises a length of nucleotides of between about 5 to 50 nucleotides. In one aspect, the sense and antisense coding regions of the siRNA can each be on a separate expression vector and under the control of its own promoter.

Inhibitory Ribozymes

The invention provides ribozymes capable of binding and inhibiting genes and/or messages (transcripts) from NFkB, IL-6, IL-6-R, or any member of the NADPH oxidase enzyme family. These ribozymes can inhibit NADPH oxidase gene activity by, e.g., targeting a genomic DNA or an mRNA (a message, a transcript). Strategies for designing ribozymes and selecting a NFkB-, IL-6-, IL-6-R-, or NADPH oxidase gene-specific antisense sequence for targeting are well described in the scientific and patent literature, and the skilled artisan can design such ribozymes using the novel reagents of the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it can be released from that RNA to bind and cleave new targets repeatedly.

Polypeptides and Peptides

In alternative embodiments, the invention provides polypeptides and peptides to inhibit or decrease the amount of active NFkB, IL-6, IL-6-R, any member of the NADPH oxidase enzyme family, and/or superoxide and/or hydrogen peroxide production by inhibiting or decreasing the activity of the enzyme NADPH oxidase and/or IL-6 or IL-6 receptor (IL-6-R), including antibodies or peptides for inhibiting IL-6, IL-6-R and/or NADPH oxidase activity in the brain. In alternative embodiments, NFkB, IL-6, IL-6-R and/or NADPH oxidase inhibitors used to practice this invention are proteins or antibodies that specifically bind to and inhibit the activity of NFkB, IL-6, IL-6-R and/or NADPH oxidase enzymes.

Polypeptides and peptides used to practice the invention can be isolated from natural sources, be synthetic, or be recombinantly generated polypeptides. Peptides and proteins can be recombinantly expressed in vitro or in vivo. The peptides and polypeptides used to practice the invention can be made and isolated using any method known in the art. Polypeptide and peptides used to practice the invention can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289: 3-13) including any automated polypeptide synthesis process known in the art.

The peptides and polypeptides used to practice the invention can also be glycosylated. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence. The glycosylation can be O-linked or N-linked.

In alternative embodiments, compositions used to practice the invention comprise an oligopeptide, peptide, polypeptide, or protein sequence, or to a fragment, portion, or subunit of any of these and to naturally occurring or synthetic molecules. In alternative aspects, polypeptides used to practice the invention comprise amino acids joined to each other by peptide bonds or modified peptide bonds and may comprise modified amino acids other than the 20 gene-encoded amino acids. The polypeptides may be modified by either natural processes, such as post-translational processing, or by chemical modification techniques that are well known in the art. Modifications can occur anywhere in the polypeptide, including the peptide backbone, the amino acid side-chains and the amino or carboxyl termini. It will be appreciated that the same type of modification may be present in the same or varying degrees at several sites in a given polypeptide.

In alternative embodiments, a polypeptide used to practice the invention can have many types of modifications, e.g., modifications including acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, phosphorylation, prenylation, racemization, selenoylation, sulfation and transfer-RNA mediated addition of amino acids to protein such as arginylation. See for example, Creighton, T. E., Proteins—Structure and Molecular Properties 2nd Ed., W.H. Freeman and Company, New York (1993); *Posttranslational Covalent Modification of Proteins*, B. C. Johnson, Ed., Academic Press, New York, pp. 1-12 (1983)).

In alternative embodiments, peptides and polypeptides used to practice the invention can comprise any "mimetic" and/or "peptidomimetic" form. In alternative embodiments, peptides and polypeptides used to practice the invention can comprise synthetic chemical compounds which have substantially the same structural and/or functional characteristics of natural polypeptides. The mimetic used to practice the invention can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. Routine experimentation will determine whether a mimetic is effective for practicing the invention; e.g., a mimetic composition is effective if it has an NFkB, IL-6, IL-6-R and/or NADPH oxidase (Nox) inhibitory activity. Methodologies detailed herein and others known to persons skilled in the art may be used to select or guide one to choose effective mimetic for practicing the compositions and/or methods of this invention.

Polypeptide mimetic compositions for practicing the invention can comprise any combination of non-natural structural components. In alternative aspects, mimetic compositions for practicing the invention can comprise one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, NY). A polypeptide can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thienylalanine; D- or L-1, -2,3-, or 4-pyrenylalanine; D- or L-3 thienylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluorophenylalanine; D- or L-p-biphenylphenylalanine; D- or L-p-methoxy-biphenylphenylalanine; D- or L-2-indole(alkyl) alanines; and, D- or L-alkylamines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N—C—N—R') such as, e.g., 1-cyclohexyl-3 (2-morpholinyl-(4-ethyl) carbodiimide or 1-ethyl-3(4-azonia-4,4-dimethylpentyl) carbodiimide. Aspartyl or glutamyl can also be converted to asparaginyl and glutaminyl residues by reaction with ammonium ions. Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, e.g., under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidazoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3-dimethylproline. Histidine residue mimetics can be generated by reacting histidyl with, e.g., diethylprocarbonate or para-bromophenacyl bromide. Other mimetics that can be used include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

Polypeptides used to practice this invention can comprise signal sequences, i.e., leader sequences, e.g., for secreting a recombinant antibody or inhibitory polypeptide used to practice the invention from a production host cell.

Antibodies, Therapeutic and Humanized Antibodies

In alternative embodiments, the invention uses isolated, synthetic or recombinant antibodies that specifically bind to and inhibit an IL-6 or IL-6 receptor, or to NADPH oxidase; for example, practicing the invention can comprise use of a therapeutic monoclonal antibody inhibitory to NFkB, NADPH oxidase, IL-6 or IL-6 receptor activity (where the antibody acts as a specific antagonist (is receptor-inhibiting) for IL-6 receptors).

In alternative aspects, an antibody for practicing the invention can comprise a peptide or polypeptide derived from, modeled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267-273; Yarmush (1992) J. Biochem. Biophys. Methods 25:85-97. In alternative aspects, an antibody for practicing the invention includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, N.Y. (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62-70; Katz (1997) Annu. Rev. Biophys. Biomol. Struct. 26:27-45.

In alternative embodiments, the invention uses "humanized" antibodies, including forms of non-human (e.g., murine) antibodies that are chimeric antibodies comprising minimal sequence (e.g., the antigen binding fragment) derived from non-human immunoglobulin. In alternative embodiments, humanized antibodies are human immunoglobulins in which residues from a hypervariable region (HVR) of a recipient (e.g., a human antibody sequence) are replaced by residues from a hypervariable region (HVR) of a non-human species (donor antibody) such as mouse, rat, rabbit or nonhuman primate having the desired specificity, affinity, and capacity. In alternative embodiments, framework region (FR) residues of the human immunoglobulin are replaced by corresponding non-human residues to improve antigen binding affinity.

In alternative embodiments, humanized antibodies may comprise residues that are not found in the recipient antibody or the donor antibody. These modifications may be made to improve antibody affinity or functional activity. In alternative embodiments, the humanized antibody can comprise substantially all of at least one, and typically two, variable domains, in which all or substantially all of the hypervariable regions correspond to those of a non-human immunoglobulin and all or substantially all of Ab framework regions are those of a human immunoglobulin sequence.

In alternative embodiments, a humanized antibody used to practice this invention can comprise at least a portion of an immunoglobulin constant region (Fc), typically that of or derived from a human immunoglobulin.

However, in alternative embodiments, completely human antibodies also can be used to practice this invention, including human antibodies comprising amino acid sequence which corresponds to that of an antibody produced by a human. This definition of a human antibody specifically excludes a humanized antibody comprising non-human antigen binding residues.

In alternative embodiments, antibodies used to practice this invention comprise "affinity matured" antibodies, e.g., antibodies comprising with one or more alterations in one or more hypervariable regions which result in an improvement in the affinity of the antibody for antigen; e.g., NFkB, interleukin-6 (IL-6), IL-6-R and/or an NADPH oxidase (Nox) enzyme family member, compared to a parent antibody which does not possess those alteration(s). In alternative embodiments, antibodies used to practice this invention are matured antibodies having nanomolar or even picomolar affinities for the target antigen, e.g., NFkB, interleukin-6 (IL-6), NADPH oxidase (Nox) enzyme. Affinity matured antibodies can be produced by procedures known in the art.

Tocilizumab

In one embodiment, therapeutic monoclonal antibodies against any and/or all member(s) of the IL-6-R family are used to practice this invention; and in one aspect, the antibody acts as a specific antagonist (is receptor-inhibiting) for IL-6 receptors, e.g., tocilizumab, or ACTEMRA™ (F. Hoffmann-La Roche Ltd, Basel, Switzerland). This invention can use the known methods for formulating and administering tocilizumab, which is administered to humans for rheumatoid arthritis; see e.g., Yokota et al. (2008) Lancet 371(9617):998-1006, describing the efficacy and safety of tocilizumab in children with systemic-onset juvenile idiopathic arthritis, finding that tocilizumab is effective in children with this disease. Dosage was given was three doses of tocilizumab 8 mg/kg every 2 weeks during a 6-week open-label lead-in phase. In another study adult patients with rheumatoid arthritis received tocilizumab 8 mg/kg (n=205), tocilizumab 4 mg/kg, see Smolen, et al. (2008) Lancet 371(9617):987-97.

Tocilizumab has a long plasma half-life, so it can be administered intravenously biweekly or monthly. Published Phase I and II clinical trials showed that tocilizumab (2, 4, 5, 8 or 10 mg/kg) reduced rheumatoid arthritis disease activity significantly in a dose-dependent manner. Tocilizumab was generally safe and well tolerated. Some adverse events such as significant rises in total cholesterol and triglyceride levels, liver function disorders, decreases in white blood cell counts, diarrhea and infection were observed. The most common adverse events were infections, anaphylactic reactions, and hypersensitivity. In summary, preliminary clinical results showed that tocilizumab is effective and generally well tolerated in the treatment of IL-6-related inflammatory autoimmune diseases. Like other anti-cytokine immunotherapies, caution and close monitoring for the adverse events, especially infection, are necessary in any clinical trial or treatment regimen.

In one embodiment, therapeutic monoclonal antibodies against any and/or all member(s) of the NADPH oxidase enzyme family are used to practice this invention.
NADPH Oxidase Inhibitors The invention provides compositions and methods to inhibit or decrease the activity of the enzyme NADPH oxidase (Nox) or any member of the NADPH oxidase subfamily, e.g., Nox1, Nox2, Nox3, Nox4 or Nox5 (collectively referred to as "Nox"), as described for example e.g., in U.S. Pat. No. 6,489,149. In alternative embodiments, these NADPH oxidase inhibitors are synthetic and/or small molecules known in the art, e.g., including diphenyleneiodonium (DPI), o-methoxycatechols (e.g., apocynin and diapocynin), 4-(2-aminoethyl)-benzenesulfonyl fluoride (AEBSF), 4-hydroxy-3'-methoxy-acetophenon, N-Vanillyl-nonanamide, staurosporine and related compounds, see e.g., U.S. Patent App. Pub. Nos. 20040001818; 20060154856. In alternative embodiments, the Nox is inhibited using anti-Nox antibodies or anti-Nox inhibitory nucleic acids, as described herein.

In alternative embodiments, NADPH oxidase inhibitors comprising aromatic azines and imines as described e.g., in U.S. Pat. Nos. 5,990,137; 5,939,460; or substituted diphenylazomethines as described e.g., in U.S. Pat. No. 4,564,636, can be used to practice this invention.

In alternative embodiments, NADPH oxidase inhibitors comprising compounds similar or related to o-methoxycatechol as described e.g., in U.S. Pat. No. 6,090,851, can be used to practice this invention.

In alternative embodiments, the methods of the invention use the NADPH oxidase inhibitor apocynin (4-hydroxy-3-methoxyacetophenone), which is a major active ingredient from the rhizomes of *Picrorhiza kurroa*, a botanical plant used as an herbal medicine for treatment of a number of inflammatory diseases. The bioavailability of apocynin through its conversion to glycoconjugate but not to diapocynin has been studied and described e.g., by Wang et al. (2008) Phytomedicine 15(6-7):496-503; Epub 2007 Oct. 30. In another aspect, diapocynin is used, noting that diapocynin is 13 times more lipophilic than apocynin, as described by Luchtefeld, et al. (2008) J Agric Food Chem. 56(2):301-6. Epub 2007 Dec. 20. See also U.S. Pat. No. 6,949,586, describing formulating apocynin; and apocynin has been administered at a dosage of 1.5 mmol/L in drinking water in an animal model, see e.g., Elmarakby, et al. (2005) Hypertension 45:283.
NFkB Inhibitors The invention provides compositions and methods to inhibit or decrease the activity of NFkB. While the invention is not limited by any particular mechanism of action, in one embodiment, inhibiting or decreasing the activity of NFkB by practicing the compositions and/or methods of this invention has the effect of decreasing the amount of superoxide or hydrogen peroxide as produced by a member of the NADPH oxidase enzyme family (Nox).

In alternative embodiments, NFkB is inhibited using anti-NFkB antibodies or anti-NFkB inhibitory nucleic acids, e.g. as described herein or in U.S. Pat. No. 5,591,840. In alternative embodiments, these NFkB inhibitors are synthetic and/or small molecules.

Any NFkB inhibitory molecule can be used, e.g., as described in U.S. Pat. App. Pub. No. 20070031410; or e.g., a therapeutically effective amount of a curcumin derivative administering the curcumin derivative as described in U.S. Pat. App. Pub. No. 20060258752. In alternative embodiments, NFkB is inhibited indirectly, e.g., by inhibiting CARD11 nucleic acids as described in U.S. Pat. App. Pub. No. 20040072228; or by increasing the amount of or activating IκBs, a family of NFkB inhibitory proteins having an N-terminal regulatory domain followed by six or more ankyrin repeats and a PEST domain near their C terminus, including IκBα, IκBβ, IκBγ, IκBε, and Bcl-3.

In alternative embodiments, SN50, an inhibitor of NF-kB, is administered. This peptide comprises a nuclear localization sequence (NLS) for NFkB linked to a cell-permeable carrier. SN50 can inhibit NFkB by interfering with its translocation through the nuclear pore. In one embodiment, the SN50 peptide comprises the sequence: $H_2$N-Ala-Ala-Val-Ala-Leu-Leu-Pro-Ala-Val-Leu-Leu-Ala-Leu-Leu-Ala-Pro-Val-Gln-Arg-Lys-Arg-Gln-Lys-Leu-Met-Pro-OH (SEQ ID NO:1) (see e.g., Melotti (2001) Gene Therapy 8:1436-1442).
Superoxide Dismutase (SOD) Mimetics The invention provides compositions and methods to mimic the activity of the enzyme superoxide dismutase (SOD), wherein the mimetic decreases superoxide and/or hydrogen peroxide activity, In one embodiment, the SOD mimetic comprises a C60 fullerene, $C_3$ (tris malonic acid C60) or a malonic acid derivative.

While the invention is not limited by any particular mechanism of action, in one embodiment, the C60 fullerenes (e.g., $C_3$, or tris malonic acid C60) or other malonic acid derivatives act as superoxide dismutase mimetics, thereby augmenting the action of endogenous SOD to decrease the amount of superoxide, thereby having a cytoprotective effect, including a cytoprotective effect in the CNS. Any fullerene derivatives (e.g., $C_3$, or tris malonic acid C60) or malonic acid derivatives can be used to practice this invention, including for example a $C_3$ as described by e.g., U.S. Pat. No. 6,538,153, Hirsch, et al., describing macrocyclic malonate compounds, including the tris malonic acid C60; or as described in U.S. Pat. No. 7,070,810, Hirsch, et al., describing amphiphilic substituted fullerenes and fullerenes comprising a fullerene core and a functional moiety, and methods for making them; or as described by C. Bingel (1993) Chem. Ber. 126:1957, including compositions wherein the malonate is functionalized with a halide atom, or compositions where ester groups are replaced by alkyne groups in dialkynylmethanofullerenes. In alternative embodiments, silica coated C60 fullerene molecules or C60 fullerene-comprising silica coated carbon nanotubes can be used as described in U.S. Pat. App. Pub. No. 20080233040; or composites of fullerene nanotubes as described in U.S. Pat. App. Pub. No. 20080224100; or fullerene suspensions as described in U.S. Pat. App. Pub. No. 20080217445; or pharmaceutically acceptable compositions comprising fullerene molecules dispersed in vesicles comprising e.g., phosphatidylcholine (PC) phospholipid molecules and non-PC phospholipid molecules, as described in U.S. Pat. App. Pub. No. 20080213352; or synthetically modified fullerene molecules as described in U.S. Pat. App. Pub. No. 20080213324.

Pharmaceutical Compositions

The invention provides pharmaceutical compositions and methods to inhibit or decrease the amount of active NFkB, IL-6, NADPH oxidase enzymes, and/or superoxide and/or hydrogen peroxide production, by inhibiting or decreasing the activity of the enzyme NADPH oxidase enzymes, and/or NFkB, IL-6 or IL-6 receptor (IL-6-R), including pharmaceutical compositions, e.g., in the manufacture of medicaments for inhibiting NFkB, IL-6, IL-6-R and/or NADPH oxidase enzyme activity in the brain. These NFkB, IL-6, IL-6-R and/or NADPH oxidase enzyme inhibitors can be proteins, e.g., antibodies that specifically bind to and inhibit the activity of NFkB, IL-6, IL-6-R and/or NADPH oxidase enzyme, or inhibitory nucleic acids, e.g., RNAi such an iRNA or micro-inhibitory RNA acting at the transcriptional and/or translations level.

The invention provides pharmaceutical compositions comprising compounds that act as a superoxide dismutase mimetic to decrease superoxide and/or hydrogen peroxide levels and/or production.

In alternative embodiments, compositions used to practice this invention, including NFkB, IL-6, IL-6-R and/or NADPH oxidase enzyme inhibitory compositions, or compositions comprising compounds that act as a superoxide dismutase mimetic to decrease superoxide and/or hydrogen peroxide levels and/or production, are formulated with a pharmaceutically acceptable carrier. In alternative embodiments, the pharmaceutical compositions used to practice the invention can be administered parenterally, topically, orally or by local administration, such as by aerosol or transdermally. The pharmaceutical compositions used to practice the invention can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's").

Therapeutic agents used to practice the invention, including small molecules, inhibitory nucleic acids and antibodies, can be administered alone or as a component of a pharmaceutical formulation (composition). The compounds may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions used to practice the invention include those suitable for oral/nasal, topical, parenteral, rectal, and/or intravaginal administration. The formulations may conveniently be presented in unit dosage form and may be prepared by any methods well known in the art of pharmacy. The amount of active ingredient (including small molecules, inhibitory nucleic acids and antibodies) which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

Pharmaceutical formulations used to practice the invention can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (I.e., dosage).

Pharmaceutical preparations used to practice the invention can also be used orally using, e.g., push-fit capsules made of gelatin, as well as soft, sealed capsules made of gelatin and a coating such as glycerol or sorbitol. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., a chimeric polypeptide or peptidomimetic used to practice this invention, e.g., an antibody) in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil-based pharmaceuticals are particularly useful for administration of the hydrophobic active agents used to practice the invention. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

Pharmaceutical formulations used to practice the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

Pharmaceutical compounds used to practice the invention can also be administered by in intranasal, intraocular and intravaginal routes including suppositories, insufflation, powders and aerosol formulations (for examples of steroid inhalants, see Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In practicing this invention, the pharmaceutical compounds can be delivered by transdermally, by a topical route, formulated as applicator sticks, solutions, suspensions, emulsions, gels, creams, ointments, pastes, jellies, paints, powders, and aerosols.

In practicing this invention, the pharmaceutical compounds can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

Slow release in the body of active ingredients used to practice this invention also can be administered by controlled release means or by delivery devices that are well known to those of ordinary skill in the art; including e.g., those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566. These formulations and dosages can be used to provide slow or control led-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art can be readily selected for use with the active ingredients used to practice this invention. Practicing this invention also encompasses single unit dosage forms, e.g., suitable for injection, spray and/or oral administration such as, but not limited to, tablets, capsules, gelcaps, and caplets that are adapted for controlled-release.

In practicing this invention, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In alternative embodiments, compounds used to practice the invention are also formulated using cyclodextrins or cycloamyloses, e.g., to take advantage of the ability of cyclodextrins to form complexes with hydrophobic molecules, including inhibitory small molecules. Mechanicallyinterlocked molecules structures and architectures, such as rotaxanes and catenanes, can be made using compounds used to practice this invention and cyclodextrins. Cyclodextrins used in these embodiments can be any cyclic oligosaccharide, e.g., composed of 5 or more α-D-glucopyranoside units linked 1→4, as in amylose, a fragment of starch, or, a cyclodextrins comprising glucose monomers ranging from six to eight units in a ring, creating a cone shape α-cyclodextrin: six membered sugar ring molecule, or β-cyclodextrin: seven sugar ring molecule, or γ-cyclodextrin: eight sugar ring molecule. Other cyclodextrins or cycloamyloses that can be used in formulations of this invention are described in, e.g., U.S. Pat. App. Pub. Nos. 20080119431 (describing Per-6-guanidino-, alkylamino-cyclodextrins); 20080091006 (describing nitrate ester cyclodextrin complexes); 20080058427 (describing water-soluble, cyclodextrin-containing polymers with a linear polymer chain for drug delivery); 20070259931; 20070232567; 20070232566; and see also U.S. Pat. No. 7,307,176 (describing a 2-hydroxypropyl-beta-cyclodextrin drug inclusion complex); U.S. Pat. No. 7,270,808 (describing cyclodextrin-containing polymers improve drug stability and solubility, and reduce toxicity of a small molecule therapeutic when used in vivo); U.S. Pat. Nos. 7,262,165; 7,259,153; 7,235,186; 7,157,446; 7,141,555.

The pharmaceutical compounds and formulations used to practice the invention can be lyophilized. A stable lyophilized formulation comprising a composition used to practice the invention can be made by lyophilizing a solution comprising a pharmaceutical used to practice this invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. patent app. no. 20040028670.

The compositions and formulations used to practice the invention can be delivered by the use of liposomes (see also discussion, below). By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587.

The methods of the invention can further comprise co-administration with other drugs or pharmaceuticals, e.g., compositions for treating conditions, infections, pathology and/or inflammation in the CNS (e.g., brain) caused or mediated by NFkB, IL-6, NADPH oxidase (Nox2), and superoxide and/or hydrogen peroxide production by a NADPH oxidase to treat, prevent and/or ameliorate, e.g., schizophrenia, psychosis, delirium, e.g., post-operative delirium, drug-induced psychosis, psychotic features associated with frailty syndrome (FS), aging, depression, dementias; to treat, prevent and/or ameliorate traumatic war neurosis, post traumatic stress disorder (PTSD) or post-traumatic stress syndrome (PTSS), Amyotrophic Lateral Sclerosis (ALS, or Lou Gehrig's Disease), and/or Multiple Sclerosis (MS), and cognitive, learning or memory impairments resulting therefrom, frailty syndrome (FS), aging, and related symptoms or conditions. For example, the methods of the invention and/or compositions and formulations used to practice this invention can be co-formulated with and/or co-administered with antibiotics (e.g., antibacterial or bacteriostatic peptides or proteins), particularly those effective against gram negative bacteria, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof.

Therapeutically Effective Amounts

The pharmaceuticals and formulations used to practice the invention can be administered for prophylactic and/or therapeutic treatments. In therapeutic applications, compositions are administered to a subject already suffering from a condition, infection or disease in an amount sufficient to cure, alleviate, reverse or partially arrest the clinical manifestations of the condition, infection, pathology or disease and its complications (a "therapeutically effective amount"). For example, in alternative embodiments, pharmaceutical compositions and formulations used to practice the invention are administered in an amount sufficient to treat, prevent, reverse and/or ameliorate a pathology, condition, infection or inflammation in the central nervous system (e.g., brain) caused or mediated by IL-6, NADPH oxidase enzymes, and superoxide and/or hydrogen peroxide production by a NADPH oxidase enzymes, including for example schizophrenia, psychosis, delirium, e.g., post-operative delirium, drug-induced psychosis, psychotic features associated with frailty syndrome (FS), aging, frailty syndrome (FS), depression, dementias; to treat, prevent, reverse and/or ameliorate traumatic war neurosis, post traumatic stress disorder (PTSD) or post-traumatic stress syndrome (PTSS), Amyotrophic Lateral Sclerosis (ALS, or Lou Gehrig's Disease), and/or Multiple Sclerosis (MS), and cognitive, learning or memory impairments resulting therefrom.

The amount of pharmaceutical composition adequate to accomplish a therapeutic effect is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra).

The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on the dosage and frequency as required and tolerated by the patient. The formulations should provide a sufficient quantity of active agent to effectively treat, prevent or ameliorate a conditions, diseases or symptoms as described herein. For example, an exemplary pharmaceutical formulation for oral administration of an inhibitory composition used to practice this invention can be in a daily amount of between about 0.1 to 0.5 to about 20, 50, 100 or 1000 or more ug per kilogram of body weight per day. In an alternative embodiment, dosages are from about 1 mg to about 4 mg per kg of body weight per patient per day are used. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington's, supra.

For determining and/or optimizing the therapeutically effective amount of a composition used to practice this invention, the clinician can use any diagnostic or evaluation method or technique to determine improvement in the patient, e.g., that administering a composition used to practice this invention to an individual is effective to prevent, treat and/or ameliorate schizophrenia, psychosis, delirium, e.g., post-operative delirium, drug-induced psychosis, psychotic features associated with frailty syndrome (FS), aging, depression, dementias; to treat, prevent, reverse and/or ameliorate traumatic war neurosis, post traumatic stress disorder (PTSD) or post-traumatic stress syndrome (PTSS), Amyotrophic Lateral Sclerosis (ALS, or Lou Gehrig's Disease), and/or Multiple Sclerosis (MS), and cognitive, learning or memory impairments resulting therefrom. In alternative embodiments, a method of the invention is effective if it ameliorates, e.g., improves in any detectable or quantifiable way, or slows the progression or beginning of, or decreases in any measurable or assessable way any symptom or effect, or reverses in any measurable or assessable way any symptom or effect caused by schizophrenia, psychosis, delirium, e.g., post-operative delirium, drug-induced psychosis, psychotic features associated with frailty syndrome (FS), aging, depression, dementias; traumatic war neurosis, post traumatic stress disorder (PTSD) or post-traumatic stress syndrome (PTSS), Amyotrophic Lateral Sclerosis (ALS, or Lou Gehrig's Disease), and/or Multiple Sclerosis (MS), or cognitive, learning or memory impairments resulting therefrom.

For example, schizophrenia, psychosis, delirium, e.g., post-operative delirium, drug-induced psychosis, psychotic features associated with frailty syndrome (FS), aging, depression, dementias; traumatic war neurosis, post traumatic stress disorder (PTSD) or post-traumatic stress syndrome (PTSS), Amyotrophic Lateral Sclerosis (ALS, or Lou Gehrig's Disease), and/or Multiple Sclerosis (MS), cognitive, learning or memory impairments resulting therefrom, and related conditions can be diagnosed and/or assessed (e.g., determining the progress, regression and/or severity of) by the clinician using DSM-IV or DSM-IV-TR editions (e.g., using the latest, or year 2000, edition, American Psychiatric Association) criteria. In alternative embodiments, methods and apparatus for diagnosing schizophrenia, schizophrenia disorder subgroups, or predispositions to schizophrenia disorders can be used as described e.g., in U.S. Pat. Nos. 7,338,455; 6,629,935; 5,852,489. In one embodiment, the interhemispheric switch rate of a patient is measured under conditions of increasing rate of dichoptic reversal, and comparing the switch rate with a corresponding reference switch rate to diagnose presence or absence of schizophrenia; the interhemispheric switch rate can be determined by measuring a rate of perceptual rivalry, e.g., by measuring a rate of binocular rivalry or perceptual alternations.

In alternative embodiments, to assess depression the Hamilton Depression Scale (HDS or HAMD), which is a test for measuring the severity of depressive symptoms in individuals, often those who have already been diagnosed as having a depressive disorder, can be used. HDS is also known as the Hamilton Rating Scale for Depression (HRSD) or the Hamilton Depression Rating Scale (HDRS). HDS is used to assess the severity of depressive symptoms present in both children and adults. See also U.S. Pat. No. 7,346,395, describing use of HDS to evaluate depressive symptoms.

In alternative embodiment, compositions and methods of this invention are used to ameliorate traumatic war neurosis (combat stress), post traumatic stress disorder (PTSD) or post-traumatic stress syndrome (PTSS); diagnostic criteria for PTSD, per the Diagnostic and Statistical Manual of Mental Disorders IV (Text Revision) (DSM-IV-TR), can be summarized as:

A. Exposure to a traumatic event;
B. Persistent re-experience (e.g. flashbacks, nightmares);
C. Persistent avoidance of stimuli associated with the trauma; e.g. inability to talk about things even related to the experience; avoidance of things and discussions that trigger flashbacks and re-experiencing symptoms. Fear of losing control;
D. Persistent symptoms of increased arousal, e.g. difficulty falling or staying asleep, anger and hyper-vigilance;
E. Duration of symptoms more than 1 month;
F. Significant impairment in social, occupational, or other important areas of functioning, e.g. problems with work and relationships.

Criterion A (the "stressor") can consists of two parts, both of which must apply for a diagnosis of PTSD. The first (A1) requires that "the person experienced, witnessed, or was confronted with an event or events that involved actual or threatened death or serious injury, or a threat to the physical integrity of self or others." The second (A2) requires that "the person's response involved intense fear, helplessness, or horror."

Diagnosis and assessment of ALS and MS are well known in the art; for example, in ALS, cognitive function is generally spared except in certain situations such as when ALS is associated with frontotemporal dementia, ALS also can have subtle cognitive changes of the frontotemporal type in many patients when detailed neuropsychological testing is employed. In ALS, a small percentage of patients can develop frontotemporal dementia characterized by profound personality changes; this is more common among those with a family history of dementia. A larger proportion of ALS patients experience mild problems with word-generation, attention, or decision-making; cognitive function may be affected as part of the disease process or could be related to poor breathing at night (nocturnal hypoventilation).

Nanoparticles and Liposomes

The invention also provides nanoparticles and liposomal membranes comprising compounds used to practice this invention which can target specific molecules, including biologic molecules, such as polypeptides, including cell surface polypeptides, e.g., for targeting the inhibitory compounds used to practice this invention to neurons in the brain, e.g., parvalbumin (PA)-positive interneurons. Thus, in alternative embodiments, the invention provides nanoparticles and liposomal membranes targeting neuronal cells such as PA-positive interneurons.

In alternative embodiments, the invention provides nanoparticles and liposomal membranes comprising (in addition to comprising compounds used to practice this invention)

molecules, e.g., peptides or antibodies, that selectively target neurons in the brain, e.g., parvalbumin (PA)-positive interneurons. In one aspect, the compositions used to practice this invention are specifically designed to cross the blood-brain barrier (BBB).

The invention also provides nanocells to allow the sequential delivery of two different therapeutic agents with different modes of action or different pharmacokinetics, at least one of which comprises a composition of this invention. A nanocell is formed by encapsulating a nanocore with a first agent inside a lipid vesicle containing a second agent; see, e.g., Sengupta, et al., U.S. Pat. Pub. No. 20050266067. The agent in the outer lipid compartment is released first and may exert its effect before the agent in the nanocore is released. The nanocell delivery system may be formulated in any pharmaceutical composition for delivery to patients. For example, one agent can be contained in the outer lipid vesicle of the nanocell, and another agent used to practice this invention can be loaded into the nanocore. This arrangement allows the one agent to be released first.

The invention also provides multilayered liposomes comprising compounds used to practice this invention, e.g., for transdermal absorption, e.g., as described in Park, et al., U.S. Pat. Pub. No. 20070082042. The multilayered liposomes can be prepared using a mixture of oil-phase components comprising squalane, sterols, ceramides, neutral lipids or oils, fatty acids and lecithins, to about 200 to 5000 nm in particle size, to entrap a composition of this invention.

A multilayered liposome used to practice this invention may further include an antiseptic, an antioxidant, a stabilizer, a thickener, and the like to improve stability. Synthetic and natural antiseptics can be used, e.g., in an amount of 0.01% to 20%. Antioxidants can be used, e.g., BHT, erysorbate, tocopherol, astaxanthin, vegetable flavonoid, and derivatives thereof, or a plant-derived antioxidizing substance. A stabilizer can be used to stabilize liposome structure, e.g., polyols and sugars. Exemplary polyols include butylene glycol, polyethylene glycol, propylene glycol, dipropylene glycol and ethyl carbitol; examples of sugars are trehalose, sucrose, mannitol, sorbitol and chitosan, or a monosaccharides or an oligosaccharides, or a high molecular weight starch. A thickener can be used for improving the dispersion stability of constructed liposomes in water, e.g., a natural thickener or an acrylamide, or a synthetic polymeric thickener. Exemplary thickeners include natural polymers, such as acacia gum, xanthan gum, gellan gum, locust bean gum and starch, cellulose derivatives, such as hydroxy ethylcellulose, hydroxypropyl cellulose and carboxymethyl cellulose, synthetic polymers, such as polyacrylic acid, poly-acrylamide or polyvinylpyrollidone and polyvinylalcohol, and copolymers thereof or cross-linked materials.

Liposomes can be made using any method, e.g., as described in Park, et al., U.S. Pat. Pub. No. 20070042031, including method of producing a liposome by encapsulating a therapeutic product comprising providing an aqueous solution in a first reservoir; providing an organic lipid solution in a second reservoir, wherein one of the aqueous solution and the organic lipid solution includes a therapeutic product; mixing the aqueous solution with said organic lipid solution in a first mixing region to produce a liposome solution, wherein the organic lipid solution mixes with said aqueous solution so as to substantially instantaneously produce a liposome encapsulating the therapeutic product; and immediately thereafter mixing the liposome solution with a buffer solution to produce a diluted liposome solution.

In one embodiment, liposome compositions comprising substituted ammonium and/or polyanions are used, particularly for targeting delivery of a compound used to practice this invention to the brain, as described, e.g., in U.S. Pat. Pub. No. 20070110798.

The invention also provides nanoparticles comprising compounds used to practice this invention in the form of drug-containing nanoparticles (e.g., a secondary nanoparticle), as described, e.g., in U.S. Pat. Pub. No. 20070077286. In one embodiment, the invention provides nanoparticles comprising a fat-soluble drug of this invention or a fat-solubilized water-soluble drug to act with a bivalent or trivalent metal salt.

Transport Agents for Crossing the Blood-Brain Barrier

In alternative embodiments, the invention provides pharmaceutical compositions and formulations, including nanoparticles and liposomal membranes, that can cross the blood brain barrier and/or can selectively target neurons in the brain, e.g., parvalbumin (PA)-positive interneurons. In one aspect, the compositions (including pharmaceutical compositions and formulations) used to practice this invention are specifically designed to cross the blood-brain barrier (BBB). For example, alternative embodiments include delivering compositions used to practice this invention across the BBB include liposome-based methods, where a therapeutic agent is encapsulated within a carrier; synthetic polymer-based methods, where particles are created using synthetic polymers to achieve precisely-defined size characteristics; and/or direct conjugation of a carrier to a drug, where the therapeutic agent is bound to (e.g., covalently bound to) a peptide or polypeptide carrier, which can be synthetic or natural, e.g., as the ligand insulin for uptake via transcytosis mediated by the endothelial insulin receptor. Any natural or synthetic ligand (including antibodies and small molecules) that specifically bind to the insulin receptor, transferrin receptor, leptin receptor, lipoprotein receptor and/or insulin-like growth factor (IGF) receptor can be used to cross the BBB.

Specific transporters for glucose or for large amino acids such as tryptophan also can be used to cross the BBB. Cationized albumin or the OX26 monoclonal antibody to the transferrin receptor also can be used to cross the BBB by absorptive-mediated and receptor-mediated transcytosis, respectively. Cationized monoclonal antibodies also can be used to cross the BBB. Antibodies that bind brain (BBB) endothelial cell receptors resulting in endocytosis/transcytosis of the receptor and a bound ligand, such as a composition (including pharmaceuticals and formulations) used to practice this invention, are also described e.g. in U.S. Pat. App. Pub. No. 20080019984.

For example, in one aspect, crossing the blood-brain barrier (BBB) can be accomplished by incorporating BBB protein transport peptides: such as the pentapeptide AAEAP, as described e.g. in U.S. Pat. App. Pub. No. 20080213185; or polypeptides comprising at least 10% basic amino acid residues such as arginine or lysine that have brain-localizing activity as described e.g. in U.S. Pat. App. Pub. No. 20080199436.

Ubiquinone analogs and reduced ubiquinone (ubiquinol) analogs also can be used to cross the BBB as described e.g. in U.S. Pat. App. Pub. No. 20070203080.

Another alternative embodiment encompasses an artificial low-density lipoprotein (LDL) carrier system for the targeted delivery therapeutic agents across the BBB, e.g., using artificial LDL particles comprising various lipid elements such as phosphatidyl choline, fatty-acyl-cholesterol esters, and apolipoproteins as described e.g., in U.S. Pat. App. Pub. Nos. 20080160094; 20070292413; 20070264351. Artificial low-density lipoprotein particles can facilitate transport of therapeutic agents across the BBB by transcytosis. The BBB contains type II scavenger receptors which bind LDL with high affinity. For example, one embodiment comprises use of an artificial LDL particle comprising an outer phospholipid monolayer and a solid lipid core, where the outer phospholipid monolayer comprises at least one apolipoprotein and the solid lipid core contains at least one therapeutic agent.

Synthetic polymers such as a poly(butyl cyanoacrylate) or a polyacrylamide covered with a polysorbate (e.g., POLYSORBATE 80) can be used because these particles are sufficiently hydrophilic to be water-soluble, yet are able to maintain their structural form for long periods, which protects the therapeutic agent from uptake into the liver and kidney where it is subject to natural detoxification process.

Another alternative embodiment encompasses use of synthetic poly(butyl cyanoacrylate) particles to which ApoE molecules are covalently bound. The surface of the particles are further modified by surfactants or covalent attachment of hydrophilic polymers, see e.g., U.S. Pat. No. 6,288,040.

Devices for Delivering Therapeutic Agents Directly into the Brain

In alternative embodiments, pharmaceutical compositions and formulations, including nanoparticles and liposomes, used to practice this invention are delivered directly into the brain, e.g., by various devices known in the art. For example, U.S. Pat. App. Pub. No. 20080140056, describes a rostrally advancing catheter in the intrathecal space for direct brain delivery of pharmaceuticals and formulations. Implantable infusion devices can also be used; e.g., a catheter to deliver fluid from the infusion device to the brain can be tunneled subcutaneously from the abdomen to the patient's skull, where the catheter can gain access to the individual's brain via a drilled hole. Alternatively, a catheter may be implanted such that it delivers the agent intrathecally within the patient's spinal canal. Flexible guide catheters having a distal end for introduction beneath the skull of a patient and a proximal end remaining external of the patient also can be used, e.g., see U.S. Pat. App. Pub. No. 20060129126.

In alternative embodiments, pharmaceutical compositions and formulations used to practice this invention are delivered via direct implantation of cells into a brain, for example, using any cell implantation cannula, syringe and the like, as described e.g., in U.S. Pat. App. Pub. No. 20080132878; or elongate medical insertion devices as described e.g., in U.S. Pat. No. 7,343,205; or a surgical cannula as described e.g., in U.S. Pat. No. 4,899,729. Implantation cannulas, syringes and the like also can be used for direct injection of liquids, e.g., as fluid suspensions.

In alternative embodiments, pharmaceutical compositions and formulations used to practice this invention are delivered with tracers that are detectable, for example, by magnetic resonance imaging (MRI) and/or by X-ray computed tomography (CT); the tracers can be co-infused with the therapeutic agent and used to monitor the distribution of the therapeutic agent as it moves through the target tissue, as described e.g., in U.S. Pat. No. 7,371,225.

Drug Discovery

The methods and compositions of the invention can be used in drug discovery. The methods and compositions of the invention can be used for target validation; and, in some applications, can provide a physiologically accurate and less expensive approach to screen potential drugs to treat schizophrenia, a psychosis, a dementia, delirium, depression, traumatic war neurosis, post traumatic stress disorder (PTSD) or post-traumatic stress syndrome (PTSS), Amyotrophic Lateral Sclerosis (ALS, or Lou Gehrig's Disease), and/or Multiple Sclerosis (MS), and the like, and/or to developing brain-targeted NADPH oxidase inhibitors. For example, in one aspect, the methods and compositions of the invention are used to validate the efficacy of a treatment and/or a drug for any disease, condition, genetic phenotype (e.g., a syndrome), toxic effect (e.g., poisoning), infection and/or trauma, involving an inflammation or an inflammatory component in the CNS (e.g., brain) caused or mediated by NFkB, IL-6, NADPH oxidase enzymes, and superoxide and/or hydrogen peroxide production by a NADPH oxidase; including Multiple Sclerosis (MS), Progressive Multifocal Leuko-encephalopathy, HIV encephalitis, including any neurodegenerative disease with a CNS inflammatory component (including a CNS inflammatory component caused by a treatment, such as a drug)—such as Alzheimer's disease, Lewy Body Disease, Parkinson's Disease, Huntington's Disease, Multi-infarct dementia, senile dementia or Frontotemporal Dementia, Amyotrophic Lateral Sclerosis (ALS, or Lou Gehrig's Disease), and/or Multiple Sclerosis (MS), and related diseases, infections and/or genetic conditions.

Kits and Instructions

The invention provides kits comprising compositions and methods of the invention, including instructions for use thereof. As such, kits, cells, vectors and the like can also be provided.

The invention provides kits comprising a composition that inhibits NFkB, IL-6, NADPH oxidase enzymes, and/or superoxide and/or hydrogen peroxide production by any member of the NADPH oxidase enzyme family (e.g., Nox1, Nox2, Nox3, Nox4 or Nox5), and in an alternative embodiment, the kit comprises instructions for using a method of the invention. Also provided are kits having instructions for ameliorating, preventing or reversing schizophrenia, psychosis, delirium, e.g., post-operative delirium, drug-induced psychosis, psychotic features associated with frailty syndrome (FS), aging, depression, dementias; or for ameliorating, preventing or reversing traumatic war neurosis, post traumatic stress disorder (PTSD) or post-traumatic stress syndrome (PTSS), Amyotrophic Lateral Sclerosis (ALS, or Lou Gehrig's Disease), and/or Multiple Sclerosis (MS), or cognitive, learning or memory impairments resulting therefrom, by practicing the methods of the invention.

The invention will be further described with reference to the following examples; however, it is to be understood that the invention is not limited to such examples.

EXAMPLES

Example 1

Brain NADPH-Oxidase Mediates Ketamine Effects on Parvalbumin-Expressing Fast-Spiking Interneurons This example demonstrates that the compositions and methods of the invention are effective in the amelioration of conditions, pathologies, inflammation and/or infections in the central nervous system, e.g., brain, caused or mediated by NFkB, IL-6, NADPH oxidase, and superoxide and/or hydrogen peroxide production by a NADPH oxidase, including for example the amelioration or prevention of schizophrenia, psychosis, delirium, e.g., post-operative delirium, drug-induced psychosis, psychotic features associated with frailty syndrome (FS), aging, depression, dementias, traumatic war neurosis, post traumatic stress disorder (PTSD) or post-traumatic stress syndrome (PTSS). The compositions and methods of this invention can be used to inhibit or decrease the amount of NFkB, IL-6, NADPH oxidase, and/or superoxide and/or hydrogen peroxide production by inhibiting or decreasing the activity of the enzyme NADPH oxidase and/or IL-6 and/or IL-6 receptor.

This invention demonstrates that NADPH oxidase is responsible for dysfunction of the parvalbumin (PV)-positive interneurons, and that inhibiting NADPH oxidase rescues these same neurons. This invention demonstrates that interleukin-6 (IL-6) is responsible for the induction and activation of NADPH oxidase, and that inhibition of IL-6 activity prevents the deleterious effects of Nox activation of PV-positive interneurons; thus demonstrating that the compositions and methods of the invention can be used to treat, ameliorate or prevent schizophrenia, psychosis, post-operative delirium, drug-induced psychosis, psychotic features associated with frailty syndrome (FS), aging, depression, dementias, traumatic war neurosis, post traumatic stress disorder (PTSD) or post-traumatic stress syndrome (PTSS).

The inventors found that prolonged use of ketamine induces neuronal NADPH-oxidase, which in turn has deleterious effects on PV-interneurons, and that embodiments of the compositions and methods of this invention can decrease or reverse this neuronal NADPH-oxidase increase and ameliorate these deleterious effects, such as schizophrenia, psychosis, delirium, e.g., post-operative delirium, drug-induced psychosis, psychotic features associated with frailty syndrome (FS), aging, depression, dementias, traumatic war neurosis, post traumatic stress disorder (PTSD) or post-traumatic stress syndrome (PTSS).

The compositions and methods of this invention can be used to ameliorate or prevent the negative (deleterious) effects of ketamine administration, including chronic or improper ketamine administration, or abuse of ketamine, or other NMDA-receptor antagonists; these negative effects can include a syndrome indistinguishable from schizophrenia. Ketamine's acute pro-psychotic effects occur through dis-inhibition of brain circuitry caused by diminished firing of cortical fast-spiking inhibitory interneurons. However, after prolonged use, brain activity decreases and a loss of expression of the GABA-producing enzyme glutamate decarboxylase 67 (GAD67) (indicating loss of GABAergic phenotype), and of parvalbumin develops in these interneurons through an unknown mechanism. The inventors found that prolonged use of ketamine induces neuronal NADPH-oxidase; it was found that prolonged ketamine exposure in mice induces a persistent increase in brain superoxide due to induction of neuronal NADPH-oxidase.

Decreasing superoxide and/or hydrogen peroxide production with apocynin or inhibiting its actions with a carboxyfullerene-based SOD-mimetic prevented the deleterious effects of ketamine on inhibitory interneurons in mouse prefrontal cortex. This invention identifies NADPH-oxidase as a novel avenue in the treatment of ketamine-induced psychosis and schizophrenia, and provides compositions and methods for ameliorating or preventing ketamine-induced psychosis and schizophrenia (and associated psychosis, delirium, e.g., post-operative delirium, drug-induced psychosis, psychotic features associated with frailty syndrome (FS), aging, depression, dementias, traumatic war neurosis, post traumatic stress disorder (PTSD) or post-traumatic stress syndrome (PTSS).

Exposure to the NMDA-receptor (NMDA-R) antagonists phencyclidine and ketamine, while reproducing schizophrenia symptoms in healthy human volunteers (see reference 1, below), induces an initial dis-inhibition of excitatory transmission in the PFC of rodents and non-human primates (see reference 2, below), which, after prolonged exposure, is followed by a depression in brain activity (see reference 3, below), and by loss of the GABAergic phenotype of fast-spiking parvalbumin-positive (PV) inhibitory interneurons. This loss of GABAergic phenotype includes a reduced expression of GAD67, the main isoform producing GABA, as well as that of the calcium binding protein parvalbumin and the GABA transporter 1 (see references 4 and 5, below), similarly to what was described in the dorsolateral prefrontal cortex (PFC) of postmortem schizophrenic-brain samples (see reference 6, below, for review).

PV-interneurons are involved in the generation of gamma oscillations responsible for temporal-encoding and storage/recall of information required for working memory (see reference 7, below). These interneurons receive the highest glutamatergic input amongst all GABAergic neurons in cortex (see reference 8, below), and their basal synaptic activation is controlled by calcium entry through NMDA-Rs (see reference 9, below). The subunit composition of these glutamate receptors in PV-interneurons differs from those present in neighboring pyramidal neurons (see reference 10, below), and are highly sensitive to NMDA-R antagonists such as ketamine (see reference 11, below).

The mechanism(s) by which the initial dis-inhibition of excitatory transmission created by NMDA-Rs leads to the delayed, or compensatory hypo-function of the system and to the decreased firing of PV-interneurons, are not known.

Therefore, the inventors studied whether this initial dis-inhibition is critical to the subsequent loss of GABAergic phenotype by studying the effects of the pan-GABA$_{(A)}$ agonist muscimol in reversing ketamine-mediated effects on cultured PV-interneurons, a system previously shown to respond to ketamine treatment with reductions in parvalbumin and GAD67 immunoreactivity (see reference 10, below). Increasing GABA$_{(A)}$ mediated inhibition prevented the decrease in parvalbumin (FIG. 1) and GAD67 (FIG. 5) in PV-interneurons, confirming that increased excitability is a key initial event after ketamine exposure (see reference 2, below).

Rapid increases in reactive oxygen-species production have been shown upon exposure to NMDA-R antagonists in vitro (see reference 12, below), and in vivo (see reference 13, below), but the processes initiating this increase are not clear (see reference 14, below). Interestingly, one of the most consistent findings in microarray analyses of schizophrenic brain tissue, as well as in animal models of the disease, is an increase in oxidative- and inflammatory-related gene transcripts; see (see reference 14, below) for review. Diminished antioxidant capacity in plasma and CSF of schizophrenic patients has also been shown (see references 16 and 17, below), supporting the hypothesis of increased oxidative-stress in the disease.

Expression of the superoxide-producing enzyme NADPH-oxidase (Nox) in hippocampus has been demonstrated; see e.g., see reference 18, below.

The inventors showed that dis-inhibition of neurotransmission by NMDA-R antagonists leads to an increase in Nox-activity. Superoxide and/or hydrogen peroxide production in live cells has been successfully detected by dihydroethidium (DHE) oxidation (see references 19 to 21, below). Therefore, following the oxidation product of DHE by confocal microscopy, levels of superoxide and/or hydrogen peroxide production were analyzed after prolonged exposure to low concentrations of ketamine in the culture system. We observed a significant increase in neuronal superoxide and/or hydrogen peroxide production after 24 h exposure to 0.5 µM ketamine, which was prevented by the GABA$_{(A)}$ agonist muscimol (FIGS. 1A, and B left graph) and was accompanied by the reduction of parvalbumin immunoreactivity (FIGS. 1A, and B right graph). The increase in DHE oxidation in response to ketamine was not restricted to the PV-interneuronal population, demonstrating that activation of the enzyme(s) producing superoxide occurs throughout cortical neurons.

It was next determined whether the increase in superoxide and/or hydrogen peroxide production was involved in the loss of GABAergic phenotype of PV-interneurons in the culture system. It was found that ketamine effects were prevented by co-treatment with a carboxyfullerene-based SOD-mimetic ($C_3$) (FIGS. 2A and B) (21).

Nox2 and Nox4 are the main Nox core-subunits expressed in forebrain (22). Nox2, is the main isoform expressed in professional phagocytes and requires the presence of the membrane protein p22$^{phox}$, as well as of a series of cytosolic proteins involved in the priming and activation of the enzyme, i.e. p47$^{phox}$, p67$^{phox}$, p40$^{phox}$ and Rac1. Activation of the Nox2-complex occurs upon bacterial infection and inflammatory processes. Nox4 is also dependent on p22$^{phox}$ for activity, but seems to be a constitutive enzyme not requiring activation by the cytosolic complex (22).

To test if Nox activity was involved in ketamine-mediated superoxide increase the inventors used the Nox inhibitor apocynin, which acts by preventing binding of p47$^{phox}$ to p22$^{phox}$ required for Nox activation (23). When cultures were exposed to ketamine in the presence of apocynin (Apo 0.5 mM) superoxide and/or hydrogen peroxide production was significantly reduced (FIG. 2A), and the loss of parvalbumin and GAD67 immunoreactivity in PV-interneurons was prevented (FIG. 2B). Furthermore, ketamine induced the neuronal expression of Nox2 (see FIG. S2).

To determine whether Nox-dependent superoxide was also important in ketamine effects in vivo, a sub-chronic regimen was used that consisted of intraperitoneal (IP) injections of ketamine at 30 mg/kg applied on two consecutive days to male C57BL/6 mice, followed by brain dissection 18 hours later. The acute effects of ketamine, such as behavioral effects due to disinhibition (2), are not detected in this regimen. However, this treatment permits the analysis of events that follow the initial dis-inhibition of the circuitry. A significant increase was observed in the expression of Nox2 and p22$^{phox}$, but not Nox4 (FIG. 3A) in membrane preparations of cortical tissue after ketamine treatment. This increase in protein levels was accompanied by an increase in Nox activity in synaptosomes isolated from cortical tissue of ketamine treated animals (FIG. 3B), demonstrating a synaptic localization of the active enzyme. The increased oxidase activity in synaptosomes was inhibited in vitro by apocynin (FIG. 3B), confirming that the main oxidase isoform induced by ketamine in brain is Nox2. Metabolic activities of synaptosomal mitochondria were not affected by the treatment, indicating that this potential source of ROS is not involved in ketamine effects in vivo (FIG. S3).

To assess the role of Nox activation and superoxide and/or hydrogen peroxide production in the effects of ketamine on PV-interneurons, these interneurons were characterized in mouse PFC and analyzed the effects of the two-day ketamine regimen on parvalbumin and GAD67 immunoreactivity. We observed a significant reduction in immunoreactivity for both proteins in PFC after ketamine treatment (FIG. 4A). Moreover, this treatment produced a widespread increase in oxidized DHE (FIGS. 4B and C), indicating increased superoxide and/or hydrogen peroxide production, which was prevented when animals were pretreated with the Nox inhibitor apocynin (5 mg/kg/day for 1 week in drinking water), or with the SOD-mimetic $C_3$ for one month; 1.0 mg/kg/day, ALZET™ (Cupertino, Calif.) mini-pumps. More importantly, both treatments completely prevented the ketamine-mediated loss of parvalbumin immunoreactivity in PV-interneurons (FIG. 4D).

Although the PFC seems to be more susceptible to the effects of NMDA receptor antagonists (4, 5), structural and functional deficits in hippocampus, visual and auditory regions have been shown to contribute to schizophrenia (24, 25). Substantial increases in oxidized DHE was observed in several brain regions besides the PFC, such as CA3 in the hippocampus and the reticular nucleus of the thalamus (see FIG. 4) demonstrating that increased Nox activity occurs throughout the brain upon drug exposure.

Regulatory redox sites have been found in many proteins that are involved in glutamatergic neurotransmission including the excitatory amino acid transporter EAAT1 (26), serine-racemase (27), and the NMDA receptor itself which is tightly regulated by oxidation-reduction reactions through its redox-sensitive site (28, 29). Redox agents, including glutathione, induce a highly reversible current potentiation in receptors composed of NR1:NR2A by acting on a specific redox site in NR2A, and the oxidation status of this site affects the physiological regulation of the receptor.

The higher ratio of NR2A-containing NMDA-Rs in PV-interneurons (10) should make these cells highly sensitive to changes in oxidative conditions. It appears then that a prolonged inactivation of NMDA-Rs in PV-interneurons either by blockade with the antagonists, or, more physiologically, by Nox-dependent oxidation leads to a "misinterpretation" of the lack of signal through NMDA-Rs as a decreased glutamatergic transmission. This, in turn, would be the signal the initiates the processes resulting in reduced expression of GABAergic markers and loss of inhibitory capacity in PV-interneurons, finally leading to a chronically decreased inhibitory tone in cortex.

In summary, this invention demonstrated that the diminished firing of PV-interneurons caused either by blockade of NMDA receptors, or by developmental derangements as for schizophrenia, produces the initial increased excitability in brain (2). This, in turn, activates and induces Nox, which through oxidation of synaptic proteins leads to diminished neurotransmission. This sequence may function as a normal shut-down mechanism in transient situations of increased excitatory transmission, as was recently suggested for the inactivation of serine-racemase (27).

The inventors demonstrated that NADPH-oxidase (Nox) and superoxide dismutase (SOD) are contributors to oxidative mechanisms in the psychotomimetic effects of NMDA-R antagonists and in schizophrenia and other processes involving increased brain oxidative-stress, such as CNS inflammation. Accordingly, the invention provides compositions and methods for manipulating the activation/induction mechanism of brain NADPH-oxidase (Nox), and mimicking the activity of superoxide dismutase (SOD); thus, the invention presents completely new avenues for the treatment of schizophrenia, psychosis, delirium, drug-induced psychosis, psychotic features associated with frailty syndrome (FS), aging, depression and/or dementias, traumatic war neurosis, post traumatic stress disorder (PTSD) and/or post-traumatic stress syndrome (PTSS), by manipulating NADPH-oxidase (Nox) and/or superoxide dismutase (SOD) expression and activity.

FIG. 1. Ketamine exposure in primary neuronal cultures increases superoxide and/or hydrogen peroxide production and induces the loss of parvalbumin immunoreactivity. Neuronal cultures were treated with ketamine (0.5 μM) for 24 has described (10), and DHE (1 µg/ml) was added to the cultures during the last hour of incubation. FIG. 1A, FIG. 1B, and FIG. 1C: Confocal images of representative fields depicting a PV-interneuron and surrounding neurons treated in the absence of ketamine (control) (FIG. 1A), the presence of ketamine (FIG. 1B), and co-exposure to ketamine and muscimol (FIG. 1C). FIG. 1D and FIG. 1E: Quantification results for DHE (FIG. 1D), and PV (FIG. 1E) fluorescence. Co-exposure to muscimol (10 µM) prevented the increase in oxidized DHE and loss of PV immunoreactivity (right bars in D and E). (*=significant when compared to control at P<0.001 by analysis of variance (ANOVA) followed by Tukey's test, n=5 experiments per condition).

Figure 2:
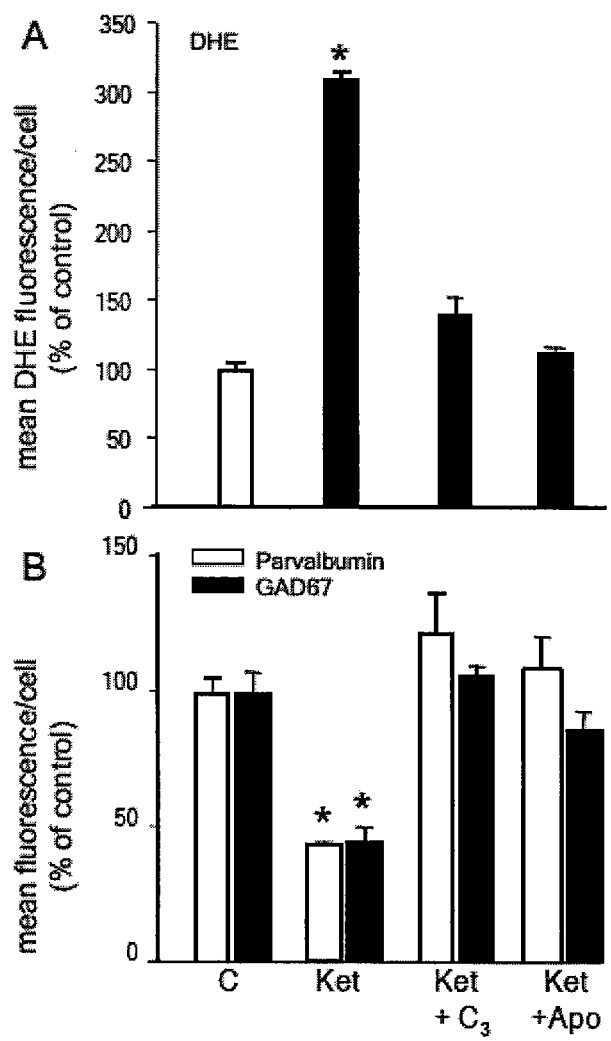
FIG. 2 graphically illustrates experimental results showing that removal of superoxide or inhibition of NADPH oxidase (Nox) activation prevents superoxide increase and reduction of parvalbumin and glutamate decarboxylase 67 (GAD67) in PV-interneurons in culture: cultures were treated with ketamine as in FIG. 1 in the absence or presence of the carboxyfullerene-based SOD-mimetic $C_3$ (20 µM) or the Nox inhibitor apocynin (0.5 mM), and quantification results for oxidized DHE fluorescence (FIG. 2A), and for parvalbumin and GAD67 fluorescence in PV-interneurons (FIG. 2B) graphically illustrated; as discussed in detail in Example 1, below.

FIG. 2. Removal of superoxide or inhibition of Nox activation prevents superoxide increase and reduction of parvalbumin and GAD67 in PV-interneurons in culture. Cultures were treated with ketamine as in FIG. 1 in the absence or presence of the carboxyfullerene-based SOD-mimetic $C_3$ (20 µM) or the Nox inhibitor apocynin (0.5 mM). Quantification results for oxidized DHE fluorescence (FIG. 2A), and for parvalbumin and GAD67 fluorescence in PV-interneurons (FIG. 2B) (*=significant when compared to control at P<0.05 by ANOVA followed by Tukey's test. n=4 experiments per condition).

Figure 3:
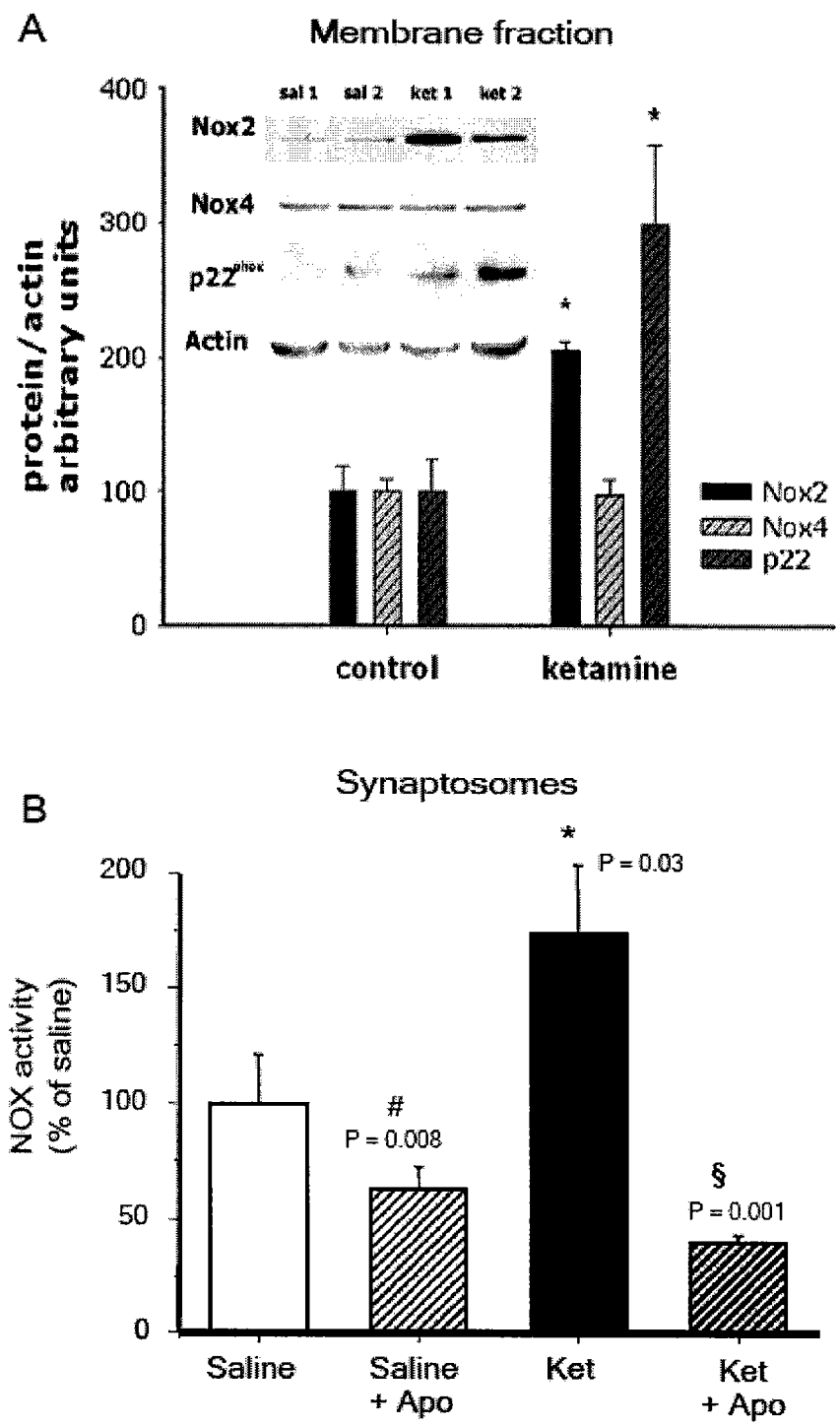
FIG. 3 illustrates in graphics and images experimental results showing that in vivo ketamine treatment increases Nox and $p22^{phox}$ protein expression in brain membranes, and increases the levels of apocynin-inhibitable Nox activity in synaptosomes.

FIG. 3. In vivo ketamine treatment increases Nox and $p22^{phox}$ protein expression in brain membranes, and increases the levels of apocynin-inhibitable Nox activity in synaptosomes. Mice were treated with ketamine (30 mg/kg) on two consecutive days followed by 18 h without drug. FIG. 3A: Membrane fractions were analyzed for the expression of the indicated proteins by Western blots (insert). Bar graphs represent the quantification of Western blots normalized for actin content. (*=significant compared to saline at P<0.001 by ANOVA followed by Tukey's test. n=4 animals/ condition). FIG. 303B: Increased Nox activity was observed in synaptosomal preparations from ketamine treated animals. This activity was inhibited by apocynin. Values of NADPH-induced oxygen consumption (nmol $O_2$/mg protein/min) were: 4.67±0.98, control; 7.9±1.8, ketamine (n=4 animals/condition).

Figure 4:
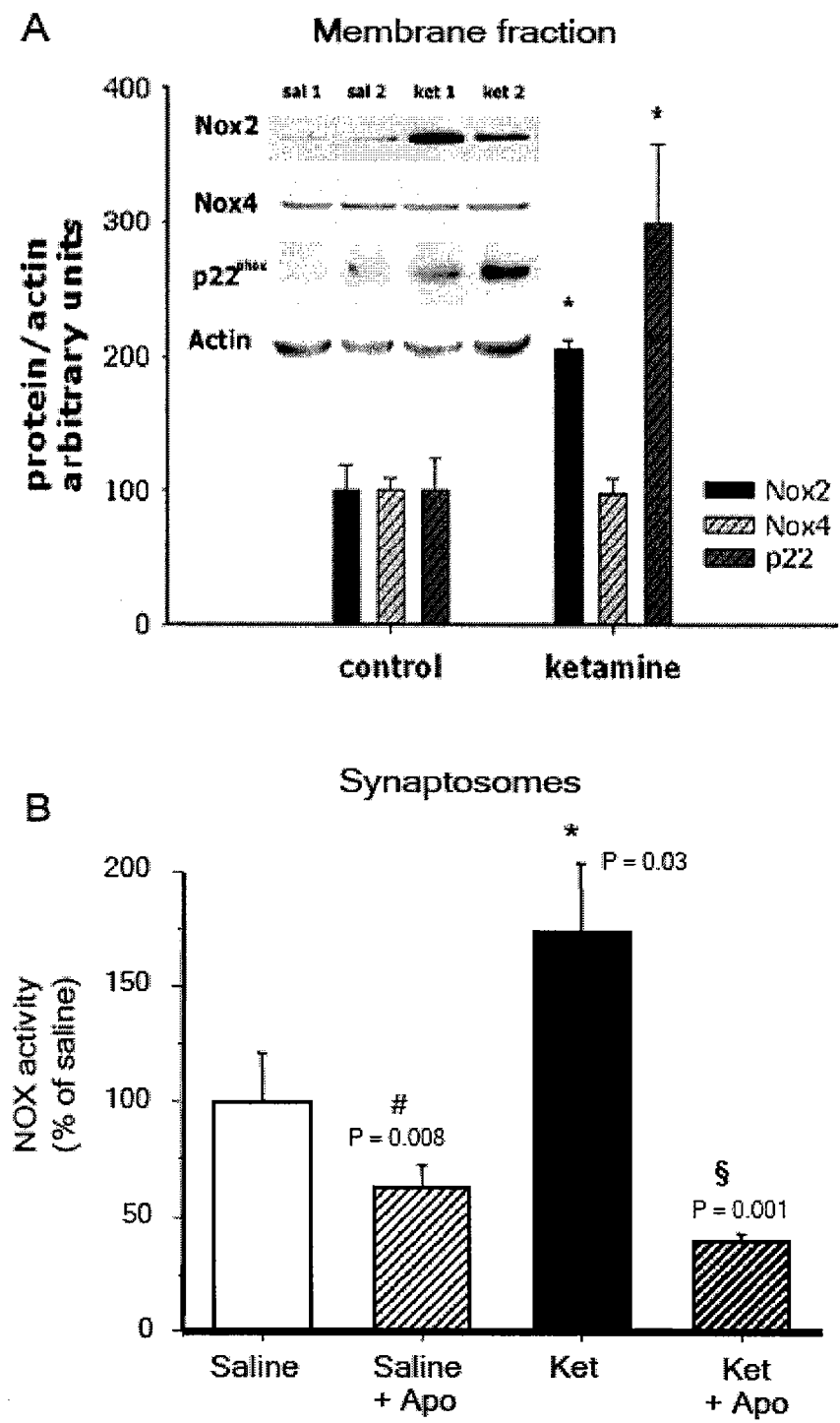
FIG. 4 illustrates in graphics and images experimental results showing that pretreatment of animals with the Nox inhibitor apocynin, or with the SOD-mimetic ($C_3$), reduces superoxide and/or hydrogen peroxide production and prevents the loss of parvalbumin immunoreactivity induced by ketamine in mouse prefrontal cortex, as described in detail in Example 1, below; animals were treated with ketamine as in FIG. 3, and coronal sections comprising the prelimbic and infralimbic regions were analyzed.

FIG. 4. Pretreatment of animals with the Nox inhibitor apocynin, or with the SOD-mimetic ($C_{3\_}$) reduces superoxide and/or hydrogen peroxide production and prevents the loss of parvalbumin immunoreactivity induced by ketamine in mouse prefrontal cortex. Animals were treated with ketamine (30 mg/kg. ip) as in FIG. 3. Coronal sections comprising the prelimbic and infralimbic regions were analyzed. FIG. 4A: parvalbumin and GAD67 expression in PV-interneurons, graph bar of FIG. 4C represents the quantification of parvalbumin and GAD67 mean fluorescence/ cell for the region normalized by the means of saline treated animals. FIG. 4B and FIG. 4C: Animals were treated with apocynin in the drinking water for 1 week (5 mg/kg/day), or during one month with the SOD-mimetic $C_3$ delivered by mini-pumps (1 mg/kg/day) before ketamine treatment. DHE was applied 30 min after the last ketamine injection. Coronal sections were quantified for parvalbumin and oxidized DHE fluorescence. n=6 animals per condition. (*,#=significance with respect to saline at the indicated P values by ANOVA followed by Tukey's test).

Figure 5:
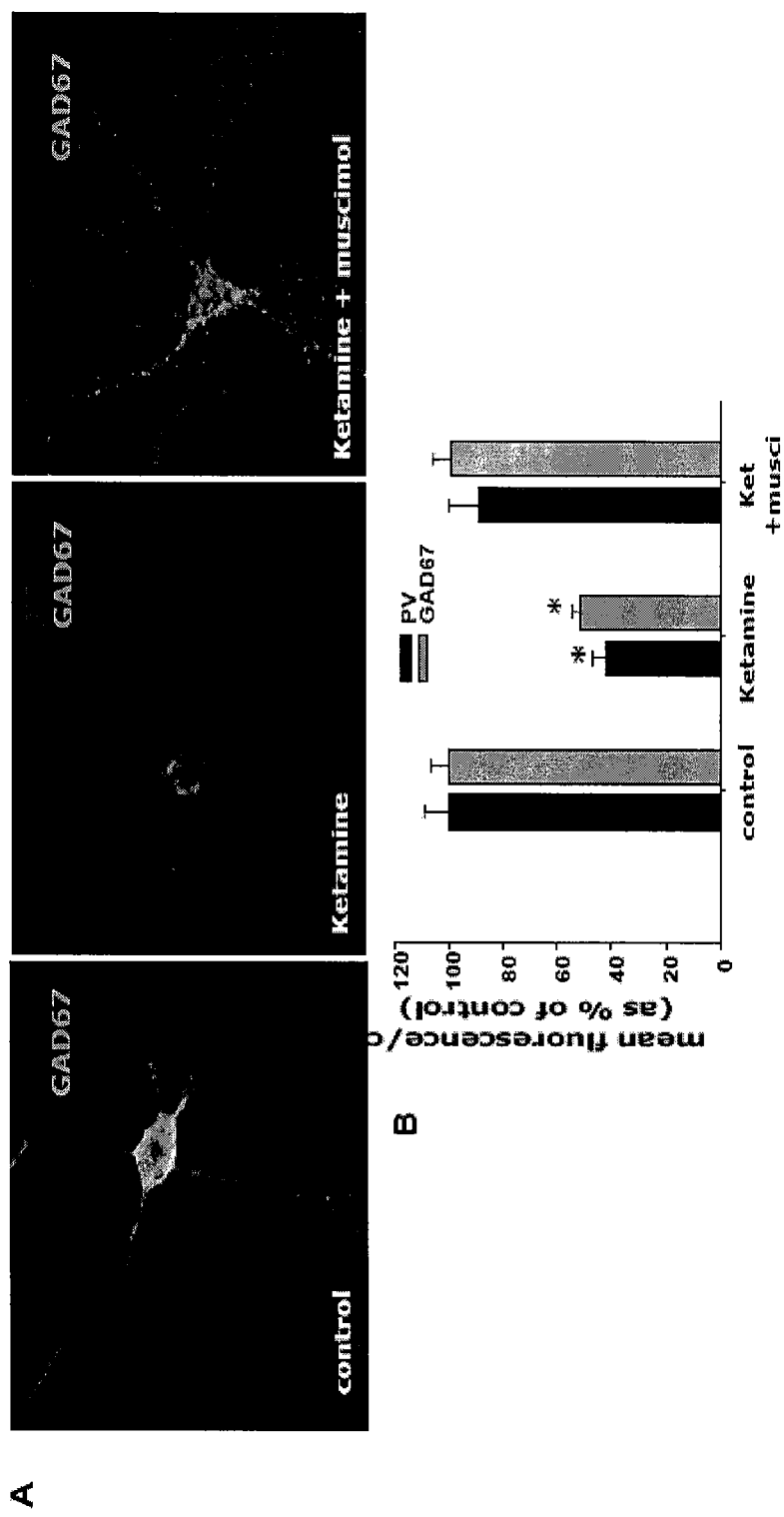
FIG. 5 illustrates in graphics and images experimental results showing increasing $GABA_{(A)}$-mediated inhibition prevents the decrease in GAD67 expression in parvalbumin-positive (PV)-interneurons after ketamine treatment in primary neuronal cultures: cultures were treated with ketamine in the absence or presence of muscimol as in FIG. 1, above, and GAD67 immunofluorescence in PV-interneurons was analyzed (FIG. 5A, left panel control; middle panel ketamine treatment; right panel ketamine and muscimol treatment)

FIG. 5. Increasing $GABA_{(A)}$-mediated inhibition prevents the decrease in GAD67 expression in parvalbumin-positive (PV)-interneurons after ketamine treatment in primary neuronal cultures. Cultures were treated with ketamine in the absence or presence of muscimol as in FIG. 1, above, and GAD67 immunofluorescence in PV-interneurons was analyzed as described in the methods section. FIG. 5A illustrates confocal images; and FIG. 5B is a bar graph schematically illustrating-summarizing the data from this study; *=significance with respect to control conditions at P=<0.001 by ANOVA followed by Tukey's test. n=5 experiments per condition.

Figure 6:
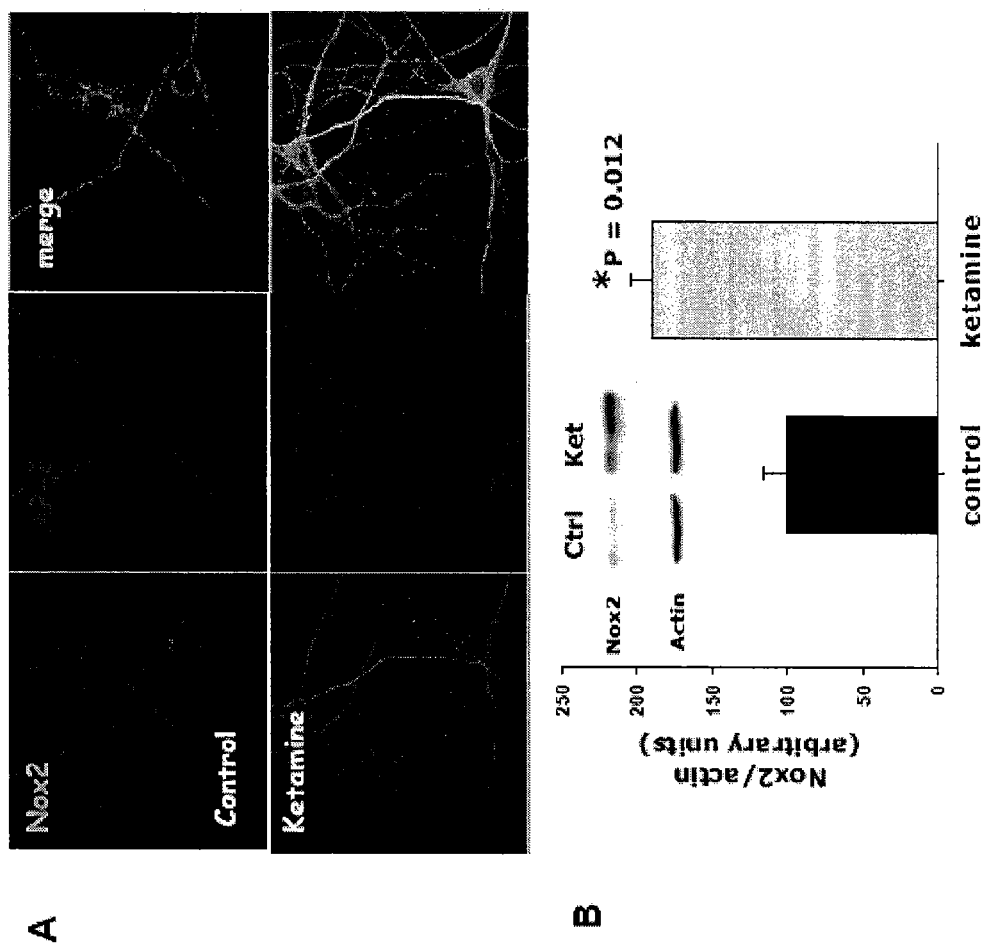
FIG. 6 illustrates in graphics and images experimental results showing that ketamine treatment increases Nox2 expression in primary neuronal cultures.

FIG. 6. Ketamine treatment increases Nox2 expression in primary neuronal cultures. FIG. 6A: Confocal image showing the increase in Nox2 immunoreactivity after 24 h of treatment with ketamine (0.5 µM) in primary cultured neurons (fluorescence quantification values: control: 100+/−8%; Ketamine: 170+/−15%. Statistically significant at P<0.001 by ANOVA followed by Tukey's multiple comparisons post-hoc test). FIG. 6B: Inset shows Western blots prepared form cultures treated as in FIG. 6A, showing increase in Nox2 protein level, with bar graph schematically illustrating-summarizing the data from this study. Cultured cells were extracted with RIPA-buffer and Western blots were run using 50 µg of protein per lane. Nox2 and actin immunoreactivities were detected as described in methods, and quantified by densitometry. The Nox2/actin ratios were calculated and expressed as percent of control. *=significant when compared to control conditions by ANOVA followed by Tukey's test. n=3 experiments.

Figure 7:
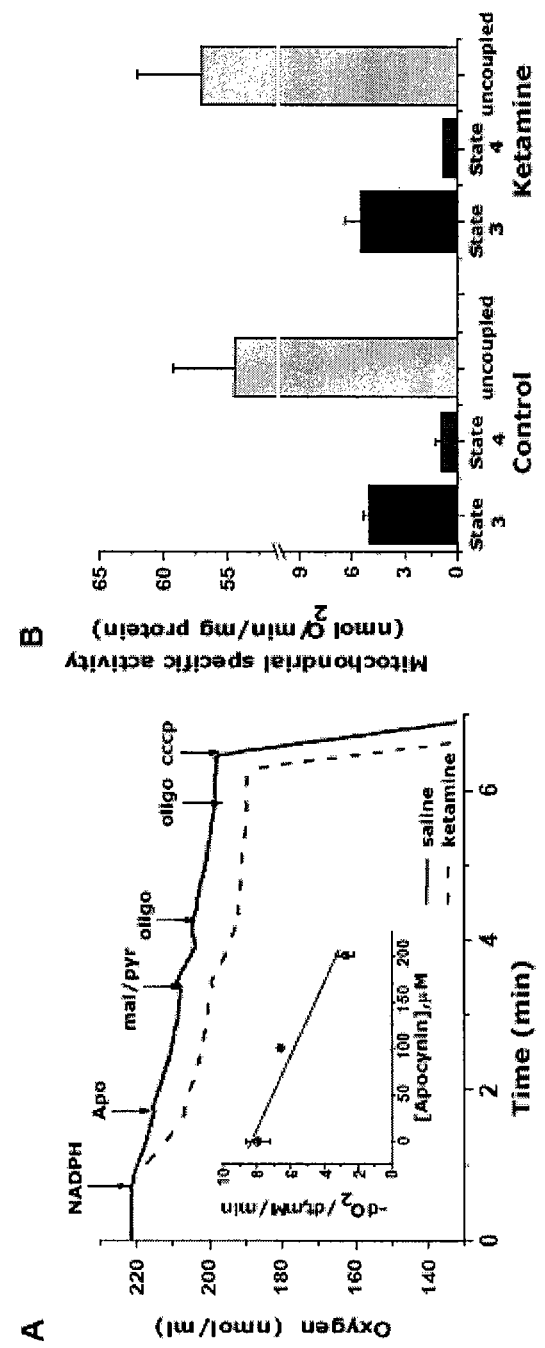
FIG. 7 graphically illustrates experimental results showing ketamine effects on synaptosomal $O_2$ consumption by Nox(s) and mitochondria.

FIG. 7. Ketamine effects on synaptosomal $O_2$ consumption by Nox(s) and mitochondria. FIG. 7A: Oxygen consumption by synaptosomal Nox(s) from cortex of saline or ketamine injected mice at 37° C. was induced by the addition of 5 mM NADPH to samples containing 2-5 mg synaptosomal protein. The inset in FIG. 7A shows the apocynin dependent inhibition of Nox activity. Respiratory function of synaptosomal mitochondria in the same preparations was then evaluated by the subsequent addition of NAD+-linked substrates (10 mM malate+10 mM pyruvate) followed by the addition of 4 µg/ml of the $F_0F_1$-ATPase inhibitor oligomycin to attain State 4 respiration, and the maximal mitochondria respiration was initiated by the addition of 0.5 µM of the protonophore uncoupling agent, CCCP. FIG. 7B: Ketamine treatment did not affect synaptosomal mitochondria. Quantifications of OXYGRAPH™ traces similar to those shown in FIG. 7A from saline- or ketamine-injected (n=4) mice were carried out. Data are mean±SEM.

Figure 8:
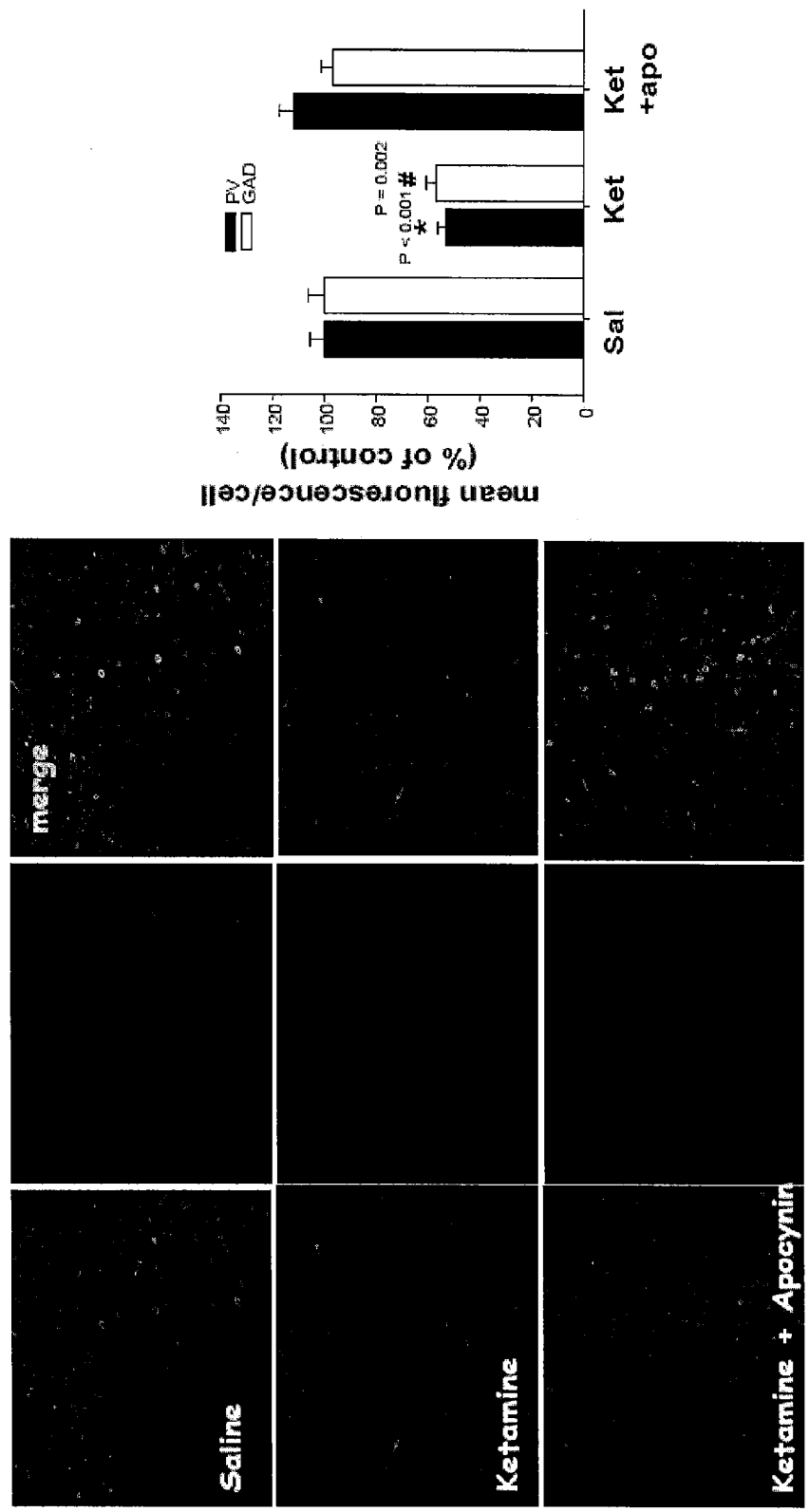
FIG. 8 illustrates in graphics and images experimental results showing ketamine-mediated decrease in parvalbumin and GAD67 immunoreactivity in PV-interneurons of the PFC is prevented by apocynin treatment; left nine panels are confocal images of parvalbumin and GAD67 stained sections of the prefrontal region depicting the decrease in immunoreactivity induced by the two-day ketamine treatment; right bar graph represents means+/−SEM values expressed as % of control (saline) conditions; as discussed in detail in Example 1, below.

FIG. 8. Ketamine-mediated decrease in parvalbumin and GAD67 immunoreactivity in PV-interneurons of the PFC is prevented by apocynin treatment. Confocal images of parvalbumin and GAD67 stained sections of the prefrontal region depicting the decrease in immunoreactivity induced by the two-day ketamine treatment. These decreases were prevented when animals were treated with apocynin in the drinking water as in FIG. 4. Images were obtained with a 10× water-immersion objective. Fluorescence intensity per cell was analyzed as described in the Methods section, below. Bar graph represents means+/−SEM values expressed as % of control (saline) conditions. *,#=significant when compared to control conditions (saline treated animals at indicated P values by ANOVA followed by Tukey's test. n=5 animals per condition. Data are mean±SEM.

Example 1

Material and Methods

Animals and treatments. Maintenance of mice and in vivo administration of ketamine, apocynin and the carboxyfullerene-based SOD-mimetic $C_3$. Male C57BL6 mice were obtained from Jackson Labs, Bar Harbor, Me., at 8-12 weeks and housed in our facility until 15 weeks when they were used for experiments. Ketamine (30 mg/kg) was applied intraperitoneally (IP) on two consecutive days at around 4 pm. DHE was applied 30 min after the last ketamine injection as described (19, 20). Briefly, two serial i.p. injections of freshly prepared dihydroethidium (27 mg/kg) are given at 30 minute intervals. Eighteen hours later, mice are anesthetized with inhaled halothane, and perfused intracardially with cold saline followed by 4% paraformaldehyde in PBS. The Nox inhibitor, apocynin (5 mg/kg/day) was given in the drinking water for a total of seven days, with an assumed intake of 13 ml $H_2O$/mouse/day, and ketamine was applied on the last two days. The SOD mimetic $C_3$ was given through ALZET™ minipumps at (1 mg/kg/day) for 30 days before ketamine injections. All animal studies were approved by the Animal Care Program at the University of California, San Diego, and are in accordance the PHS Guide for the Care and Use of Laboratory Animals, USDA Regulations, and the AVMA Panel on Euthanasia.

Neuronal Cultures.

Neuronal cultures used for confocal imaging and biochemistry were prepared from fetal (E14-15) Swiss Webster mice as previously described (10).

Synaptosomal Preparations.

For each preparation, pooling of two forebrains was found to provide sufficient protein (10-15 mg) to run one OXY-GRAPH™ measurement (see below) and Western blots. Mice were euthanized by exposure to a lethal dose of inhaled halothane, followed by cervical dislocation. Brains were rapidly removed, cortices dissected and homogenized in 10 volumes of ice-cold isolation buffer (0.32M sucrose, 1 mM EDTA, 10 mM Tris-HCl buffer, pH 7.4, 10 mM glucose). The homogenate was centrifuged at 3100 rpm for 3 min at 4° C., and the supernatant collected, and the pellet was re-homogenized in half the volume of isolation buffer and centrifuged again. Synaptosomal were then isolated as described (see reference 30, below) modified as follows, the pooled supernatants were mixed with PERCOLL™ (Sigma, St. Louis, Mo.) to a final concentration of 15%, and then layered onto a step gradient of 23% and 40% PERCOLL™, and centrifuged at 16,000 rpm for 5 minutes at 4° C. The uppermost band was extracted, rinsed in isolation buffer, centrifuged and resuspended in synaptosomal buffer (120 mM NaCl, 4.7 mM KCl, 2.2 mM $CaCl_2$, 1.2 mM $MgCl_2$, 25 mM HEPES, 1.2 mM $MgSO_4$, 1.2 mM $KH_2PO_4$, 10 mM glucose).

Nox Activity.

NADPH-dependent oxygen consumption (oximetry) was used for determining Nox activity in synaptosomal preparations. Approximately (~) 5 mg synaptosomal protein was incubated for 10 minutes at 37° C. with 200 µM digitonin and different apocynin concentrations (0-200 µM) before the activation of NOX was triggered by the addition of 5 mM NADPH. Viability of synaptosomal mitochondria in the presence of digitonin and apocynin was assessed by respiration upon the addition of 10 mM malate and 10 mM pyruvate. F0F1-ATPase inhibitor oligomycin (4 µg/mL) halted oxygen consumption and the maximal mitochondria uncoupling was established by the addition of 0.5 µM CCCP as an indication of 'healthy mitochondria'. $O_2$ utilization was measured using an oxygen Clark-type electrode, OXY-GRAPH™ (Hansatech, UK) with OXYGRAPH™ software.

Analysis of Nox Proteins by Western Blot.

Preparation of samples and subcellular fractionation is carried out as described above. For Western blotting, samples were separated by SDS-PAGE on 10-12% acrylamide gels, proteins transferred to a nitrocellulose membrane, and processed for immunodetection as described (see reference 31, below) using mouse monoclonal antibodies against Nox2 (54.1; 1:1000) and $p22^{phox}$ (44.1; 1:1000) kind gift of Dr. Quinn (see reference 32, below) and, Nox4 polyclonal (1:1500) kind gift from Dr. Goldstein (see reference 33, below), and anti-Actin (1:30000; Chemicon) and incubating at 4° C. overnight. After incubation with host-appropriate secondary Abs HRP-conjugated, specific antigens were visualized using chemiluminescence (SUPER-SIGNAL PICO™, Pierce Chemical, Rockford, Ill.). Protein content was quantified by densitometric analysis and normalized by the actin content in the same sample. Values were then expressed as % of control (saline) conditions.

Immunocytochemistry.

Fixation of neurons in culture was performed as described (10). For double immunostaining, the coverslips were incubated in 2% normal goat serum containing the following primary antibodies (Abs): mAb against GAD67 (1:1000, Chemicon), Nox2 or Nox4 (1:200. Kindly provided by Dr Quinn), a rabbit polyclonal Ab against Parvalbumin (1:3000, Swant, Bellinzona, Switzerland), or $p22^{phox}$ (1:300. Santa Cruz), and incubated for 2 h at 37° C. Specific binding was detected by incubation for 45 min at room temperature with a 1:1000 dilution of secondary Abs conjugated to ALEXAFLUOR™ dyes (568: red, 488: green, Molecular Probes).

Immunohistochemistry:

Brains were frontally sliced in a vibratome into 50 µm coronal sections encompassing the prefrontal cortex region (from Bregma 2.0 to 1.3). Sequential slices were processed for floating-section double immunohistochemistry for the detection of parvalbumin and GAD67. Antigen retrieval was performed by incubation of the slices in 1% sodium borohydride for 15 min as described (see reference 34, below), followed by washing in PBS and incubation in 10% normal goat serum in PBS for 16 h at 4° C. Primary antibodies (Calbindin: 1:5000: Calretinin: 1:2000; Parvalbumin: 1:3000, all rabbit polyclonals from Swant, Bellinzona, Switzerland. GAD67: 1:1000, from Chemicon-Millipore, Temecula, Calif.) were diluted in 2% normal goat serum in PBS and applied to the slices for 18 h at 4° C., after which slices were washed in PBS and incubated in a 1:1000 dilution of ALEXAFLUOR™ (Molecular Probes, Invitrogen, Carlsbad, Calif.) conjugated goat anti-rabbit (568) or goat anti-mouse (488) antibodies for 1 hr at room temperature (rt). Slices were washed in PBS and mounted sequentially in glass slides using VECTASHIELD™ (Vector Laboratories, Burlingame, Calif.), covered with a coverslip and allowed to dry for at least 24 h before confocal imaging.

Confocal Microscopy and Image Analysis:

Mounted slices or coverslips were evaluated for fluorescence under settings for 568 and 488 emissions on a LSM510 META™ multiphoton laser confocal microscope (Karl Zeiss, Inc.) using a 10×-PLANAPO™ objective (for slices) or a 40× water immersion objective (for coverslips). Ethidium fluorescence, the DHE oxidation product, was obtained using Ex λ 543 nm, Em λ>590 nm. For slice imaging, each slice was imaged across the prelimbic and infralimbic regions between Bregmas 1.3 and 2.0 (three images per slice). Six slices were analyzed per animal. For each slice a z-stack of 8 images was obtained (corresponding to 1.4 µm on the z-axis) for a total of 144 images per animal. All PV-neurons in the images were analyzed for their parvalbumin and GAD67 content.

Image analysis of the neuronal population in primary cultures was essentially as described (10). Briefly, coverslips are scanned to obtain 200-400 neurons (approx. 26-30 images captured per coverslip per condition using a 40× water immersion objective). Each image analyzed consists of a stack of 16 0.2 μm Z-stage images taken from the base of the neurons and across 3.2 μm depth. When analyzing PV-interneurons in particular, the coverslips are scanned to obtain images as before but for all the PV-interneurons in the coverslip.

The settings of the confocal microscope were maintained constant for each series of experiments so that the resulting images could be analyzed by densitometry and the treatment-dependent changes in fluorescence compared and expressed as % of untreated (saline) conditions. Images were then analyzed for their somatic median green and red fluorescence content using METAMORPH™ (Molecular Devices, Sunnyvale, Calif.). The median fluorescence/cell was then averaged across all imaged slices of the same animal (or experiment in the case of primary cultures in coverslips), and the mean fluorescence intensity/cell/animal was then expressed as percent of control (saline) conditions.

Statistical Analysis.

All values obtained per experiment were analyzed by one-way analysis of variance (ANOVA) followed by Tukey's post-hoc test with alpha 0.05 using SIGMASTAT™ software (Aspire Software International, Ashburn, Va.).

Example 1 Cited References

1. J. T. Coyle, Cell Mol Neurobiol 26, 365 (2006).
2. R. Takahata, B. Moghaddam, Neuropsychopharmacology 28, 1117 (2003).
3. J. D. Jentsch et al., Science 277, 953 (1997).
4. S. M. Cochran, M. Fujimura, B. J. Morris, J. A. Pratt, Synapse 46, 206 (2002).
5. B. A. Morrow, J. D. Elsworth, R. H. Roth, Psychopharmacology (Berl) (2007).
6. D. A. Lewis, G. Gonzalez-Burgos, Nat Med 12, 1016 (2006).
7. M. Bartos, I. Vida, P. Jonas, Nat Rev Neurosci 8, 45 (2007).
8. A. I. Gulyas, M. Megias, Z. Emri, T. F. Freund, J Neurosci 19, 10082 (1999).
9. J. H. Goldberg, R. Yuste, G. Tamas, J Physiol 551, 67 (2003).
10. J. W. Kinney et al., J Neurosci 26, 1604 (2006).
11. R. S. Jones, E. H. Buhl, Neurosci Lett 149, 35 (1993).
12. S. Xia et al., Neurobiol. Dis. 9, 282 (2002).
13. D. Y. Zuo et al., Pharmacol Biochem Behav 86, 1 (2007).
14. Y. Noda, K. Yamada, H. Furukawa, T. Nabeshima, Eur J Pharmacol 286, 291 (1995).
15. Mimics (2006) Biol Psychiatry 60, 163.
16. K. Q. Do et al., Eur J Neurosci 12, 3721 (2000).
17. J. K. Yao, S. Leonard, R. Reddy, Dis Markers 22, 83 (2006).
18. K. T. Kishida, E. Klann, Antioxid Redox Signal 9, 233 (2007).
19. K. L. Quick, L. L. Dugan, Annals Neurology 49, 627 (2001).
20. K. L. Quick et al., Neurobiol Aging Epub ahead of print. (2006).
21. S. S. Ali et al., Free Radic. Biol. Med. 37, 1191 (2004).
22. Infanger, et al., Antioxid Redox Signal 8, 1583 (2006).
23. B. A. Hart, J. M. Simons, Biotechnol Ther 3, 119 (1992).
24. P. D. Butler, D. C. Javitt, Curr Opin Psychiatry 18, 151 (2005).
25. M. Hajos, Trends Pharmacol Sci 27, 391 (2006).
26. D. Trotti, et al., Nat. Neurosci. 2, 427 (1999).
27. A. K. Mustafa et al., Proc Natl Acad Sci USA 104, 2950 (2007).
28. G. Kohr, S. Eckardt, H. Luddens, H. Monyer, P. H. Seeburg, Neuron 12, 1031 (1994).
29. S. A. Lipton et al., Trends Neurosci 25, 474 (2002).
30. B. Thorne, S. Wonnacott, P. R. Dunkley, J Neurochem 56, 479 (1991).
31. V. Heidinger et al., J Neurosci 22, 5452 (2002).
32. M. T. Quinn, M. C. Ammons, F. R. Deleo, Clin Sci (Lond) 111, 1 (2006).
33. Goldstein, et al., Antioxid Redox Signal 7, 1021 (2005).
34. D. P. Stanley, A. K. Shetty, J Neurochem 89, 204 (2004).

Example 2

Compositions and Methods of the Invention are Effective in the Amelioration of Pathology in the Brain Caused or Mediated by IL-6, NADPH Oxidase and SOD Enzymes This example demonstrates that the compositions and methods of the invention are effective in the amelioration of pathology in the brain caused or mediated by IL-6, IL-6-R, NADPH oxidase, and superoxide and/or hydrogen peroxide production by a NADPH oxidase, including for example schizophrenia, psychosis, delirium, e.g., post-operative delirium, drug-induced psychosis, psychotic features associated with frailty syndrome (FS), aging, depression, dementias, traumatic war neurosis, post traumatic stress disorder (PTSD) or post-traumatic stress syndrome (PTSS).

Figure 9:
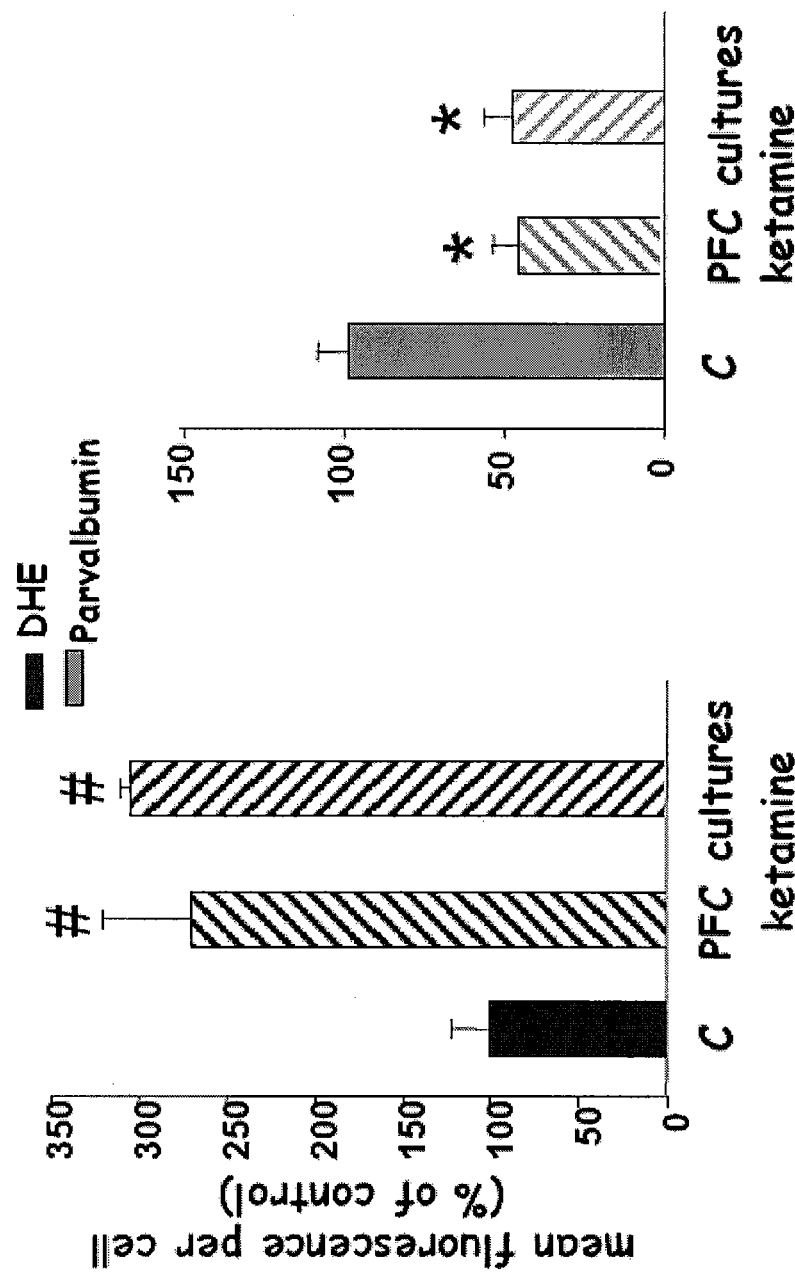
FIG. 9 left and right panels graphically illustrate data demonstrating that ketamine exposure induced a pronounced increase in DHE oxidation both in vivo (in the prefrontal cortex, PFC) and in cultures, as described in detail in Example 1, below; see also explanation for FIGS. 1 and 4.

Ketamine exposure induced a pronounced increase in DHE oxidation both in vivo (in the prefrontal cortex, PFC) and in cultures, as illustrated by the data presented schematically in FIG. 9. Male C57BL/6J were treated with ketamine; 30 mg/kg i.p on two consecutive days, and sacrificed 18 h after the last ketamine injection. Dihydroethidium (DHE) was applied ½ hour after the last ketamine injection. DIV 21 cortical neuronal cultures were treated with ketamine (0.5 μM) for 24 h, and exposed to DHE 1 μg/ml for the last hour. PFC coronal sections and primary cultured neurons were analyzed for DHE fluorescence and parvalbumin immunoreactivity as described herein. In both cases the secondary antibody used was ALEX-AFLUOR488™ (Molecular Probes, Invitrogen, Carlsbad, Calif.) conjugated. Images were obtained using a Zeiss confocal microscope with the laser at a maximum of 10% power. DHE fluorescence was exited at 543 nm and analyzed with a cutoff filter at >570 nm. Under these conditions, fluorescence analysis for parvalbumin and DHE could be used for quantification. #,*=statistically significant compared to control with $P<0.001$ as analyzed by ANOVA followed by Tukey's test; n=6 animals/condition, or 5 cultures/condition for PFC and cultures, respectively.

Figure 10:
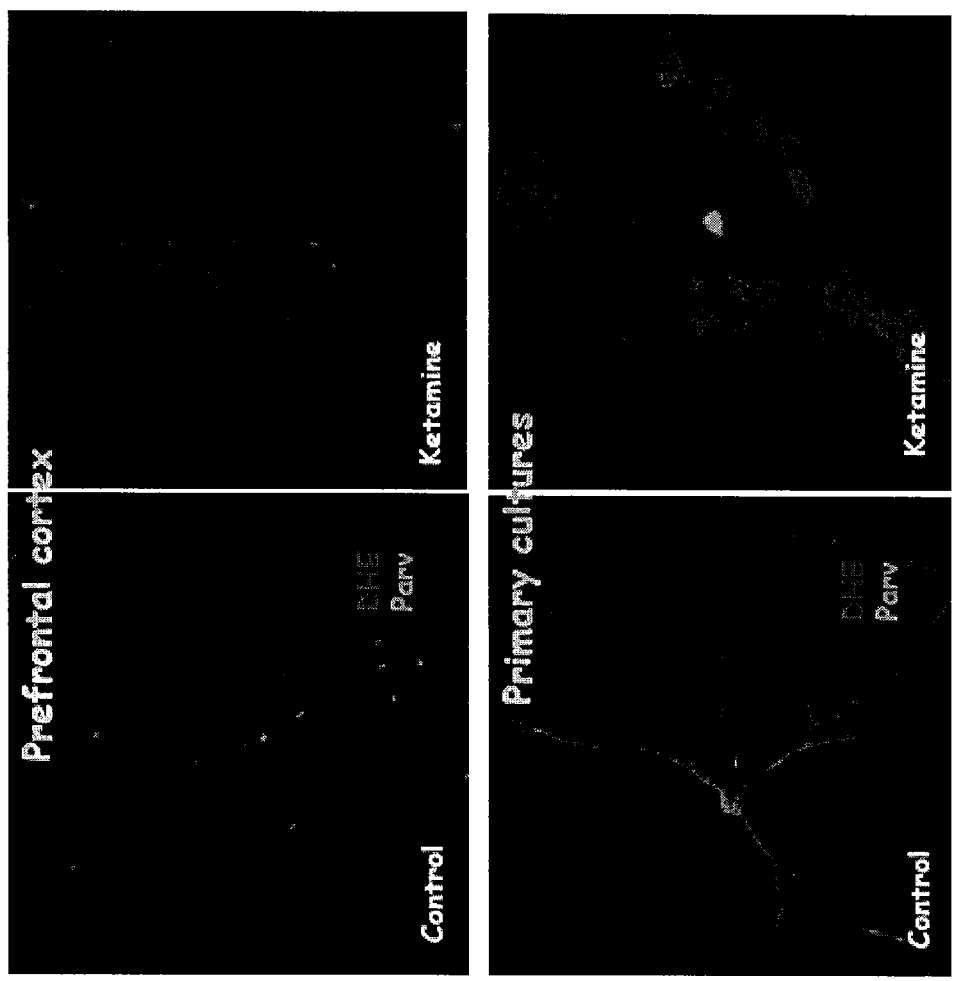
FIG. 10 all four panels illustrate representative confocal images from the experiments illustrated in FIG. 9, as described in detail in Example 2, below.

The increase in ROS was widespread and not restricted to specific neuronal populations, as illustrated in FIG. 10, which illustrates confocal images showing that ketamine induces ROS in vivo and in vitro. FIG. 10 illustrates representative confocal images from the experiments described in FIG. 9. The prefrontal cortex region analyzed corresponds to the prelimbic and infralimbic regions. Note that DHE fluorescence was not restricted to the PV-subpopulation of interneurons either in vivo or in the neuron culture system.

This increase in ROS production appears to be related to the disinhibition of cortical circuitry as was described for rodents and non-human primates upon exposure to the NMDA-receptor antagonists, phencyclidine and MK801. To analyze this possibility, primary neuron cultures were exposed to ketamine in the presence of the pan-GABA$_{(A)}$ agonist muscimol (10 μM). Under these conditions, we observed a complete block of ROS production and preservation of PV and GAD67 expression in PV-interneurons, these data graphically illustrated in FIG. 11. These results confirm that the initial event upon ketamine exposure is a disinhibition of the system.

Figure 11:
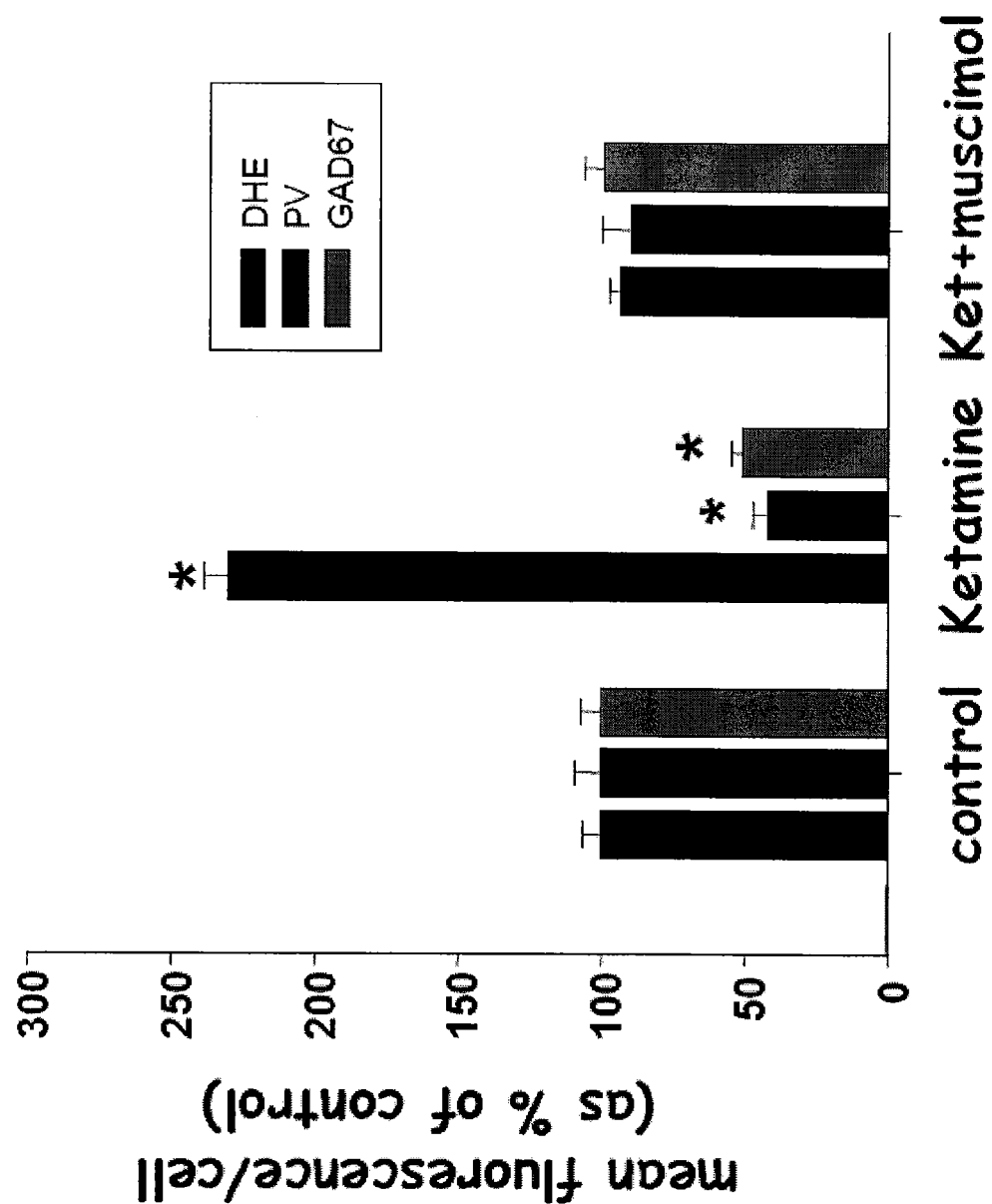
FIG. 11 graphically illustrates data from primary cultures exposed to ketamine in the presence of the pan-$GABA_{(A)}$ agonist muscimol (10 µM), as described in detail in Example 1, below; see also explanation for FIG. 5.

Co-exposure with muscimol prevents ketamine-mediated increase in ROS and loss of parvalbumin and GAD67 immunoreactivity; as shown by the data summarized in FIG. 11. Primary cultures were exposed to ketamine for 24 h as before in the absence or presence of the $GABA_{(A)}$ agonist muscimol (10 μM). This concentration was chosen from previous observations for its anti-apoptotic effects in this system. Sister coverslips were treated similarly and DHE was added for the last hour of treatment. Fixation and immunostaining was as described before. GAD67 and parvalbumin immunoreactivity was quantified as described by Kinney (2006) J. Neurosci. 26:1604. *=Statistically significant with respect to control at P<0.001 by ANOVA followed by Tukey's test. N=4 experiments per condition.

Furthermore, these results also demonstrated that this disinhibition may have caused increased ROS. Of note, in primary cultures "disinhibition" can only mean increased glutamate, since by definition, these cultures lack neuronal inputs from outside the cortex.

It was next determined whether superoxide generation by ketamine exposure was due to activation of NADPH oxidase. The effects of a Nox inhibitor, apocynin, and a SOD-mimetic ($C_3$) were analyzed. Exposure of primary neuronal cultures to ketamine in the presence of $C_3$ prevented the increase in ROS. More importantly, the Nox inhibitor apocynin also prevented the increase in free radical production, as shown by the data summarized in FIG. 12, demonstrating that activation of Nox is involved in the generation of superoxide upon administration of NMDA-receptor antagonists.

Figure 12:
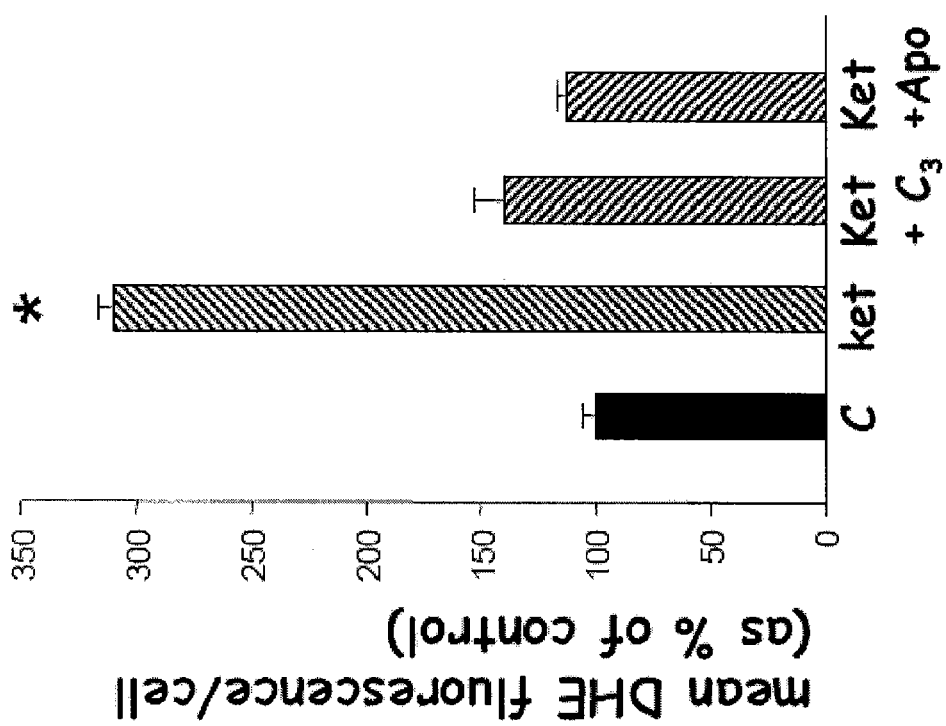
FIG. 12 graphically illustrates data demonstrating that a SOD mimetic ($C_3$), or the Nox inhibitor apocynin (Apo) prevented ketamine-mediated superoxide and/or hydrogen peroxide production in cultures, as described in detail in Example 1, below; see also explanation for FIG. 2.

Data summarized in FIG. 12 demonstrates that a SOD mimetic ($C_3$), or the Nox inhibitor apocynin (Apo) prevented ketamine-mediated superoxide and/or hydrogen peroxide production in cultures. Cultures were treated with ketamine as before in the absence or presence of 1 μM C3 or 500 μM apocynin for 24 h. DHE was added during the last hour of treatment. Cells were fixed as before and DHE fluorescence was analyzed by confocal microscopy. *=significantly different from control at P<0.001 by ANOVA followed by Tukey's test. N=4 experiments per condition.

Figure 13:
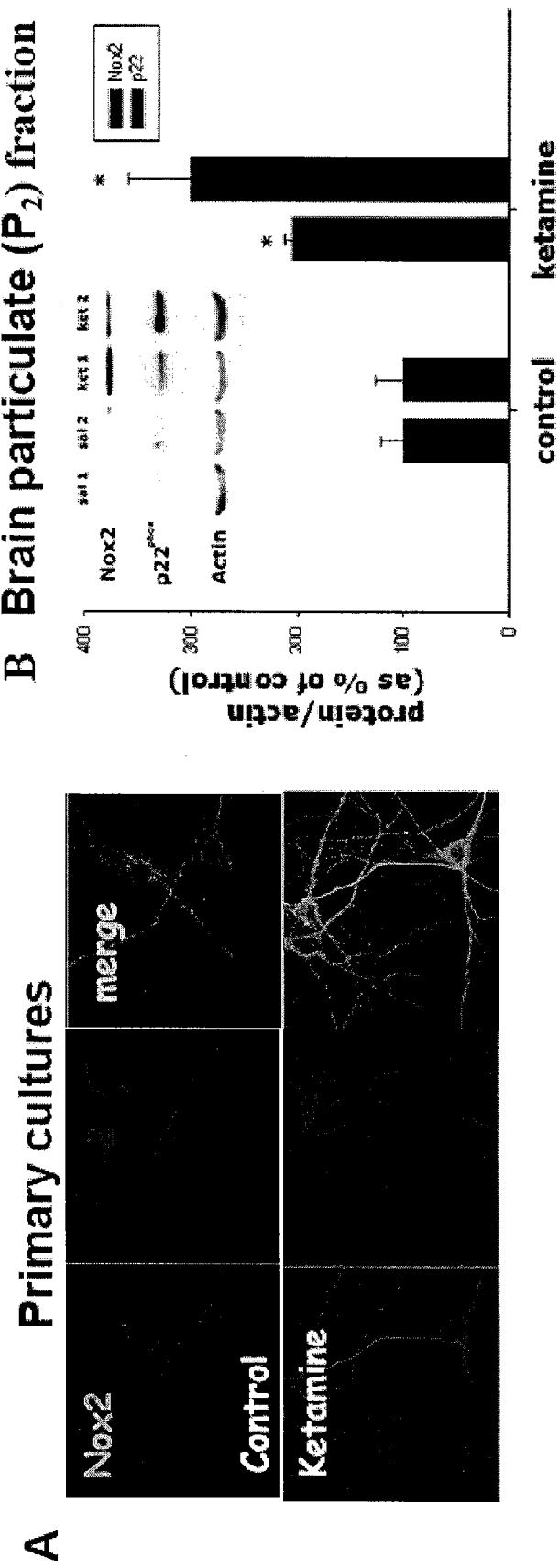
FIG. 13 in images and graphics illustrates data showing that Nox2 is expressed in cortex and ketamine treatment increased its expression in vitro and in vivo; ketamine treatment increased the expression of Nox2 in cultures, as shown in the confocal images of the six panels of FIG. 13A; and also increased Nox2 and $p22^{phox}$ in cortical particulate fractions from ketamine treated animals, as graphically shown in FIG. 13B; the inset illustrating Western blots of levels of the indicated proteins in the various samples, as described in detail in Example 1, below; see also explanation for FIGS. 3 and 6.

We next analyzed the expression of Nox isoforms and subunits and found that cultures express mRNA for Nox2, Nox4, and $p22^{phox}$, but not Nox1, Nox3 or Nox5 (data not shown). Expression of Nox2 and $p22^{phox}$ protein was confirmed by Western blot and ICC, as illustrated in FIG. 13, and was increased by ketamine. We did not see changes in Nox4 expression after ketamine treatment (not shown). Since only Nox2, but not Nox4 is inhibitable by apocynin at the concentrations used in our studies, this demonstrates that Nox2 is the isoform responsible for ketamine-mediated ROS, a result that can be confirmed in $gp91^{phox}$-/- mice.

Data illustrated in FIG. 13 shows Nox2 is expressed in cortex and ketamine treatment increased its expression in vitro and in vivo. Ketamine treatment (0.5 μM, 24 h) increased the expression of Nox2 in cultures FIG. 13A and also increased Nox2 and $p22^{phox}$ in cortical particulate fractions from ketamine treated animals FIG. 13B.

Use of Synaptosomal Preparations from Ketamine Treated Animals to Study the Regulation of Nox Activity.

Synaptosomes, isolated nerve terminals whose axonal attachments have been severed by shear stress during homogenization, were used because they are a simple mammalian neuronal model in which functional cell-like environments are physiologically maintained. In a synaptosome, mitochondria are present and supplied with substrates by the metabolic-machinery such that they produce ATP. Synaptosomal membranes retain ion pumps and channels as well as the components necessary for synaptic vesicle exocytosis and recovery, and changes occurring in vivo are maintained in the isolated synaptosomal fractions.

We employed synaptosomal membrane preparations to study neuronal ROS production and to identify contributions by mitochondria and Nox isoforms. We also employed polarographic electrochemical determination of Nox activity through NADPH-dependent oxygen consumption by synaptosomes, and followed the parallel production of ROS by synaptosomes using EPR spin-trapping spectroscopy. We assayed NADPH oxidase activity by following NADPH-dependent $O_2$ consumption in the presence of Nox inhibitors.

Figure 14A:
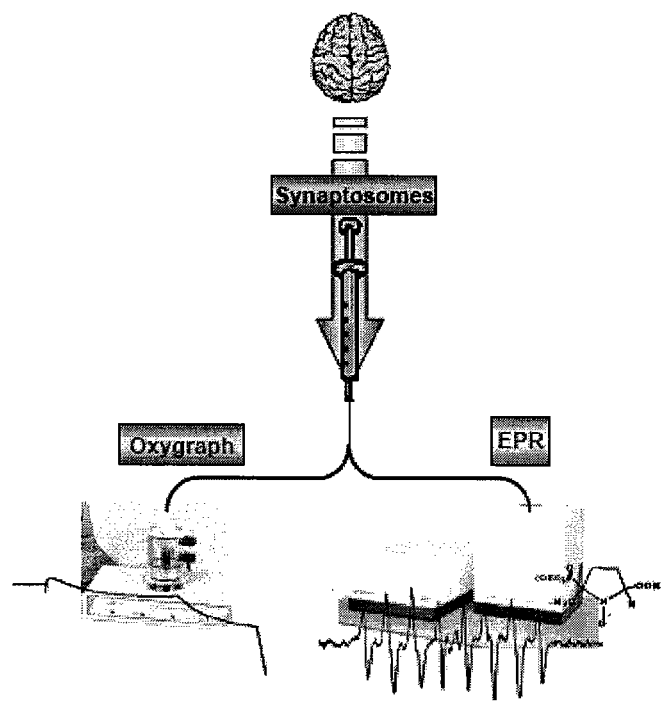
FIG. 14A illustrates schematically an exemplary experimental scheme using synaptosomes, and FIG. 14B, which graphically summarizes data showing dose-dependent inhibition of NADPH-stimulated $O_2$ consumption by apocynin; inset of FIG. 14B graphically illustrates inhibition of Nox by apocynin; as described in detail in Example 1, below; see also explanation for FIG. 7.

FIG. 14A illustrates the experimental scheme where synaptosomes are isolated from mice brain cortex and split into two portions that are transferred to the oxygraph chamber, where oxygen consumption is monitored at different conditions; or to the EPR spectrometer to spin-trap and evaluate.

Figure 14B:
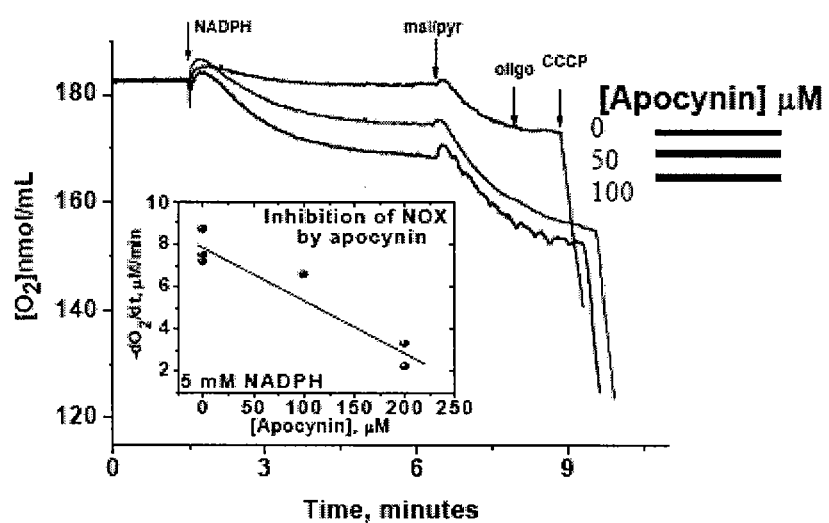

Consumption of oxygen by NOX and inhibition by apocynin is illustrated in the data summarized in FIG. 14B, which summarizes data showing dose-dependent inhibition of NADPH-stimulated $O_2$ consumption by apocynin; 200 μM apocynin was sufficient to block>90% of NADPH-induced $O_2$ consumption (compare blue and black traces, and see inset). Comparing the three oxygraph traces in FIG. 14B indicates that inclusion of apocynin did not affect mitochondrial respiration or by inference, any of the electron transport components. In FIG. 14B, approximately 5 mg synaptosomal protein was incubated for 10 minutes at 37° C. with 200 μM digitonin and different apocynin concentrations (0-200 μM) before the activation of NOX was triggered by the addition of 5 mM NADPH. Viability of synaptosomal mitochondria in the presence of digitonin and apocynin was assessed by respiration upon the addition of 10 mM malate and 10 mM pyruvate. $F_0F_1$-ATPase inhibitor oligomycin (4 μg/mL) halted oxygen consumption and the maximal mitochondria uncoupling was established by the addition of 0.5 μM CCCP as an indication of 'healthy mitochondria".

EPR Spectroscopy on Synaptosomal Preparations.

EPRS was used to measure ROS production by synaptosomes. For each preparation, 10 mg synaptosomal protein was mixed with 100 mM of the DIPPMPO spin-trap and the EPR spectra were recorded after 1 hr in the absence or in the presence of Nox and/or mitochondrial substrates, c.f. all spectra in FIG. 15. Nitrone spin traps react with short-lived transient radical species to form more stable nitroxide free radical adducts that are easy to detect by EPRS. The signal can be interpreted through computer simulations to resolve contributions from different radical species. The peak-heights or area-under-peak are parameters that depend on experimental conditions and the concentration of the free radical species detected. By fixing various experimental and spectral conditions, we obtained EPR signals that correlate with free radical concentrations. Data demonstrated a 4-fold enhancement of the EPR signal in synaptosomes after addition of NADPH, demonstrating that $O_2$. signal (marked by *) derives from NADPH oxidase. The source of $O_2$. was further defined by showing that it was blocked by apocynin and did not derive from mitochondria. Taken together, these results indicate the presence of Nox-associated $O_2$. production in synaptosomes.

Figure 15:
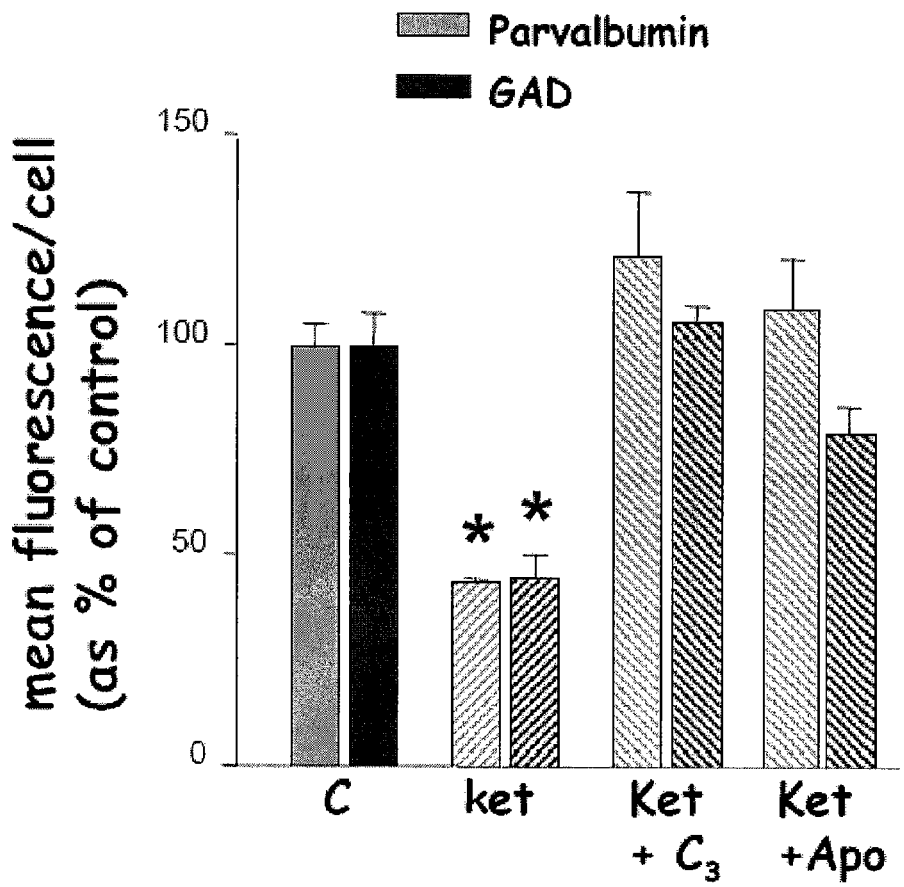
FIG. 15 schematically illustrates data showing that SOD mimetic and apocynin prevented ketamine effects on PV-interneurons in culture; as described in detail in Example 1, below; see also explanation for FIG. 2.

The SOD mimetic and apocynin prevented ketamine effects on PV-interneurons in culture, these data are summarized in FIG. 15. Cultures were treated with ketamine for 24 h in the absence or presence of C3 or apocynin. After fixation, quantitative parvalbumin and GAD67 ICC was carried out. *=statistically significant at P<0.05 as compared to control conditions by ANOVA followed by Tukey's test. N=4 experiments per condition.

Synaptosomal Nox is an Active Source of Free Radicals.

Figure 16:
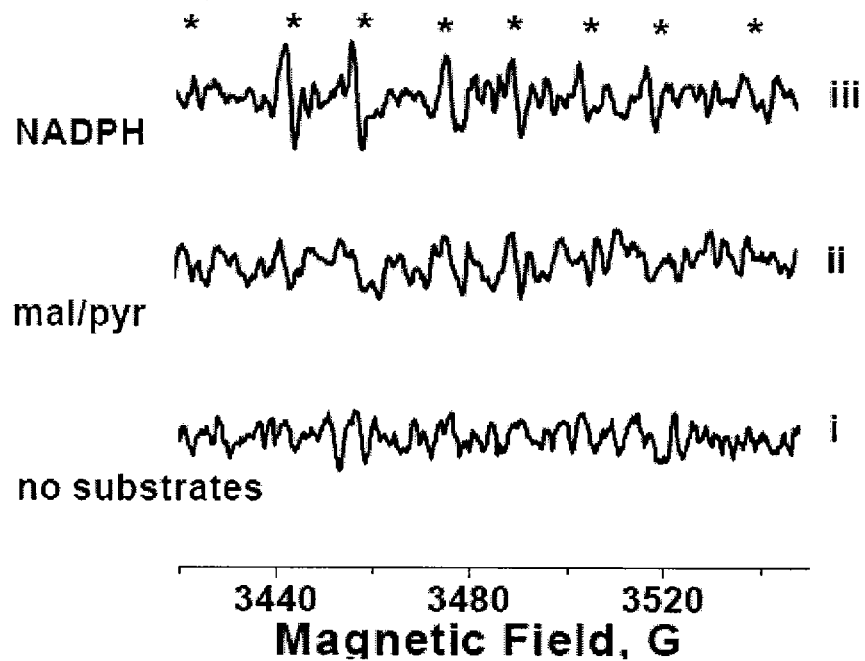
FIG. 16 illustrates data showing that synaptosomal Nox is an active source of free radicals: EPR spectra recorded after 1 hr incubation of approximately (~) 10 mg synaptosomal protein isolated from mouse brain at 37° C. in the absence of Nox or mitochondria substrates is shown in FIG. 16(*i*), in the presence of 10 mM malate+10 mM pyruvate is shown in FIG. 16 (*ii*), or 200 mM digitonin+5 mM NADPH is shown in FIG. 16(*iii*); as described in detail in Example 1, below; see also explanation for FIG. 7.

EPR spectra recorded after 1 hr incubation of approximately (~) 10 mg synaptosomal protein isolated from mouse brain at 37° C. in the absence of Nox or mitochondria substrates is shown in FIG. 16($i$), in the presence of 10 mM malate+10 mM pyruvate is shown in FIG. 16 (ii), or 200 mM digitonin+5 mM NADPH is shown in FIG. 16($iii$). The observed signals are arising from DIPPMPO/superoxide adduct and matches that reported by Chalier & Tordo (2002) J. Chem. Soc., Perkin Trans. 2, 2110-2117. The mixture was injected into the EPR cavity of Bruker e-scan benchtop spectrometer via a Teflon tube with inner diameter of ~0.4 mm. The EPR settings were, receiver gain 1×103, scan width 200 G centered at 3484.9 G, modulation amplitude 4 G, time constant 5.16 ms, modulation frequency 86 kHz, microwave power 5.04 mW, 5.24-s sweep time, and the spectrometer's operating frequency 9.784 GHz. Each spectrum was the average of 200-times accumulations.

Having characterized the activity of Nox in synaptosomes, we proceeded to analyze the activity of the enzyme in synaptosomal fractions obtained from ketamine-treated animals. Mice were treated with either saline or ketamine (30 mg/kg) (4/group) on two consecutive days and sacrificed 18 h after the last ketamine injection. Brains were immediately extracted and synaptosomes prepared as described above and analyzed for Nox activity. Ketamine treatment in vivo induced a pronounced increase in Nox activity in synaptosomes which was inhibited by apocynin. Most importantly, increased Nox activity did not affect mitochondrial function in synaptosomes, at least during the period of the experiment.

Involvement of Nox Activation in the Loss of Phenotype of PV-Interneurons.

To further analyze the mechanism by which Nox is activated upon ketamine treatment, and the possibility that superoxide derived from activation of Nox is involved in the loss of GABAergic phenotype of PV-interneurons, we analyzed the effects of the SOD-mimetic C3 and the Nox inhibitor apocynin on the effects of ketamine in parvalbumin and GAD67 immunoreactivity in the primary culture system. Preventing superoxide generation with apocynin, or inducing its dismutation with the SOD-mimetic attenuated the decrease in parvalbumin and GAD67 expression in PV-interneurons in culture. These demonstrated involvement of Nox activation in ketamine effects on PV-interneurons.

To confirm these results in vivo, mice were treated with ketamine in the absence or presence of either apocynin or the brain-permeable SOD mimetic ($C_3$). Ketamine reduced parvalbumin and GAD67 expression in the PFC, see FIG. 17, left. Treatment with $C_3$ or apocynin prevented the loss of parvalbumin in PV-interneurons and reduced DHE oxidation, see FIG. 17, right. Furthermore, treatment with $C_3$ actually increased the expression of the calcium-binding protein above control levels, a result we had already observed in the culture system.

Figure 17:
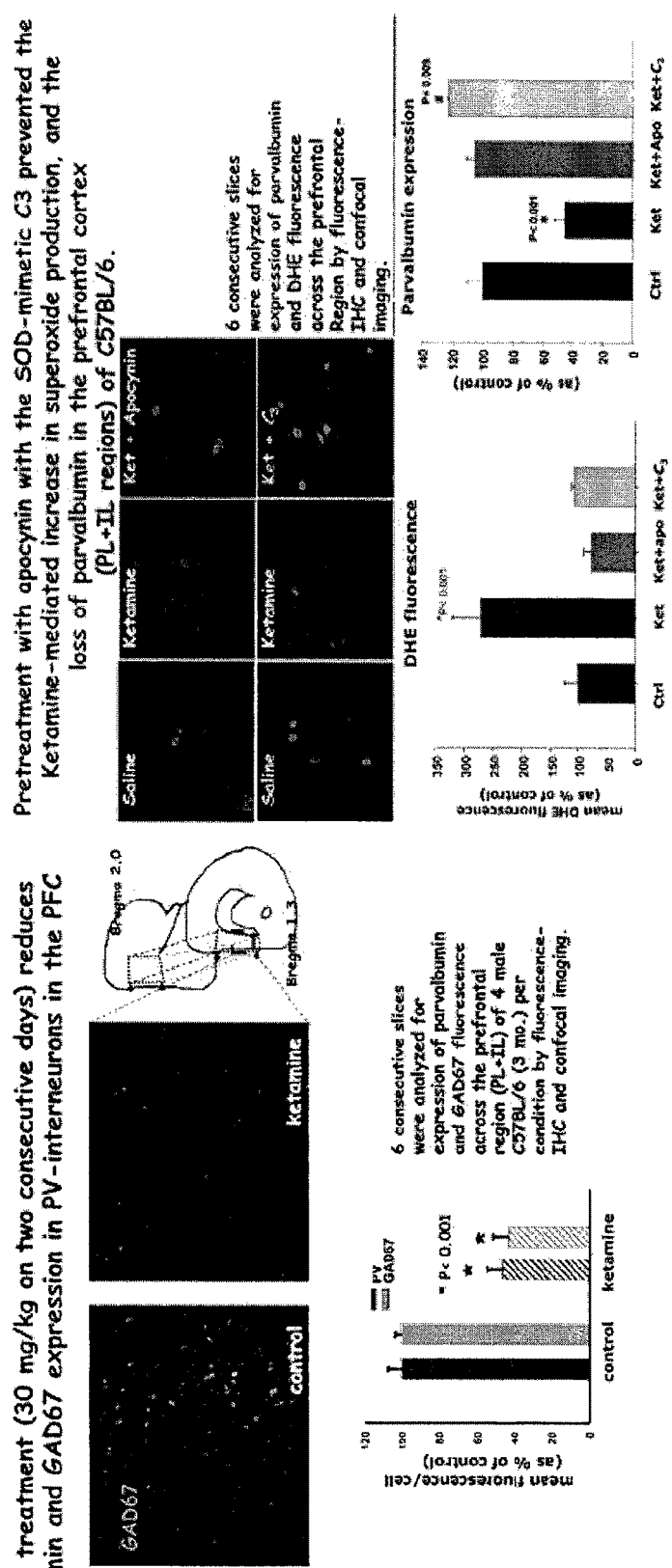
FIG. 17 illustrates data schematically and by image showing involvement of Nox activation in ketamine effects on PV-interneurons in vivo, where mice were treated with ketamine in the absence or presence of either apocynin or the brain-permeable SOD mimetic ($C_3$), and ketamine reduced parvalbumin and GAD67 expression in the PFC, as illustrated in FIG. 17, left two confocal images and graphic data summary; and treatment with $C_3$ or apocynin prevented the loss of parvalbumin in PV-interneurons and reduced DHE oxidation, as illustrated in FIG. 17, right six confocal images and two graphic data summaries; as described in detail in Example 1, below; see also explanation for FIG. 4.

FIG. 17 (Left panel): Animals were treated with ketamine (30 mg/kg. ip) applied on two consecutive days and sacrificed 18 h after the last ketamine injection. Coronal sections comprising the PFC (Bregma 2.0-1.3) were analyzed for parvalbumin and GAD67 expression in PV-interneurons as described in Methods. FIG. 17 (Right panel): Animals were treated with apocynin in the drinking water for 1 week before the treatment with ketamine, or during one month with the SOD-mimetic $C_3$ delivered by mini-pumps. and DHE was injected 30 mM after the last ketamine application. The animals were deeply anesthetized, and perfusion fixed as described in the methods section. Coronal sections encompassing the prefrontal region were processed for IHC and analyzed for parvalbumin expression and DHE fluorescence. N=5-6 animals per condition. * and # indicates statistical significance with respect to control at the indicated P values as analyzed by ANOVA followed by Tukey's multiple comparisons test. Enlarged images are provided in the appendix section.

Role of the Pro-Inflammatory Cytokine Interleukin-6 in the Ketamine-Mediated Increase of Nox Expression, Superoxide and/or Hydrogen Peroxide Production, and Loss of Phenotype of PV-Interneurons.

Treatment with NMDA receptor antagonists has been shown to increase IL-6 in plasma, and plasma levels of IL-6, in turn, correlate with the degree of psychosis in schizophrenia patients. Therapeutic use of IL-6 for solid tumors also induces psychosis, and interestingly, mice that overexpress IL-6 under the GFAP promoter demonstrate a loss of PV-interneurons. Since pro-inflammatory cytokines, such as TNFα, IL-1β, and IL-6 are known to activate NFκB, and NFκB can regulate expression of both Nox2 and p22$^{phox}$, we tested the possibility that IL-6 could induce Nox in vitro and in vivo, and further asked whether IL-6 might be a mediator in the ketamine-induced Nox expression and loss of phenotype of the PV-immunoreactive GABAergic interneurons.

Figure 18:
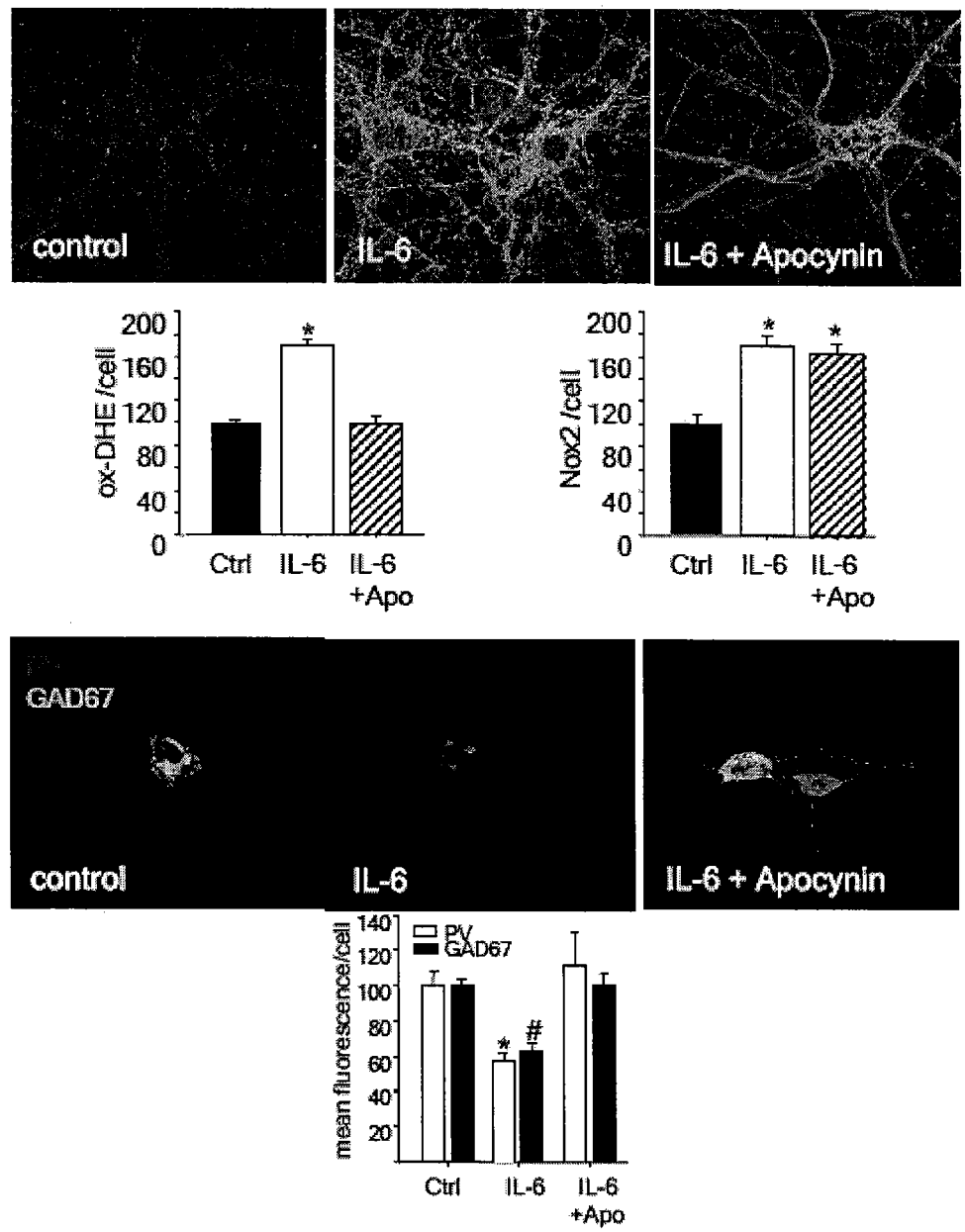
FIG. 18 illustrates data showing that IL-6, when applied for 24 h, increased the levels of Nox expression and DHE oxidation (top panels) and decreased the immunoreactivity of GAD67 and parvalbumin (bottom panels), and these effects were prevented by the Nox inhibitor apocynin, as described in detail in Example 2, below.

IL-6 increases superoxide in a Nox dependent manner, and reduces GAD67 and parvalbumin in primary cultures, as summarized by the data graphically presented in FIG. 18. Cultures were treated with IL-6 (10 ng/ml) for 24 h in the absence or presence of apocynin (500 mM). As before, dihydroethidium (DHE) was applied for the last hour (DHE detects superoxide and hydrogen peroxide). After fixation, ICC for PV and GAD67 was carried out as described in methods and quantitative confocal microscopy was utilized for fluorescence analysis.

We treated primary neuronal cultures with IL-6 (10 ng/ml), a concentration shown to modulate the activity of cortical neuronal cultures, and analyzed superoxide and/or hydrogen peroxide production as well as immunoreactivity for parvalbumin and GAD67 in PV-interneurons. IL-6, when applied for 24 h, increased the levels of DHE oxidation and decreased the immunoreactivity of GAD67 and parvalbumin, and these effects were prevented by the Nox inhibitor apocynin, as summarized in FIG. 18 (left).

To confirm that IL-6 mediates the increase in Nox2, we analyzed Nox2 expression by immunocytochemistry and its activity by determination of oxidized dihydroethidium (oxDHE). Primary cortical neurons exposed to IL-6 for 24 hours showed a pronounced increase in the expression of Nox2, as well as an increase in superoxide production (FIG. 18, left). The superoxide production was eliminated when apocynin was added along with IL-6, whereas Nox2 induction by IL-6 was not affected by the oxidase inhibitor. These results demonstrate that IL-6 is the downstream mediator of ketamine in the induction of Nox2.

The data of FIG. 18, left, demonstrates that IL-6 increases superoxide production and Nox2 expression in neurons. Neuronal cultures were treated with IL-6 (10 ng/ml) in the absence (control) or presence of the Nox2 inhibitor apocynin (0.5 mM) for 24 h. DHE (1 μg/ml) was added during the last hour of treatment. Images show the increase in Nox2 immunoreactivity and oxidized DHE upon treatment with IL-6.

Bar-graphs show the results of quantification of oxidized DHE and Nox2 fluorescence expressed as % of control. (* P<0.001 by Tukey's test. ANOVA (oxDHE): P<0.001, $F_{stat}$: $40.712_{(oxDHE)}$; $ANOVA_{(Nox2)}$: P<0.001, F: 47.570, n=5 experiments). Data are means±SEM. Baseline intensities: DHE=21±4.7; Nox2=18.7±2.6.

When the cultures were treated with IL-6, but in the presence of sub-threshold concentrations of ketamine, we found that IL-6 increased the effects of ketamine on parvalbumin and GAD67 immunoreactivity, as summarized in FIG. 18 (right). When primary neuronal cultures were exposed to IL-6 (10 ng/ml for 24 h) we observed a decrease in parvalbumin and GAD67 in PV-interneurons (FIG. 18, right), demonstrating that IL-6 is able to fully reproduce the ketamine effects we previously showed in cultured neurons. IL-6 effects on PV-interneurons were prevented by co-exposure to the NADPH oxidase inhibitor apocynin (4-hydroxy-3-methoxyacetophenone), indicating that, similar to ketamine, the interleukin effects were mediated by activation of Nox2-dependent NADPH oxidase superoxide production, as illustrated by the data of FIG. 18.

The data of FIG. 18 (right) demonstrates IL-6 exposure leads to the loss of phenotype of PV-interneurons in primary neuronal cultures. Neuronal cultures were treated with IL-6 (10 ng/ml) in the absence (control) or presence of the Nox2 inhibitor apocynin (0.5 mM) for 24 h. Fluorescence confocal images of representative fields depicting the expression of parvalbumin (PV) and GAD67 in PV-interneurons. Bar-graph represents the quantification of fluorescence expressed as % of control. (* P=0.002, # P<0.001 by Tukey's test. $ANOVA_{(PV)}$: P<0.001, F: 11.860, $ANOVA_{(GAD67)}$: P<0.001, F: 24.912. n=4 experiments). Data are means±SEM. Baseline intensities: PV=135±32; GAD67=114±26.

It is possible that IL-6 causes the activation of Nox and increase in superoxide in a fashion similar to the effects we observed for ketamine. So, in cultures we compared the effects of IL-6 and ketamine on Nox2 expression in the presence and absence of the $GABA_{(A)}$ agonist muscimol. Both ketamine and IL-6 induced expression of Nox2, but muscimol only prevented the induction of the enzyme by ketamine, as illustrated in FIG. 20, this data indicating that IL-6 is downstream of the initial disinhibition caused by ketamine treatment IL-6 Potentiates Ketamine Effects on PV-Interneurons.

Figure 19:
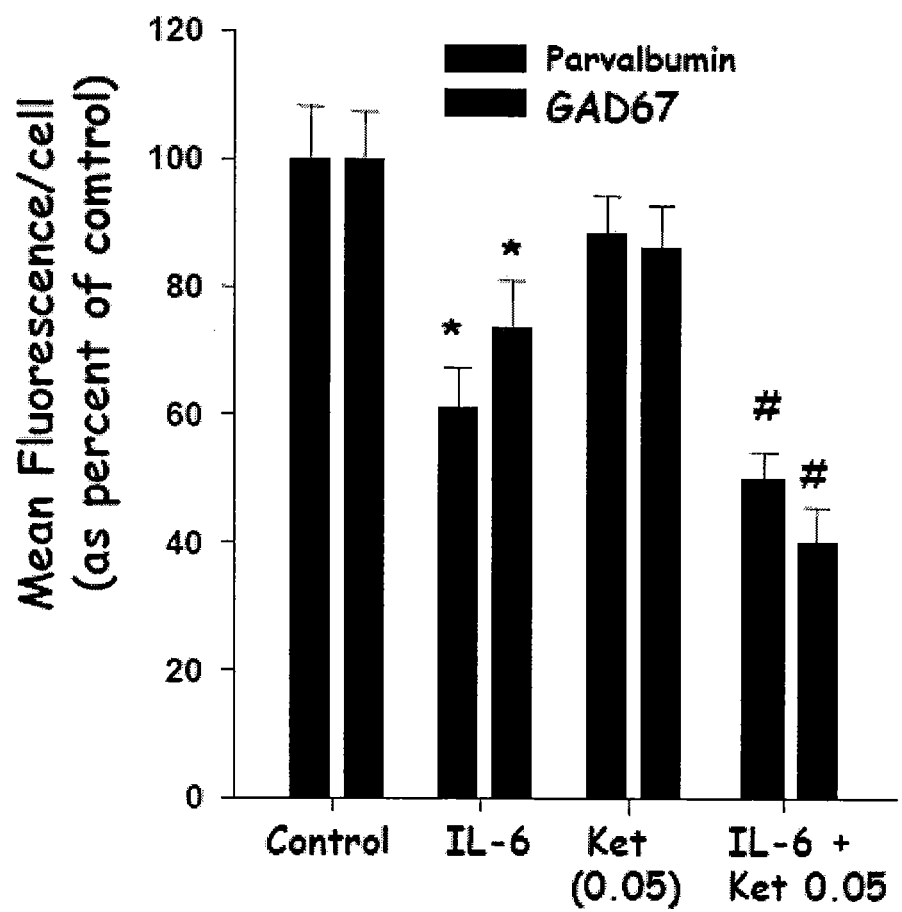
FIG. 19 schematically illustrates data showing the results of treating cultured neurons with a subthreshold concentration of ketamine in the absence or presence of IL-6, as described in detail in Example 2, below.

Cultured neurons were treated with a subthreshold concentration of ketamine (0.05 mM) in the absence or presence of IL-6 (10 ng/ml) for 24 h; this data is schematically summarized in FIG. 19. After fixation, ICC for GAD67 and parvalbumin was carried out as described by Kinney (2006) J. Neurosci. 26:1604. * indicates statistically significant with respect to control at P<0.05, and # indicates significantly different with respect to ketamine or IL-6 alone at P<0.05 by ANOVA followed by Tukey's test. N=3 cultures per condition.

Figure 20:
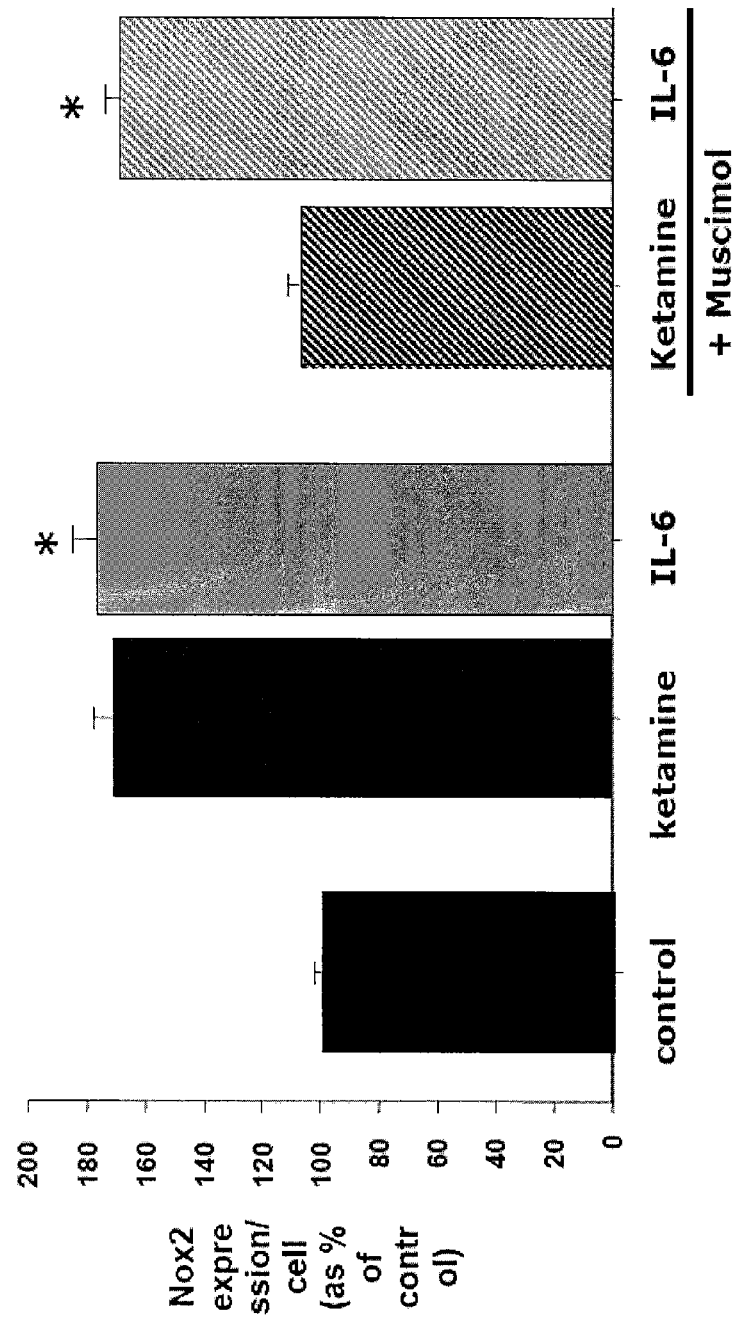
FIG. 20 schematically illustrates data showing that muscimol prevents only ketamine-mediated induction of Nox2 in primary cultures; cultures were treated with ketamine or IL-6 in the absence or presence of muscimol, as described in detail in Example 2, below.

Muscimol prevents only ketamine-mediated induction of Nox2 in primary cultures; this data is schematically summarized in FIG. 20. Cultures were treated with ketamine (0.5 µM) or IL-6 (10 ng/ml) in the absence or presence of muscimol (10 mM) for 24 h. Nox immunoreactivity was analyzed by ICC using anti-Nox and anti-MAP2 double immunofluorescence. Values are expressed as percent of control conditions (no treatment). * indicates statistical significance with respect to control conditions at p<0.05 by ANOVA followed by Tukey's test. N=200 cells across three experiments.

Figure 21:
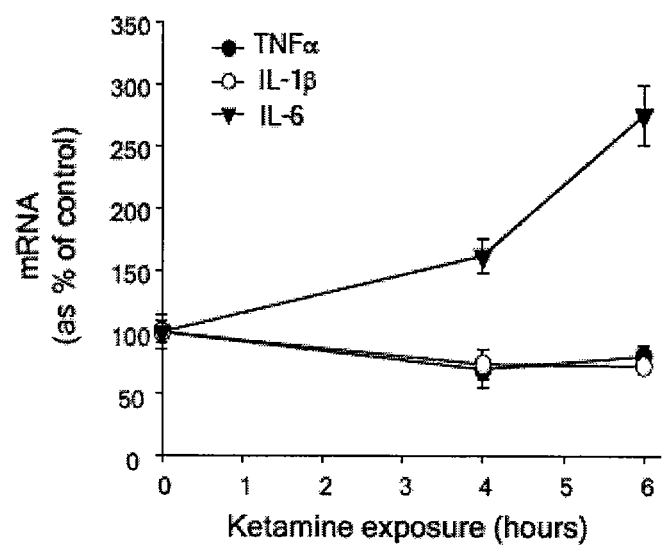
FIG. 21 schematically illustrates data showing that only IL-6 mRNA expression, but not IL-1β or TNFα, was induced by ketamine in cultures; cultures were treated with ketamine for varying periods of time and mRNA was extracted, as described in detail in Example 2, below.

We therefore tested the possibility that upon treatment with ketamine there is an induction of IL-6 expression, which would in turn be responsible for Nox induction. RT-PCR performed on RNA obtained from ketamine-treated cultures showed increased IL-6 RNA. As illustrated in FIG. 21, ketamine induced IL-6 mRNA expression in cultures. Cultures were treated with ketamine (0.5 µM) for varying periods of time and mRNA was extracted using TRIZOL™ (Invitrogen, Carlsbad, Calif.), see Methods, below. RT-PCR was performed using primers specific for murine IL-6 and for GAPDH as internal control. IL-6 mRNA was significantly increased already at 4 h of ketamine exposure. The mRNA levels decreased after 6 h to levels that were above control after 24 h.

These results led us to believe that NMDA-receptor antagonists, through inhibition of PV-interneuron function, trigger a mild inflammatory reaction in brain which increases brain IL-6 levels and therefore neuronal expression of Nox. Conversely, since increased IL-6 plasma levels are a consistent finding in schizophrenic patients, and NMDA-receptor antagonists increase plasma levels of IL-6 applied i.c.v. in rodents, we wanted to determine whether IL-6 administered peripherally intraperitoneally (i.p) would have any effect on neuronal Nox expression and/or loss of PV-interneuron phenotype. Animals were treated on two consecutive days with 5 µg/kg IL-6 or saline, and synaptosomal preparations were prepared and analyzed. We observed a significant induction of Nox activity, as illustrated in FIG. 22, demonstrating that plasma IL-6 can have CNS effects.

Figure 22:
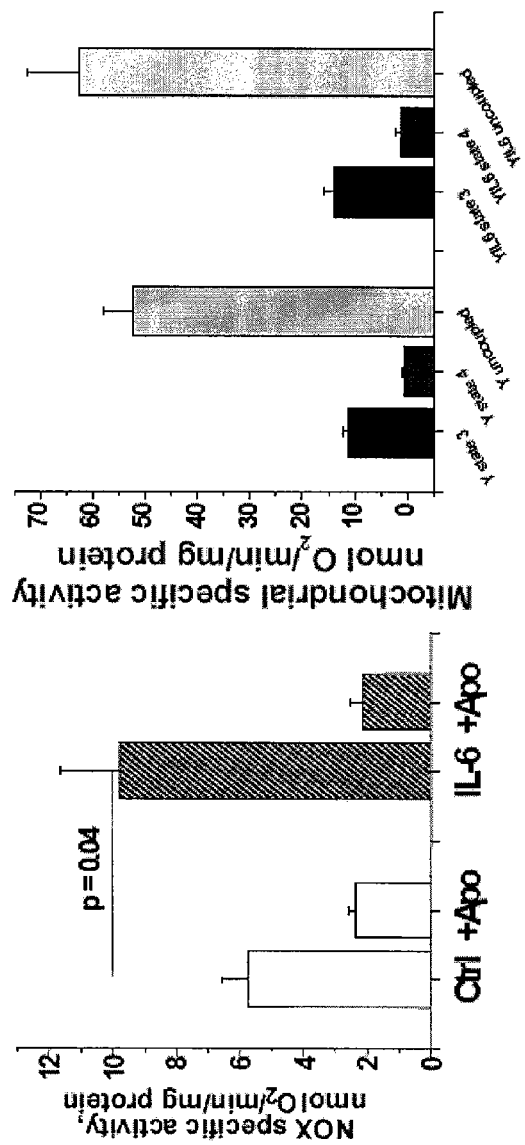
FIG. 22 schematically illustrates data showing a significant induction of Nox activity in by IL-6 in synaptosomal preparations, as described in detail in Example 2, below.

To generate the data illustrated in FIG. 22, mice (4 animals per condition) were treated with IL-6 (5 ug/kg) on two consecutive days at the same time of the day. Synaptosomes were prepared after 22 hours (h) of the last injection, NADPH-dependent oxygen consumption was analyzed in the absence or presence of apocynin, 150 uM. The apocynin effect clearly shows that as occurred with ketamine treatment, where IL-6 induces preferentially Nox2 in the brain.

We also observed increased apocynin-inhibitable DHE oxidation, and increased Nox2 expression by IHC (data not shown). The question of whether IL-6 crosses the BBB directly, or triggers secondary events which lead to Nox induction is not addressed by this experiment, although the latter is more likely based on previous studies showing that LPS administered to IL-6−/− mice fails to disrupt learning and memory, although plasma cytokine levels are high. However, these findings do demonstrate that elevated plasma IL-6 can result in the induction of brain Nox, superoxide and/or hydrogen peroxide production and loss of the GABAergic phenotype of PV-interneurons.

Behrens (2007) Science 318:1645-1647; showed that exposure to sub-anesthetic levels of ketamine on two consecutive days induces a pronounced increase in brain superoxide through activation of NADPH-oxidase, and that this leads to the loss of phenotype of PV-interneurons in prefrontal cortex.

Figure 23:
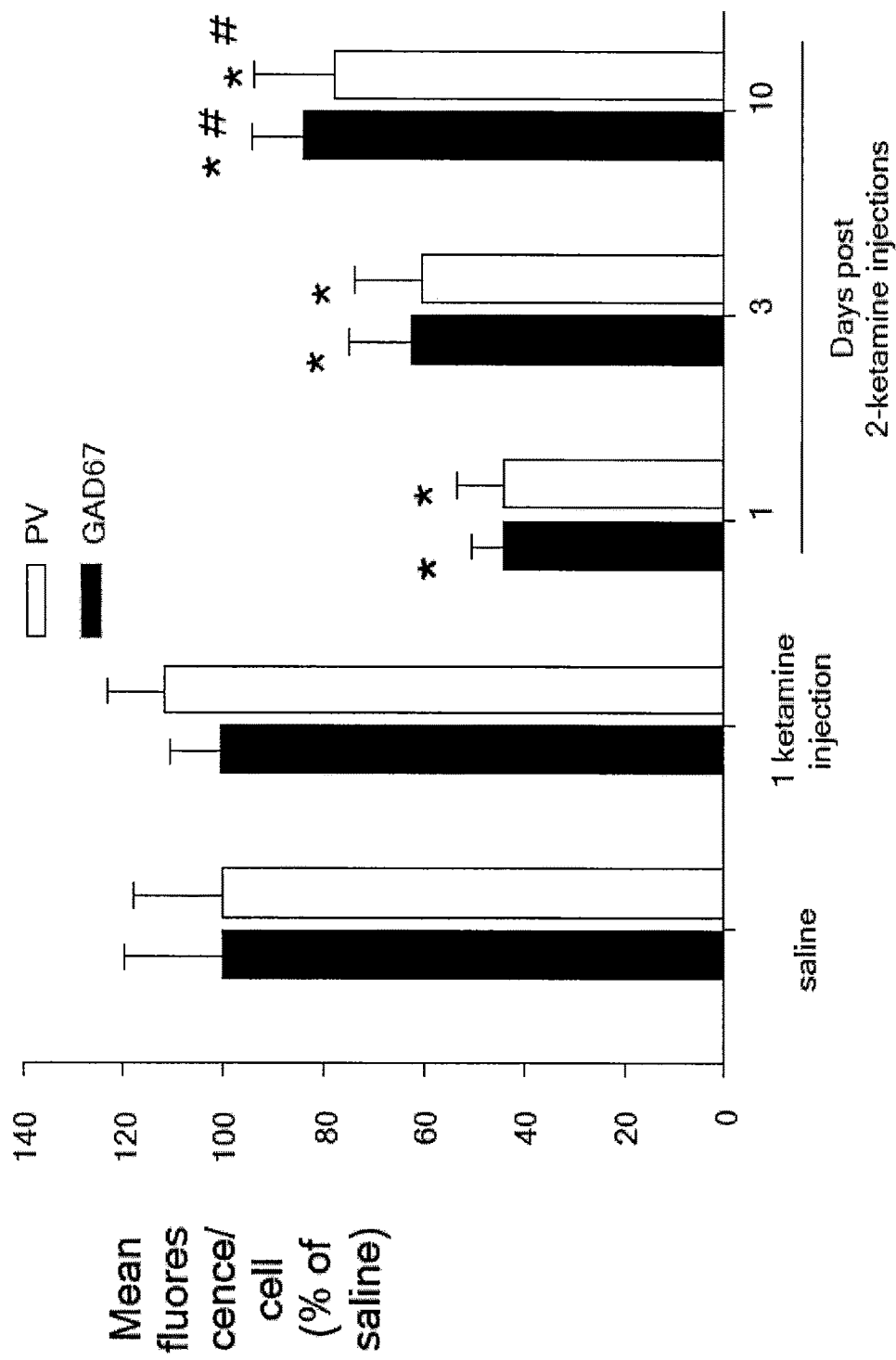
FIG. 23 graphically illustrates data showing the slow reversal of ketamine effects on PV-interneurons in vivo, as described in detail in Example 2, below.

In this study, the effects of ketamine on PV-interneurons in the prefrontal region were observed only after exposure on two consecutive days, and not present 24 h following a single exposure, as illustrated in FIG. 23, as previously reported for rat by Cochran (2002) Synapse 46:206-214. FIG. 23 graphically illustrates data showing the slow reversal of ketamine effects on PV-interneurons in vivo. C57BL/6 mice (3 month-old males) were treated with ketamine (30 mg/kg i.p.) on one or two consecutive days as described by Behrens et al., 2007, supra. Animals were sacrificed either 24 hr after a single injection or 1, 3, or 10 days after the second ketamine injection. Coronal brain sections comprising the prelimbic region were analyzed by fluorescence immunohistochemistry for parvalbumin (PV) and GAD67, and expressed as percent of saline treated controls. A slow increase in fluorescence intensity for both proteins is observed starting at 3 days after the second ketamine injection (* statistically significant with respect to saline at P<0.05; # statistically significant with respect to 2 days of ketamine at P<0.05. As determined by one way ANOVA followed by Tukey's test. ANOVA$_{(PV)}$: P<0.001, F: 16.344; ANOVA$_{(GAD67)}$: P<0.001, F: 20.926. n=15 animals for saline and 5 animals per time point. Each time point consisted of 5 saline and 5 ketamine treated animals. Since no differences were observed for the saline treated mice, these values were combined. Data are means±SD. Mean fluorescence intensity for saline: PV=160.6+/−13.3; GAD67=110.4+/−8.6.

Furthermore, as previously shown in microdialysis studies of rats 24 h after exposure to a single injection of ketamine by Zuo (2007) Pharmacol Biochem Behav. 86:1-7, we did not observe increase in DHE oxidation in the prelimbic region of mice 24 h after a single injection of ketamine (not shown).

These results support the conclusion that repeated exposure to NMDA-R antagonists is required to produce persistent changes in PV-interneuron phenotype and function; see e.g., Cochran (2003) Neuropsychopharmacology 28:265-275; Keilhoff (2004) Neuroscience 126:591-598; Rujescu (2006) Biol Psychiatry 59:721-729.

To test for the enduring effects of the two-day ketamine treatment on the loss of phenotype of PV-interneurons, adult male C57BL/6 mice were treated with ketamine (30 mg/kg) on two consecutive days and the PV-interneuronal population in the prelimbic region was analyzed on days 1, 3, and 10 after the last ketamine injection. As previously described (e.g., by Behrens et al., 2007, supra), a pronounced decrease in the expression of PV and GAD67 in PV-interneurons was observed one day after withdrawal; see FIG. 23. A slow reversal of this process was observed, although it still remained significant with respect to saline treated animals 10 days after withdrawal. The decrease was specific for the PV-interneuronal population, as demonstrated by the lack of effects of the 2-day ketamine treatment on the levels of calbindin (Mean intensity±SD: Saline=215.6±32.1; GAD67: 30.1±14.3, Ketamine=231.6±25.6, GAD67=44.2±14.5. ANOVA$_{(CB)}$: P=0.477, F=0.558. ANOVA$_{(GAD67)}$: P=0.588, F=0.319. n=6 animals per condition) and calretinin (Mean intensity±SD: Saline=133.6±35.6; GAD67: 30.1±14.3, Ketamine=139.4±28.7, GAD67=44.2±14.5. ANOVA$_{(CR)}$: P=0.786, F=0.079. ANOVA$_{(GAD67)}$: P=0.922, F=0.01. n=6 animals per condition).

To confirm the role of Nox2-dependent NADPH oxidase (Nox2) in the superoxide mediated loss of phenotype of PV-interneurons we exposed adult Nox2-deficient (gp91$^{phox}$−/−) male mice to ketamine (30 mg/kg) on two consecutive days, and injected dihydroethidium (DHE) 30 min after the last ketamine treatment to measure superoxide production as described by Behrens et al., 2007, supra.

Figure 24:
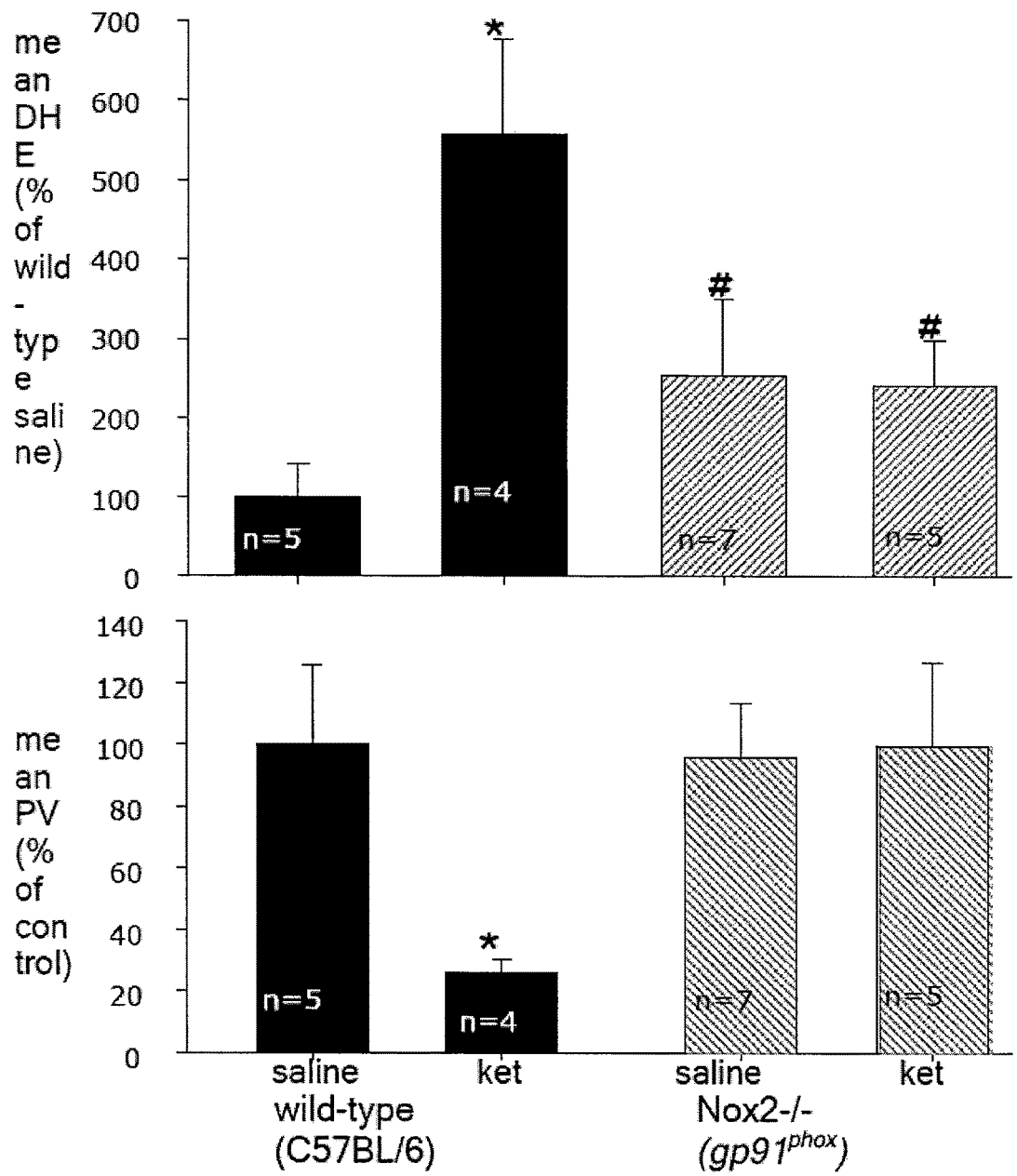
FIG. 24 graphically illustrates data showing an analysis of the prelimbic region that showed that deletion of Nox2 prevented the increase in superoxide induced by ketamine, as shown by the data graphically illustrated in the top graphic, and protected the phenotype of PV-interneurons, as shown by the data graphically illustrated in the lower graphic, as described in detail in Example 2, below.

Analysis of the prelimbic region showed that deletion of Nox2 prevented the increase in superoxide induced by ketamine, as shown by the data graphically illustrated in FIG. 24A, and protected the phenotype of PV-interneurons, as shown by the data graphically illustrated in FIG. 24B. The data of FIG. 24 demonstrates the absence of ketamine effects in the PFC of Nox2 knockout mice. Three month old gp91phox−/− were treated with ketamine (30 mg/kg i.p. on two consecutive days) followed by DHE injections. Coronal sections comprising the prelimbic and infralimbic regions were analyzed for (FIG. 24A) oxidized DHE, and (FIG. 24B) parvalbumin (PV) immunofluorescence. Fluorescence intensity is expressed as percent of saline treated C57BL/6 animals. (A: ox-DHE: *, # significant with respect to saline C57BL/6. * P<0.001, #P=0.026 by Tukey's test. ANOVA: P<0.001, F: 26.782; B: PV: * P<0.001 with respect to saline C57BL/6. ANOVA: P<0.001, F: 11.555). Data are means±SD. Mean fluorescence intensity for saline C57BL/6 control: ox-DHE=9.8+/−1.5; PV=147.2+/−23.3.

Figure 25:
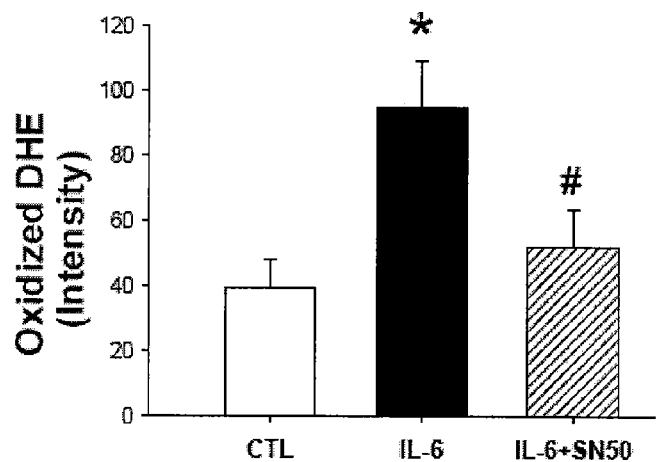
FIG. 25 graphically illustrates data from neuronal cultures exposed to ketamine and IL-6, which shows that blocking activity of the transcription factor NFκB using SN50 blocks induction and activation of Nox2, as assessed by DHE oxidation, as described in detail in Example 2, below.

FIG. 25 graphically illustrates data from neuronal cultures exposed to ketamine and IL-6, which shows that blocking activity of the transcription factor NFκB using SN50 blocks induction and activation of Nox2, as assessed by DHE oxidation. The NFκB inhibitor SN50 blocks IL-6 induced superoxide production in neuronal cultures. Cultures were exposed to IL-6 with or without SN50 and superoxide production (DHE oxidation) was assessed 4 hours later. Inhibition of NFκB blocked induction and activation of Nox2 in neurons by IL-6.

These results confirm the specific role of Nox2-dependent superoxide production in the loss of phenotype of PV-interneurons caused by ketamine exposure. Increased basal level of superoxide production in gp91phox−/− animals were previously observed, and attributed to developmental compensatory mechanisms that lead to increased expression of other Nox subunits; see e.g., Byrne (2003) Circ Res 93:802-805; Liu (2007) Can J Neurol Sci 34:356-361.

We also observed an increased basal level of DHE oxidation in brains of Nox2-deficient animals, as illustrated in the data summarized in FIG. 24A. However, this level of superoxide production was not sufficient to affect PV-interneurons, as illustrated in the data summarized in FIG. 24A. These results give strong support to a specific role of Nox2-dependent activation in the effects of NMDA-R antagonists on PV-interneurons.

Ketamine Exposure Induces IL-6 Expression.

To directly examine whether ketamine exposure induced the expression of the cytokine in neurons, we exposed primary cortical cultures to ketamine and analyzed IL-6, IL-1 and TNF mRNA at different time points during the 24 hours exposure. PCR amplification of reverse transcribed mRNA showed that ketamine exposure induced a sustained increase only in IL-6 transcript; as graphically illustrated by the data in FIG. 21, without affecting the levels of other pro-inflammatory cytokines. The level of IL-6 mRNA remained significantly elevated with respect to control conditions 24 hours after ketamine (180±18.1%, P=0.01). In FIG. 21 primary neuronal cultures were exposed to ketamine (0.5 μM) for the times indicated and the abundance of IL-6 mRNA was determined by PCR using specific primers after reverse-transcription of mRNA obtained from the cultures. Values for IL-6 mRNA abundance were obtained after normalization by the expression of GAPDH mRNA in the samples. (* indicates significance with respect to control conditions (P$_{(3h)}$=0.009, P$_{(6h)}$=0.001) by Tukey's test. ANOVA: P=0.001, F: 46.950. n=3 experiments per timepoint).

Primary neuronal cultures also were exposed to ketamine (0.5 μM) for the times indicated and the abundance of IL-6, IL-1, and TNF mRNA were determined by PCR using specific primers after reverse-transcription of mRNA obtained from the cultures. Values for mRNA abundance were obtained after normalization by the expression of GAPDH mRNA in the samples; significance with respect to control conditions at P<0.001 determined by Tukey's multiple comparisons test. ANOVA: P=0.001, F: 46.950.

To test if glial cells were responsible for the increase in IL-6 upon ketamine exposure, we applied the NMDA-R antagonist to neurons in the absence of the astrocytic layer, and analyzed the PV-interneuronal population 24 h later. Ketamine produced a similar increase in DHE oxidation and loss of phenotype of PV-interneurons in the presence or absence of the astrocytic layer, as graphically illustrated by the data of FIG. 26, demonstrating that if IL-6 mediates these effects, it must be of neuronal origin.

Figure 26:
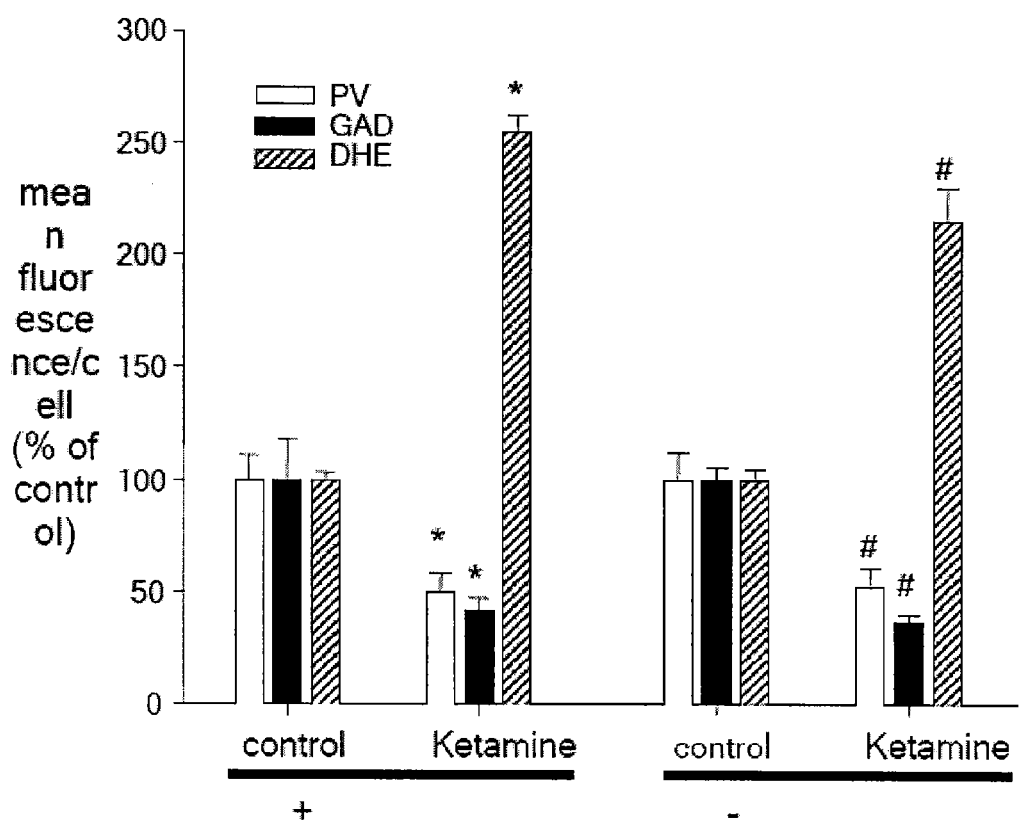
FIG. 26 graphically illustrates data testing whether glial cells were responsible for the increase in IL-6 upon ketamine exposure; the NMDA-R antagonist ketamine was applied to neurons in the absence of the astrocytic layer, and the PV-interneuronal population analyzed; ketamine produced a similar increase in DHE oxidation and loss of phenotype of PV-interneurons in the presence or absence of the astrocytic layer, as described in detail in Example 2, below.

To generate the data of FIG. 26, primary neuronal cultures were grown on glass coverslips with "feet" as described by Kinney (2006) J. Neurosci. 26:1604. After 21 days of development in vitro, the cultures were treated with ketamine (0.5 mM for 24 h) in the presence or absence of the astrocytic layer. For this, the coverslips containing neurons were separated from the astrocytic layer by transfer of the coverslip together with its media into an empty well. DHE was added for the last hour of treatment as described by Behrens et al., 2007, supra. After treatment, neurons were fixed and processed for immunofluorescence for detection of either PV or GAD67 or for oxidized DHE. *, # indicates statistical significance with respect to control conditions at P<0.001 by ANOVA followed by Tukey's test. ANOVA (PV): P=0.003, F: 7.569; ANOVA(GAD67): P<0.001, F: 10.103; ANOVA(oxDHE): P<0.001, F: 94.583. n=3-5 experiments per condition. Data are means±SEM. Baseline intensities: PV=210±32; GAD67=195±26.

To confirm this hypothesis, we applied IL-6 blocking antibodies, as described e.g., by Smith (2007) J. Neurosci. 27:10695-10702, during the 24 hours exposure of primary neurons to ketamine in the absence of the astrocytic layer. Blocking IL-6 with two different antibodies completely prevented ketamine effects on PV-interneurons, as shown by the data graphically illustrated in FIG. 27A; and also the increase in superoxide, as shown by the data graphically illustrated in FIG. 27B, indicating that IL-6 is the downstream mediator of ketamine effects on Nox2 induction and activation.

Figure 27:
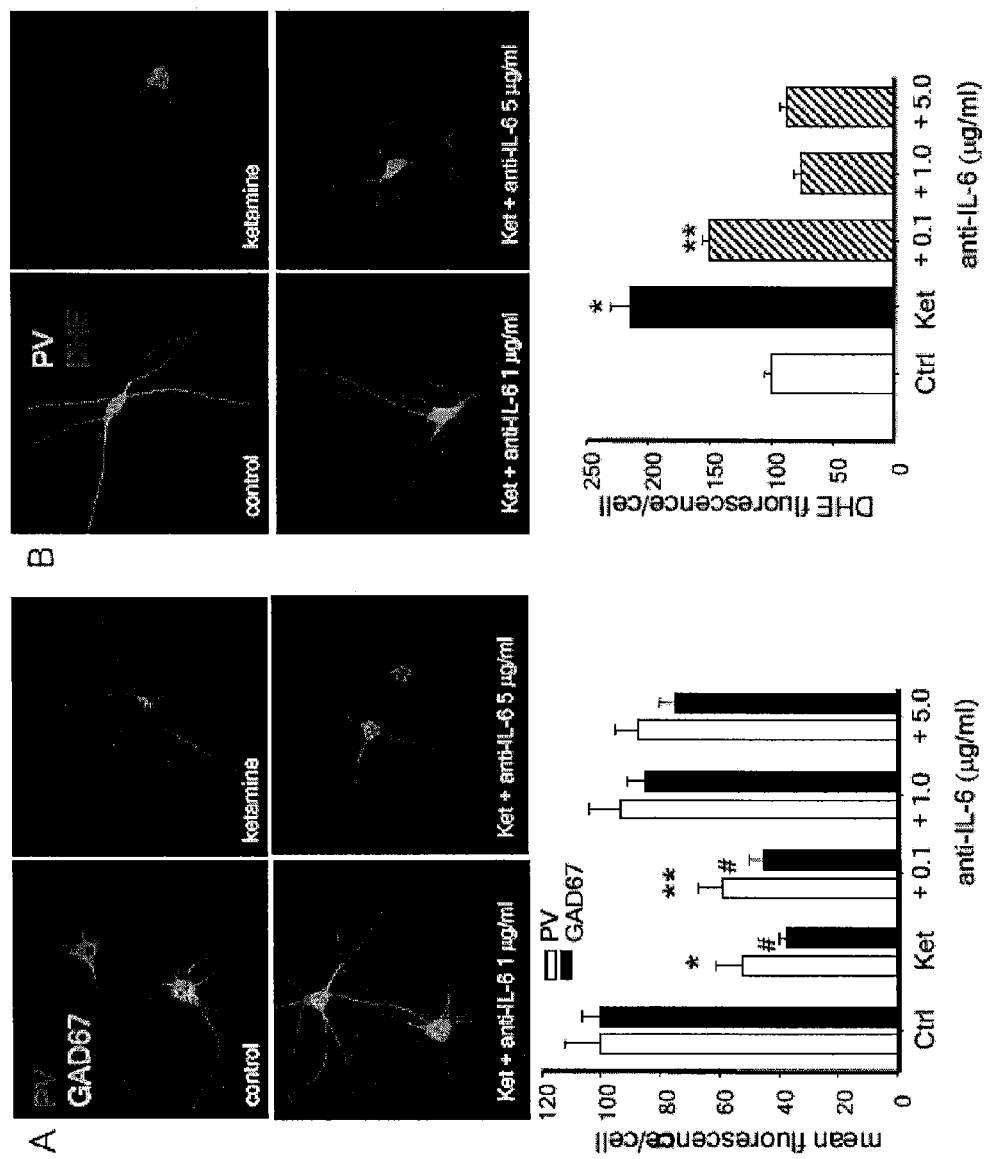
FIG. 27 by graphs and imaging illustrates data where primary neuronal cultures were exposed to ketamine in the absence of the astrocytic monolayer and in the presence of an anti-mouse IL-6 blocking antibody produced in goat (anti-mIL-6)

For FIG. 27: primary neuronal cultures were exposed to ketamine in the absence of the astrocytic monolayer and in the presence of an anti-mouse IL-6 blocking antibody produced in goat (anti-mIL-6). FIG. 27A: Increasing concentrations of anti-mIL-6 prevented the decrease in parvalbumin (PV) and GAD67 after 24 h of ketamine exposure. Bar graph show results for fluorescence quantification of both antigens in PV-interneurons expressed as % of control. *,** P=0.006 and 0.028 respectively; #,## P<0.001 by Tukey's test. ANOVA$_{(PV)}$: P=0.002, F: 4.564, ANOVA$_{(GAD67)}$: P<0.001, F: 27.512; n=4 experiments per condition. Baseline intensities: PV=165±30; GAD67=127±28. FIG. 27B: Neuronal cultures were treated as in A, and DHE was added for the last hour of treatment. After fixation, the coverslips were processed for immunocytochemistry for parvalbumin (PV, green). Bar graph show results for oxidized DHE fluorescence (red) intensity analysis in all neurons including PV-interneurons. (* P<0.001 with respect to control and ** P<0.001 with respect to ketamine by one way ANOVA followed by Tukey's test. ANOVA: P<0.001, F$_{stat}$: 46.415. n=3 experiments per condition). Baseline intensities: DHE=25.4±5.4.

For these experiments, two different blocking antibodies, produced in different species, were used. The blocking capacity of these two antibodies differ by a factor of ten (as described by manufacturer), and a similar difference was observed when blocking ketamine effects, as graphically illustrated by the data shown in FIGS. 27 and 28.

Figure 28:
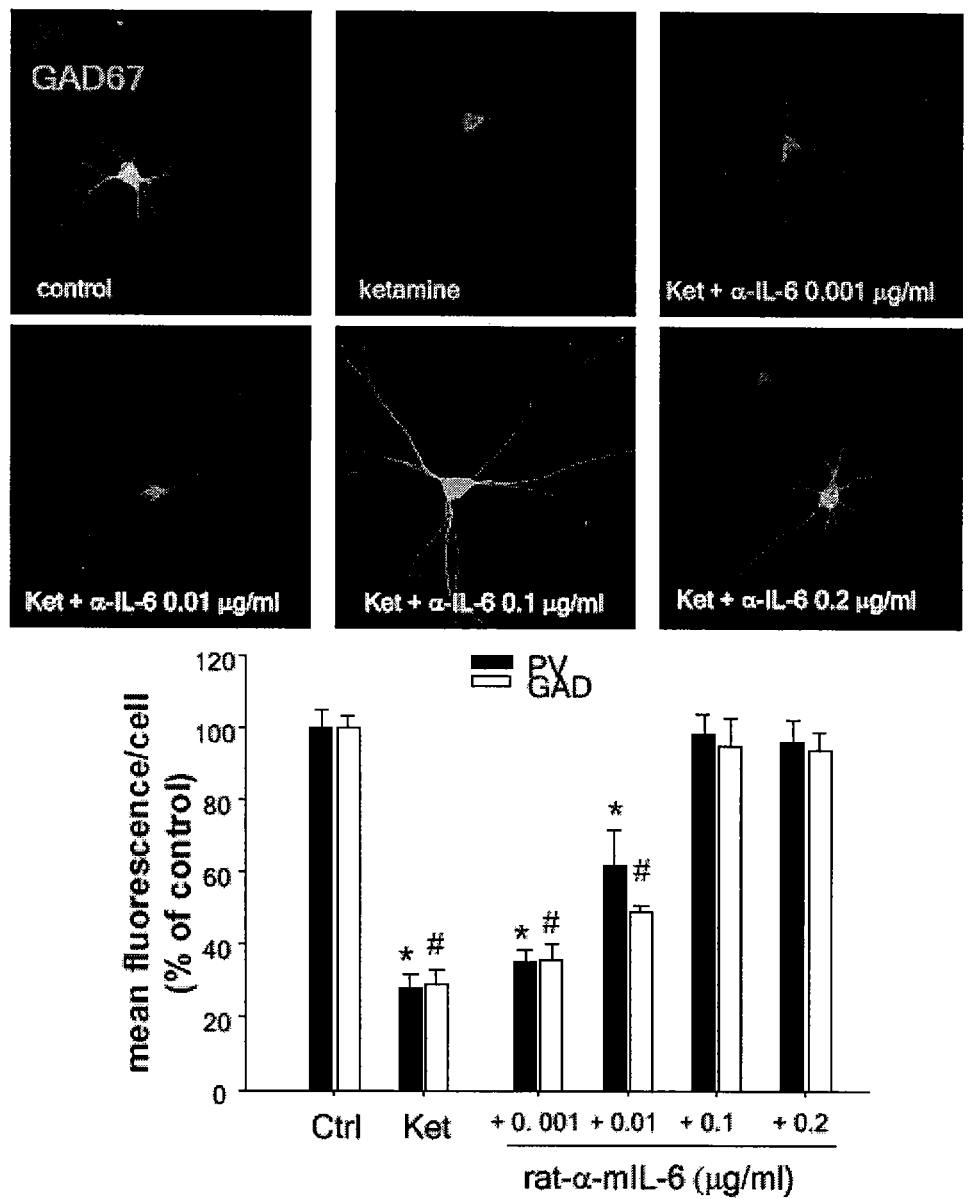
FIG. 28 by graphs and imaging illustrates data where primary neuronal cultures were exposed to ketamine in the absence of the astrocytic monolayer and in the presence of an anti-mouse IL-6 blocking antibody produced in rat (anti-mIL-6)

For FIG. 28: primary neuronal cultures were exposed to ketamine in the absence of the astrocytic monolayer and in the presence of an anti-mouse IL-6 blocking antibody produced in rat (anti-mIL-6). Increasing concentrations of anti-mIL-6 prevented the decrease in parvalbumin (PV) and GAD67 after 24 h of ketamine exposure. Bar graph show results for fluorescence quantification of both antigens in PV-interneurons expressed as % of control. *,# P<0.001 with respect to control by Tukey's multiple comparisons test. ANOVA$_{(PV)}$: P<0.001, F: 28.727; ANOVA(GAD67): P<0.001, F: 39.684. n=3 experiments per condition.

Figure 29:
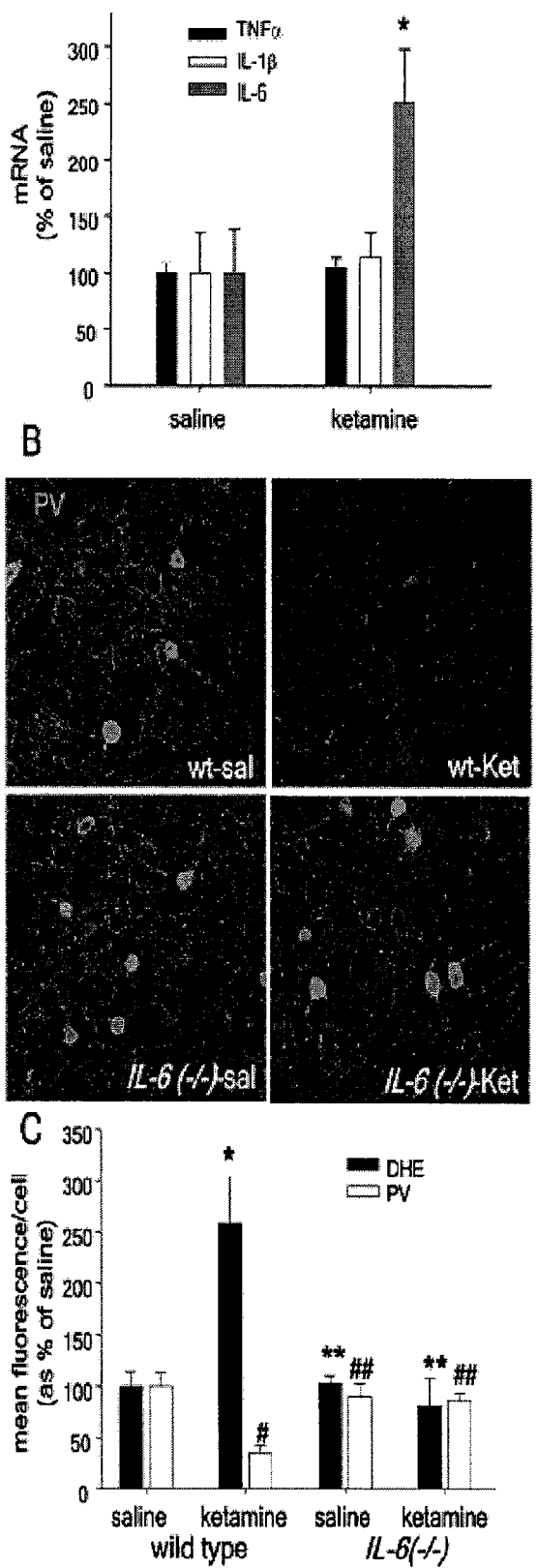
FIG. 29B upper image graphically illustrates results showing that ketamine exposure in vivo on two consecutive days leads to increased mRNA expression of IL-6 in brain, without affecting the expression levels of IL-1β or TNFα, as illustrated in the lower image, FIG. 29C graphically illustrates data showing that ketamine does not lead to increased DHE oxidation and loss of GABAergic phenotype of PV-interneurons in IL-6−/− mice, as described in detail in Example 2, below.

The data graphically illustrated in FIG. 29 shows that ketamine does not lead to loss of GABAergic phenotype of PV-interneurons in IL-6−/− mice. To assess whether IL-6 and other inflammatory cytokines were induced in brain after ketamine exposure we analyzed the levels of mRNA for IL-6, IL-1β and TNFα, as previously shown for cultured neurons. Exposure to ketamine on two consecutive days only increased the levels of IL-6 mRNA, as illustrated in FIG. 29A, without affecting mRNA levels of IL-1 or TNF.

To further assess the role of IL-6 in ketamine effects in vivo, we exposed IL-6-deficient mice to ketamine on two consecutive days, and analyzed the PV-interneuronal population in the prefrontal region, as well as the activity of Nox2-dependent superoxide production by DHE oxidation. Lack of in vivo production of IL-6 prevented ketamine activation of NADPH oxidase, as determined by the diminished DHE oxidation in the IL-6-deficient mice (FIG. 29A). Moreover, the phenotype of PV-interneurons in the prefrontal region was preserved in the IL-6-deficient animals (FIG. 29B). These results demonstrate that CNS production of IL-6 is necessary and sufficient for the increase in Nox2-dependent NADPH oxidase activity that leads to the loss of phenotype of PV-interneurons observed after ketamine exposure.

In FIG. 29, illustrating data showing CNS production of IL-6 mediating ketamine effects on Nox and PV-interneurons in vivo: FIG. 29A: animals were treated with saline or ketamine (30 mg/kg) on two-consecutive days and the brains extracted for mRNA preparation 24 h after the last ketamine injection. The abundance of IL-6, IL-1β, and TNFα mRNA was determined by PCR using specific primers after reverse-transcription of mRNA obtained from forebrains. Values for mRNA abundance were obtained after normalization by the expression of GAPDH mRNA in the samples. (* indicates significance with respect to control conditions at P=0.012 by ANOVA followed by Tukey's test. F: 12.775, n=4 animals per condition). In FIG. 29B, three month old C57BL/6 (wt) or IL-6-deficient (IL-6(−/−)) male mice were treated with ketamine (30 mg/kg) on two consecutive days, followed by DHE, as described by Behrens et al., 2007, supra. Coronal sections comprising the prelimbic and infralimbic regions were analyzed by immunohistochemistry for parvalbumin (PV) and oxidized DHE fluorescence. Ketamine produced a substantial increase in oxidized DHE in wild type mice but not in IL-6(−/−) animals. The loss of parvalbumin expression induced by ketamine was prevented in the IL-6(−/−) animals. (*=oxDHE wt-saline vs wt-ketamine P<0.001; **=oxDHE wt-ketamine vs IL-6(−/−) P=0.001 by Tukey's test. ANOVA$_{(oxDHE)}$: P<0.001, F: 18.577. #=PV wt-sal vs wt-ketamine at P<0.001; ##=PV wt-ketamine vs IL-6(−/−) P<0.001 by Tukey's test. ANOVA$_{(PV)}$: P<0.001, F: 30.184. n=4 animals per condition). Data are means±SD.

Mean fluorescence intensity for saline: wild type, PV=111.6+/−9.3; ox-DHE=10.1+/−2.5; IL-6(−/−), PV=101.7+/−10.2; ox-DHE=11.7+/−3.2.

Figure 30:
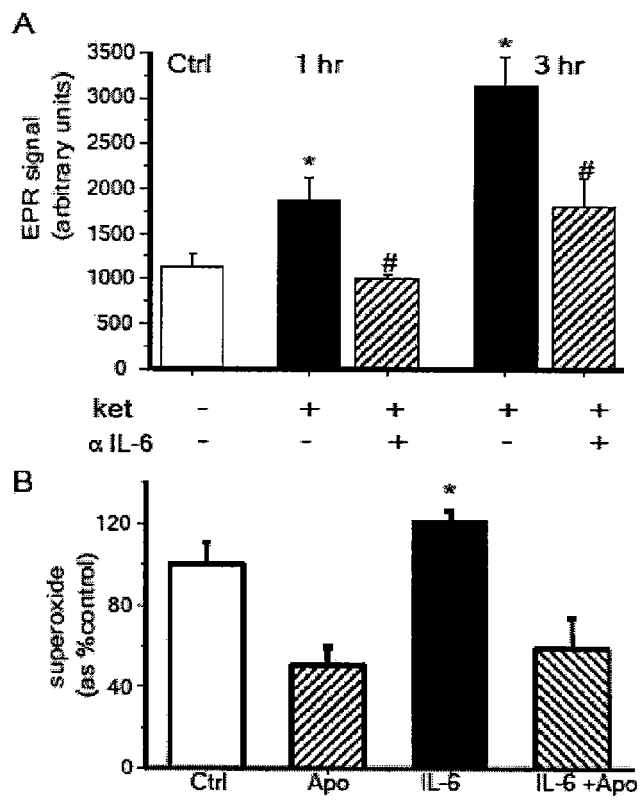
FIG. 30 graphically illustrates data showing that ketamine-induced IL-6 release directly activates Nox; FIG.

The data graphically illustrated in FIG. 30 shows that IL-6 directly activates NADPH oxidase. Superoxide production by live neurons, as analyzed by electron paramagnetic resonance (EPR), increased rapidly after ketamine exposure (FIG. 30). To confirm that this effect of ketamine was mediated by IL-6, a blocking antibody against IL-6 was applied during the exposure to ketamine and the activity of Nox was analyzed by EPR in live cultures as before. Blocking IL-6 action with the antibody prevented the activation of Nox by ketamine (FIG. 30A). Moreover, to further test whether IL-6 triggers the signaling cascades that activate the oxidase, synaptosomal preparations were exposed to IL-6 (100 ng/ml) and superoxide production was assayed by EPR. IL-6 produced a small but significant increase in superoxide that was completely blocked by co-exposure to apocynin, demonstrating that it was produced by Nox2-dependent NADPH oxidase (FIG. 30B).

In FIG. 30, illustrating data showing that ketamine-induced IL-6 release directly activates Nox. A: EPR assessment of superoxide production in live cultures upon treatment with ketamine (0.5 µM). Primary cultures were exposed to ketamine for the times indicated in the absence or presence of an anti-mouse IL-6 blocking antibody produced in rat (anti-IL-6, 0.1 µg/ml). At the indicated times, the coverslips were transferred to a quartz chamber and superoxide production was followed by EPR spectroscopy using the spin-trap DIPPMPO. Ketamine induced a rapid increase in superoxide signals that were significantly reduced by the blocking antibody (*=significant with respect control, P=0.03 and 0.0002 for 1 h and 3 h, respectively. #=significant with respect to ketamine, P<0.05 by Tukey's test of multiple comparisons. 2-way ANOVA: P=0.002, F=7.786. n=3-6 experiments per condition). FIG. 30B: IL-6 (100 ng/ml) increased basal NADPH oxidase activity in forebrain synaptosomes isolated from 3 month-old C57BL/6 male forebrains. IL-6 was pre-incubated with synaptosomal preparations for 5 minutes before triggering oxidase activity by addition of substrate, NADPH. Apocynin (0.4 mM) was applied 5 min before IL-6. Accumulation of superoxide during the first 6 min was analyzed using the spin trap DEPMPO. Data are means±SEM. *P<0.001 control vs. IL-6 and #P<0.001 apocynin treated vs. no apocynin by ANOVA and Tukey's post-hoc test, F: 55.8, n=5-7 experiments per condition.

General Methods Example 2

Maintenance of Mice, and In Vivo Administration of Ketamine, Nox Inhibitors, SOD Mimetic Inhibitors, IL-6

All mice for these studies are housed in the barrier facility at UCSD. Pathogen-free C57BL6 mice will be obtained from Jackson Labs, and the PI maintains breeding colonies of gp91phox−/− and IL-6−/− mice. gp91phox−/− mice are maintained on autoclaved water and are handled with sterile technique during weaning. All animal studies have been approved by the Animal Care Program at the University of California, San Diego, and are in accordance the PHS Guide for the Care and Use of Laboratory Animals, USDA Regulations, and the AVMA Panel on Euthanasia. The Nox inhibitor, apocynin (5 mg/kg/day) and the SOD mimetic, $C_3$ (a SOD inhibitor), 1 mg/kg/day, will be given in the drinking water for 7 or more days, with an assumed intake of 13 ml $H_2O$/mouse/day.

In our preliminary studies $C_3$ was given through mini-pumps. Since we have shown that it can be given in the drinking water also (Quick et al., 2006), we prefer this way of delivery in the future to avoid animal surgery. Intracerebral (i.c.v.) injection of IL-6 or ketamine will be performed only if needed using a mouse stereotax and established coordinates. Intraperitoneal IL-6 (5 µg/kg), a dose established from our previous dose-response studies.

Analysis of Superoxide and/or Hydrogen Peroxide Production by Confocal Imaging of In Vivo Dihydroethidium (DHE) Oxidation.

Mice will be injected intraperitoneally (i.p.) with dihydroethidium. Briefly, two serial i.p. injections of freshly prepared dihydroethidium (27 mg/kg) are given at 30 minute intervals. Eighteen hours later, mice are anesthetized with inhaled halothane, and are perfused intracardially with cold saline followed by 4% paraformaldehyde in PBS. Brains are removed and post-fixed in 2% paraformaldehyde for >24 h. Following fixation, brains are cut into 50 µm coronal sections and co-labeled with the appropriate primary and secondary antibodies for fluorescence visualization. Slices are mounted and evaluated for fluorescence from the DHE oxidation product using Ex λ 568 nm, Em λ>590 nm on a LSM510 META™ multiphoton laser confocal microscope (Karl Zeiss, Inc.). First, an image is taken in the fluorescence channel of the ICC-fluorophor and then the channel is switched to image fluorescence from DHE oxidation. Auto-fluorescence is determined in animals which did not receive DHE injections, but which are processed similarly to injected animals. Using the image pairs for each field and MetaMorph software, an analyst blind to the group circles the outline of each ICC-labeled cell and then switches to the DHE oxidation image. The average fluorescence intensity for each cell of interest is logged, and values averaged to determine the mean fluorescence/cell.

Immunohistochemistry (IHC) and Immunocytochemistry (ICC).

Mice are anesthetized and perfused as above. Coronal sections, at 50 µm thickness are treated with 1% sodium borohydride for antigen retrieval, washed, and blocked in 10% normal serum overnight. Slices are incubated with primary antibodies (Abs) in 2% normal serum at 4° C. overnight, washed in PBS, and incubated in secondary Abs conjugated to ALEXAFLUOR™ dyes (488 and 568) for 1 hour at room temperature. When analyzing DHE oxidation and a specific Ab staining, secondary Abs are always ALEXAFLUOR488™ dyes conjugated. For ICC in cultures, coverslips are washed by immersion in PBS, and fixed in ice-cold 4% paraformaldehyde for 30 min, and then incubated for 10 min at room temperature in PBS containing 0.25% Triton X-100. Non-specific sites are blocked by incubation in PBS containing 10% serum (goat or horse). For double immunostaining, the coverslips are incubated in 2% normal goat serum containing mAb against GAD67 (1:1000, Chemicon), Nox2 (1:200) or p47phox (1:50), rabbit polyclonal Ab against Parvalbumin (1:3000, Swant, Bellinzona, Switzerland), MAP2 (1:1000, Chemicon), or $p22^{phox}$ (1:300. Santa Cruz), and incubated for 1-2 h at 37° C. Specific binding is detected by incubation for 45 min at room temperature with a 1:1000 dilution of secondary Abs conjugated to ALEXAFLUOR™ dyes (568: red, 488: green, Molecular Probes).

Fluorescence Quantification of IHC and ICC.

The settings on the confocal microscope are maintained constant for each series of experiments to allow images to be analyzed and compared by densitometry. For cell imaging, each slice is imaged across the prelimbic and infralimbic regions between Bregma 1.3 and 2.0. Six slices are analyzed per animal by taking 3×8 image stacks (corresponding to 1.4 µm) of the region with a 10× APOFLUOR™ objective encompassing the whole PFC (18×8 images per animal). All PV-neurons in the images are analyzed for their parvalbumin and GAD67 content. For analysis of overall neuronal population in primary cultures, coverslips are scanned to obtain 200-400 neurons (approx. 26-30 images captured per coverslip per condition using a 40× water immersion objective). Each image analyzed consists of a stack of 16 0.2 µm Z-stage images taken from the base of the neurons and across 3.2 µm depth. When analyzing PV-interneurons, the coverslips are scanned to obtain images as before but for all the PV-interneurons in the coverslip.

Analysis of Nox Proteins by Western Blot.

Preparation of samples and subcellular fractionation is carried out as described below. For Western blotting, samples are prepared for SDS-PAGE using standard procedures. After SDS-PAGE on 10-12% acrylamide gels, proteins are transferred to a nitrocellulose membrane, blocked in Tris-Buffered Saline TWEEN-20™ (TBST) with 5% milk, and incubated with Abs to Nox(s) or subunit proteins at 4° C. overnight. We have established conditions for the following Abs: monoclonals 44.1 ($p22^{phox}$; 1:1000) and 54.1 (Nox2; 1:1000), Nox4 polyclonal (1:1500), and p47phox monoclonal (1:50, Santa Cruz). After incubation with host-appropriate secondary Abs, the membranes are washed and developed with ECL (Pierce, Inc.).

Isolation of Synaptosomes.

For each preparation, pooling of two forebrains was found to provide sufficient protein (10-15 mg) to run one oxygraph measurement and one EPR experiment. Mice are euthanized by exposure to a lethal dose of inhaled halothane, followed by cervical dislocation and brains are rapidly removed and placed onto ice-cold isolation buffer (0.32 M sucrose, 1 mM EDTA, 10 mM Tris-HCl buffer, pH 7.4, 10 mM glucose). Using a glass-dounce homogenizer, the cortex is minced and homogenized in isolation buffer. The homogenate is centrifuged at 3100 rpm for 3 min at 4° C., and the supernatant is collected; the pellet is re-homogenized in half the volume of isolation buffer and centrifuged again. The supernatants are pooled, and mixed with PERCOLL™ to a final concentration of 15%. The sample is layered onto a gradient of 23% and 40% PERCOLL™. The fractions are separated by centrifugation at 16,000 rpm for 5 minutes. The uppermost band is extracted, rinsed in the isolation buffer, centrifuged and resuspended in synaptosome buffer (120 mM NaCl, 4.7 mM KCl, 2.2 mM $CaCl_2$, 1.2 mM $MgCl_2$, 25 mM HEPES, 1.2 mM $MgSO_4$, 1.2 mM $KH_2PO_4$, 10 mM glucose).

Oxygen Consumption Studies (Oximetry).

$O_2$ consumption studies on synaptosomes are carried out. $O_2$ utilization is measured using an oxygen Clark-type electrode, OXYGRAPH™ (Hansatech, UK) with OXYGRAPH™ software. Studies were carried out to optimize the concentration of synaptosomal protein required, and to confirm stability and viability of synaptosomes and their mitochondria for up to 6 h.

Superoxide Detection by Electron Paramagnetic Resonance (EPR) Spectroscopy:

After incubation of the reaction mixture containing 5 mg synaptosomal protein, 70 mM DIPPMPO (5-(diisopropoxyphosphoryl)-5-methyl-1-pyrroline-N-oxide, Alexis Biochemicals, San Diego, Calif.), and appropriate combinations of the substrates/inhibitors for 1 hr at 37° C., the mixture was injected into the EPR cavity of a Bruker ESCAN™ (eScan) Benchtop spectrometer (Bruker BioSpin, MA, USA) through a gas-permeable Teflon tube. The EPR settings were: receiver gain, $1\times10^3$, scan width, 200 G centered at 3484.9 G, modulation amplitude 4 G, time constant 5.16 ms, modulation frequency 86 kHz, microwave power 5.04 mW, 5.24-s sweep time, and the spectrometer operating frequency was 9.784 GHz.

Preparation of Cortical Cell Cultures.

One-Step Neuronal-Glial Cultures-(Used for confocal imaging and biochemistry). Cultures are prepared from fetal (E14-15) Swiss Webster mice as described (Kinney et al., 2006). Briefly, cortices are dissected from the rest of the brain, placed in 5 ml of growth media, which consists of media stock (MS: Eagle's Minimal Essential Media minus glutamine) with the addition of 20 mM glucose, 26.2 mM $NaHCO_3$, 2 mM glutamine, 5% fetal calf serum, 5% horse serum. The tissue is then triturated using a 5 ml pipette, and cell suspensions are diluted to 0.15 cortices/ml and plated onto poly-lysine coated coverslips. When glia has reached confluency, proliferation is halted by addition of 10 µM cytosine arabinoside (AraC) for 48 h. Cultures are fed biweekly with growth media (MS with 10% horse serum), and used for experiments at DIV21-28. Dissociated neuronal cultures—(used for confocal microscopy) Cortical neurons are cultured at low density from the same E14-15 dissections described above, following a slightly modified procedure form that described for rat hippocampal cultures which we substituted ovalbumin for 2% horse serum in the media, since we discovered that mouse astrocytes do not survive in the presence of this protein. Briefly, neurons are seeded on glass coverslips to which paraffin feet were added, after cell attachment the coverslips are flipped on top of the astrocytes grown in MS/N2.1 media (MS plus 1×N2.1 supplements (Gibco), 2% horse serum, 2 mM L-glutamine, 1 mM pyruvate, and 12 mM glucose) as described e.g. by Kinney, et al. (2006) J. Neurosci. 26:1604-1615. Five (5) µM cytosine arabinoside is immediately added to halt the grown of non-neuronal cells. These co-cultures are maintained in MS/N2.1 media for 21 days. Most neurons develop the characteristic morphology of pyramidal cells. Immunostaining with αCaMKII antibodies and GAD67 antibodies confirmed that 80-90% of the population is pyramidal neurons and 10-20% is GABAergic neurons.

Quantitative PCR.

qPCR for cytokines including IL-6, IL-2, and TNFα will be performed at the Gene-Array Core Facility at UCSD using published qPCR primer sets. The results are normalized by the expression levels of the reference gene, GAPDH, which is quantified simultaneously with the target.

Statistical Analysis.

All intensity values were normalized by the mean obtained for the control (primary cultures) or saline (in vivo) conditions for each experiment, processed in parallel with the experimental group, and expressed as a percent of this mean. To obtain the mean fluorescence/cell/animal, % values were averaged across the six slices of the same animal (or experiment in the case of primary cultures in coverslips), and the mean fluorescence intensity/cell/animal (or per experiment in the case of primary cultures) was used to calculate the mean and standard deviation per group. These were then used for statistical analysis using SigmaStat software. Values obtained per experiment were analyzed by Process for the Removal of Contaminants from Preparations of Malonic Acid Derivatives of Fullerene C60

In one embodiment, C60 fullerene derivatives (e.g., $C_3$, or tris malonic acid C60) or other malonic acid derivatives are used to practice this invention, e.g., as therapeutic agents for the clinical applications described herein. While the invention is not limited by any particular mechanism of action, in one embodiment, the C60 fullerenes (e.g., $C_3$, or tris malonic acid C60) or other malonic acid derivatives act as superoxide dismutase mimetics, thereby augmenting the action of endogenous SOD to decrease the amount of superoxide, thereby having a cytoprotective effect. In one embodiment, the class of compounds comprising malonic acid derivatives, including $C_3$ (tris malonic acid C60), are used to practice this invention; these compounds are cytoprotective in cell culture and animal models of disease, and are in preclinical testing.

Any method known in the art can be used to purify and/or prepare C60 fullerene derivatives (e.g., $C_3$, or tris malonic acid C60) or malonic acid derivatives to practice this invention, including for example the purification and scale-up synthesis protocols for $C_3$ as described by e.g., U.S. Pat. No. 6,538,153, Hirsch, et al., describing methods comprising steps of forming macrocyclic malonate compounds, including the tris malonic acid C60; or as described in U.S. Pat. No. 7,070,810, Hirsch, et al., describing amphiphilic substituted fullerenes and fullerenes comprising a fullerene core and a functional moiety, and methods for making them; or as described by C. Bingel (1993) Chem. Ber. 126:1957. The Bingel reaction is a popular method in fullerene chemistry where the malonate is functionalized with a halide atom in a mixture of base and tetrachloromethane or iodine; the reaction can take place with ester groups replaced by alkyne groups in dialkynylmethanofullerenes.

C60 fullerene derivatives (e.g., $C_3$, or tris malonic acid C60) or other malonic acid derivatives to practice this invention also can be prepared and/or purified as described herein, where this invention provides a new method for purifying C60 fullerene derivatives (e.g., $C_3$, or tris malonic acid C60) or other malonic acid derivatives. In one embodiment of this method, preparations of $C_3$ are prepared in water as a pH-neutral salt. Sodium hydroxide was used, but other salt preparations can be used in alternative embodiments. After incubation for a period of time, the toxic, waxy contaminant begins to precipitate, and can then be removed by high-speed centrifugation, filtering, appropriate column chromatography, or other techniques. Any residual volatile contaminant can be removed by vacuum distillation to produce a dried powder which can be re-dissolved in water to produce a pH neutral salt.

There are several synthetic approaches to generating $C_3$ and other malonic acid derivatives, to yield a single isomer, but most methods are not easily scaled up to generate sufficient compound for clinical applications. One method which may allow scale-up of synthesis of $C_3$ to the quantities needed for clinical testing and development of $C_3$ and like compounds as pharmaceuticals has been developed. However, preparations of $C_3$ using this method have been found to include a significant amount of a waxy contaminant which is highly toxic in cell cultures and in animals. This provides and describes methods for the removal of contaminants from preparations of malonic acid or malonic acid/acetic acid C60 derivatives.

Exemplary protocol: A 55 gram (g) lot of $C_3$ was received (C-Sixty, Ltd., Carbon Nanotechnologies Inc., Houston Tex.), who had commissioned synthesis of a stock of $C_3$ from Regis Technologies (Morton Grove, Ill.).

Attempts were made to dissolve the red powder in dilute NaOH, but a significant amount of particulate material which did not dissolve even with extensive mixing. When the partially solubilized solution was tested in neuronal cell cultures, it showed toxicity (increased neuronal death). The Regis preparation was also toxic when administered to mice at doses which had been non-toxic when internal preparations of $C_3$ were used. LC-MS on the compound indicated that there was a $CO_2$-containing component in the Regis preparation that was not present in pure $C_3$ samples prepared by alternative synthetic approaches. Absorption spectroscopy also indicated that there were contaminants which absorbed in the region 200-415 nm which were not present in preparations of $C_3$ which were previously documented to be non-toxic. Finally, it was observed that over time, a whitish waxy material precipitated out of solution in the Regis preparation but not $C_3$.

A 5 g lot of $C_3$ (prepared by J-Star, South Plainfield, N.J.) using the same template synthesis also contained the same precipitate/contaminant.

Procedure for Removal of Contaminants:

1) Dissolve powder in dilute sodium hydroxide (NaOH; range 0.25-2N), at $C_3$ concentrations between 10 mM-400 mM (10 mg/ml-400 mg/ml) at 4 degrees C. with stirring.

2) Add more concentrated NaOH (for example 5N NaOH) drop-wise to achieve pH~7.0. The current Regis $C_3$ preparation has required 4.8 mEq per g to produce a solution at pH 7.0.

3) The sample is then allowed to sit at 4 degrees in the dark for 0.5-3 hours.

4) The sample is centrifuged at 6000 g×30-60 minutes, which produces a clear dark red supernatant, and a solid light pink pellet. The supernatant is carefully removed by pipette to another tube. The supernatant can be allowed to sit at 4 degrees for an additional 3-4 hours, and then centrifuged again to be sure that all undissolved material is removed. The pellet with insoluble waxy material contains the contaminant, and small amounts of residual $C_3$, which can be extracted by additional NaOH, and repeat centrifugation.

5) The purified $C_3$ solution may have a minor amount of volatile contaminant that can be further removed by vacuum distillation or by bubbling an inert gas (e.g. nitrogen, argon) through the solution.

6) An alternative approach to removing the insoluble waxy contaminant after solubilization in dilute NaOH is to filter the sample through a filter which allows only aqueous solutions to pass.

7) Additional approaches could include 2-phase extraction if the waxy contaminant, the use of resins or other substances which can bind to the waxy contaminant.

8) An alternative approach would be to use antibodies directed against C60, $C_3$, or other malonic acid derivatives to precipitate the pure compounds away from the contaminant. Differential centrifugation or affinity column chromatography are two potential methods to then capture the fullerene-antibody complex.

Characterization of Purified Product from Centrifugation-Based Purification:

1) Samples were evaluated by absorbance spectroscopy. Pure $C_3$ has a characteristic spectrum with a maximum at 486 nm and a minimum at 413 nm that allows purity and concentrations to be assessed. A max/min ratio of >4.0 is highly pure. Using absorption at 486 nm and an extinction coefficient of 4200 mol cm−1, the concentration to be calculated.

2) HPLC was also performed to determine the presence of other non-$C_3$ isomers or decarboxylation products of $C_3$ in the purified solution.

Figure 36:
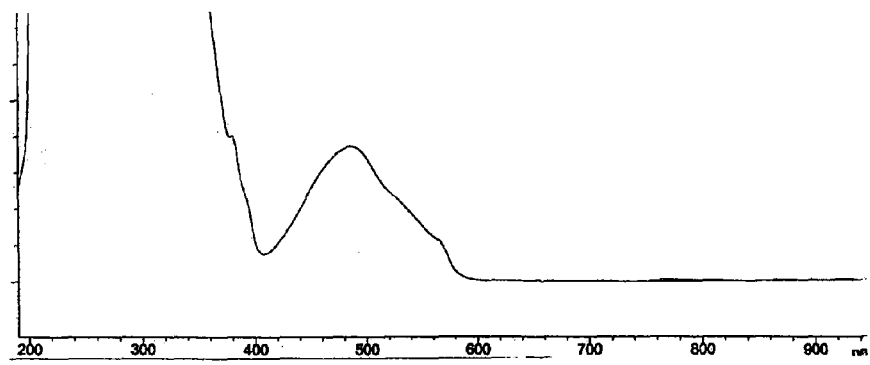
FIG. 36 illustrates the absorption spectra of pure $C_3$ prepared by the Bingel procedure, as described in detail in Example 2, below.

Results:

FIG. 36 illustrates the absorption spectra of pure $C_3$ prepared by the Bingel procedure. Purity of the sample was confirmed by HPLC, NMR, and titration, and was >98% pure $C_3$. The maximum (485 nm)/minimum (415 nm) ratio is a measure of purity, with a theoretical ratio of 4.1 for completely pure $C_3$. The sample in FIG. 36 exhibits a ratio of 4.1.

Figure 37:
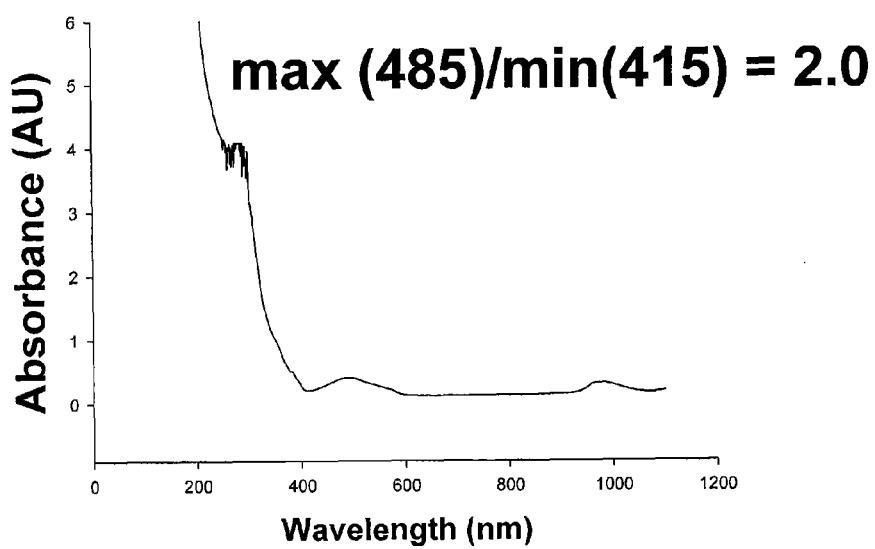
FIG. 37 illustrates absorption spectra of Regis $C_3$ prior to clean-up, as described in detail in Example 2, below.

FIG. 37 illustrates absorption spectra of Regis $C_3$ prior to clean-up. Prior to clean-up, J-Star showed similar spectrum.

Figure 38A:
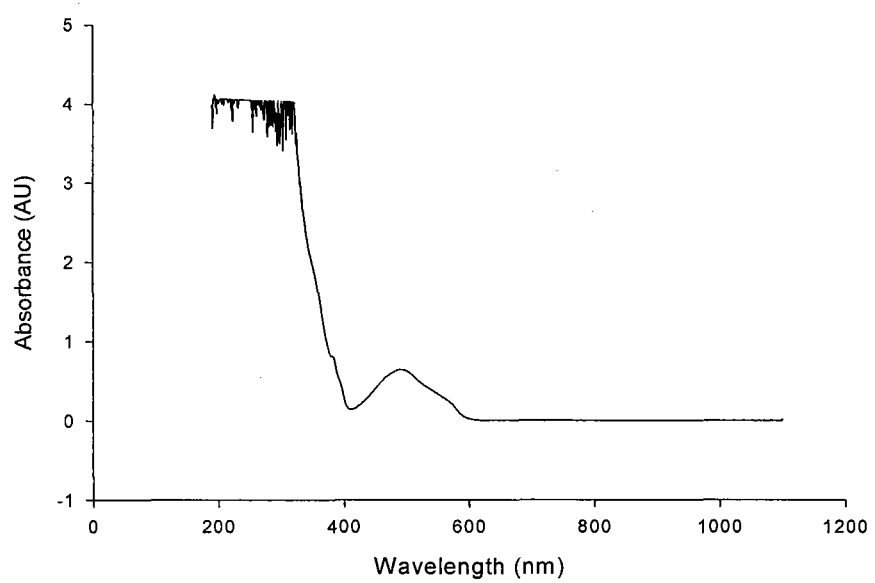
FIG. 38A and FIG. 38B illustrates absorption spectrum of $C_3$ (Regis) after purification using the exemplary protocol (method) of this invention at 2 dilutions to allow all wavelengths of the spectrum to be viewed on scale, as described in detail in Example 2, below.
Figure 38B:
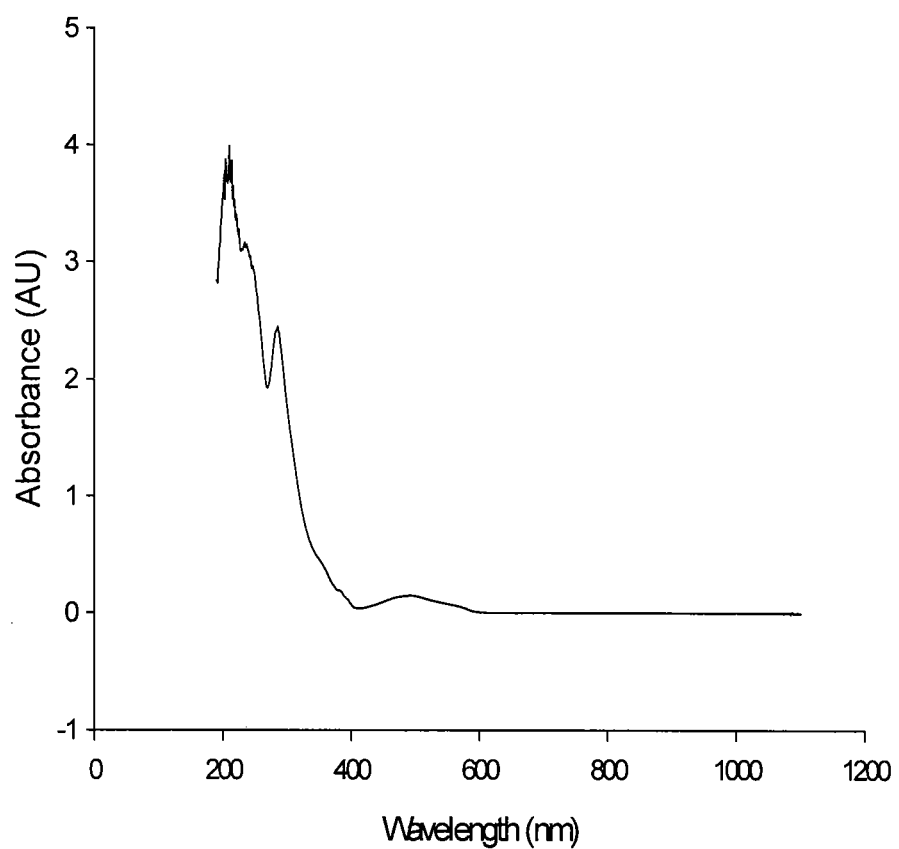

FIG. 38A and FIG. 38B illustrates absorption spectrum of $C_3$ (Regis) after purification using the exemplary protocol (method) of this invention at 2 dilutions to allow all wavelengths of the spectrum to be viewed on scale. After clean-up, the max/min was 4.1

Figure 39A:
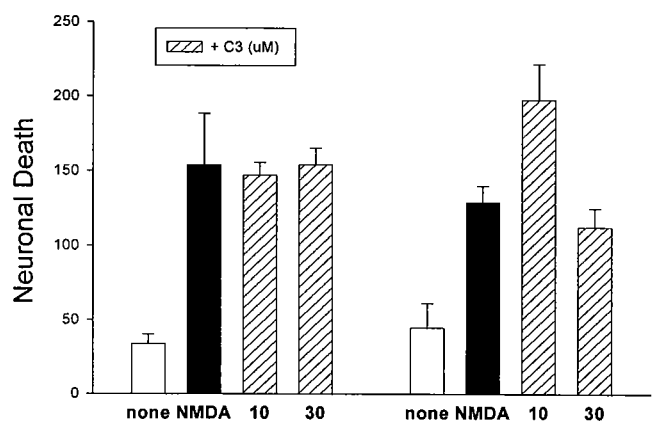
FIG. 39A and FIG. 39B illustrate data demonstrating neuroprotection against NMDA toxicity by a lot of pure $C_3$ using the exemplary purification protocol of this invention, as described in detail in Example 2, below.
Figure 39B:
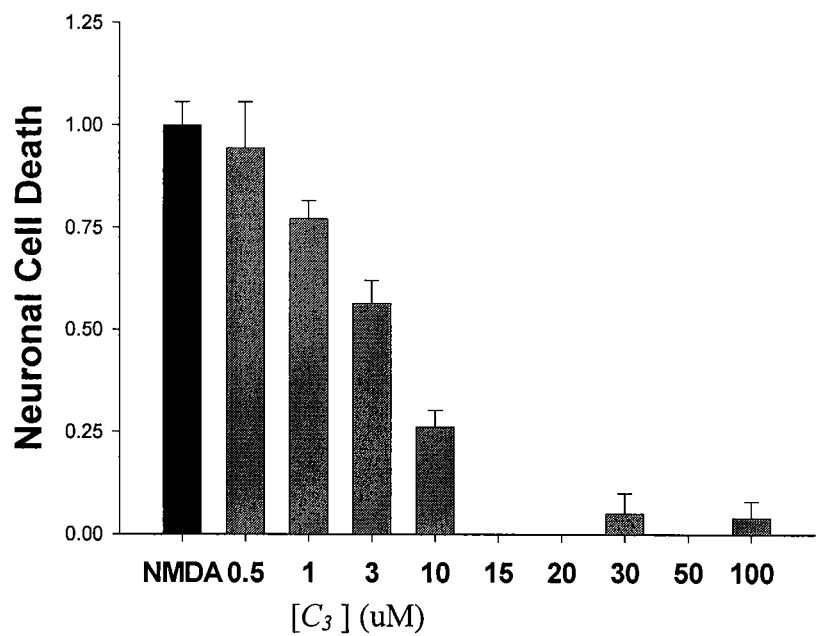

FIG. 39A and FIG. 39B illustrate neuroprotection against NMDA toxicity by a lot of pure $C_3$ using the exemplary purification protocol of this invention. Neuronal cell cultures were exposed to NMDA (150 uM) for 10 minutes in the presence of different concentrations of $C_3$ and the amount of neuronal death assays by lactate dehydrogenase (LDH) release from dying cells.

Contaminated $C_3$ shows direct toxicity on neuronal cell cultures: Regis $C_3$ was applied directly to neuronal cultures at the indicated concentrations, and cell death assayed by LDH release. Cell death was increased at concentrations of contaminated $C_3$ above 3 μM. Pure C3 is not toxic below 300 μM.

Example 3

Compositions and Methods Effective in the Amelioration of Inflammation and/or Oxidative Stress in the CNS Caused or Mediated by IL-6 and NADPH Oxidase This example demonstrates that the compositions and methods of the invention are effective to ameliorate, treat or prevent inflammation and/or oxidative stress in the CNS, e.g., brain. In alternative embodiments, compositions and methods of the invention are used to ameliorate (including to slow, reverse or abate) or prevent the increasing vulnerability to CNS neurodegenerative disorders related to pathologies, diseases (including infections) and conditions associated with an increased amount of CNS inflammation and/or CNS oxidative stress, including Alzheimer's disease, Lewy Body Disease, Parkinson's Disease, Huntington's Disease, Multi-infarct dementia (vascular dementia), senile dementia, Frontotemporal Dementia (Pick's Disease) and related conditions.

These studies demonstrate that inflammation in the CNS (e.g., brain), acting through NADPH oxidase, constitutes a novel target for treatments to ameliorate, halt or reverse pathology in any individual having any CNS neurodegenerative disorder, disease, infection, injury or conditions associated with an increased amount of CNS inflammation and/or CNS oxidative stress.

We tested the possibility of an increased expression of some isoforms of the enzyme in the aged brain. We have analyzed the presence and expression of isoforms of Nox and tested whether Nox activity contributes to superoxide levels in the aged brain. The mRNAs for Nox2, Nox4, and $p22^{phox}$ were increased in several brain regions of aged mice, as illustrated in FIG. 31a), and Western blot analysis of forebrain proteins demonstrated an increase in Nox2, Nox4 and p22 protein content, as illustrated in FIG. 31B. The specificity of the antibodies used for Nox2 was confirmed in gp91phox−/− forebrain extracts, as illustrated in FIG. 31C.

Figure 31:
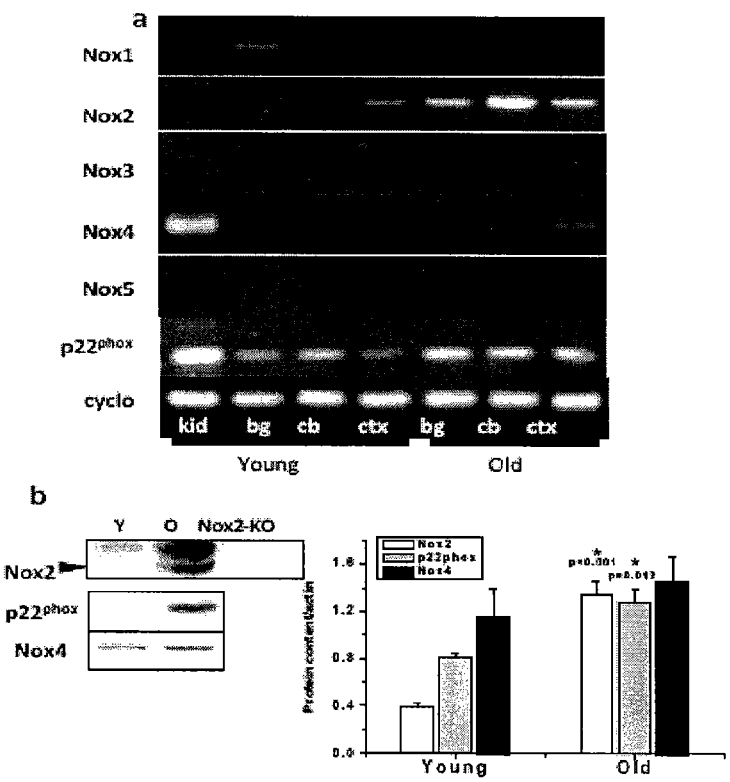
FIG. 31 illustrates data analyzing the presence and expression of isoforms of Nox and tested whether Nox activity contributes to superoxide levels in the aged brain.

FIG. 31 illustrates data showing the expression of Nox(s) in brain in young (4 mo) and old (24 mo) mice. FIG. 31A: RT-PCR depicting mRNA expression of Nox2, Nox4 and required subunits is induced in brain of old (24 mo) compared to young (4 mo) C57BL6 mice. Forebrains of young and old (FIG. 31B) or wild type and gp91phox−/− (FIG. 31C) were lysed in super-RIPA buffer and 50 μg proteins were resolved in 10% SDS-PAGE gels. Antigen recognition was assessed by Western blots using anti-gp91phox antibodies (monoclonal 54.1 or BD-Transduction) anti-p47 (Santa Cruz), anti-p22 (monoclonal 44.1) followed by secondary antibodies conjugated to HRP. Detection was performed using chemiluminescence (Pierce).

To further confirm the neuronal expression of Nox isoforms, we analyzed the presence of Nox2 by fluorescence immunohistochemistry in the hippocampal region of young and old animals. The pyramidal layer of CA1 had shown a substantial increase in ROS upon aging, and Nox2 was highly expressed in this region, as illustrated in FIG. 32, in both neurons and astrocytes.

Figure 32A:
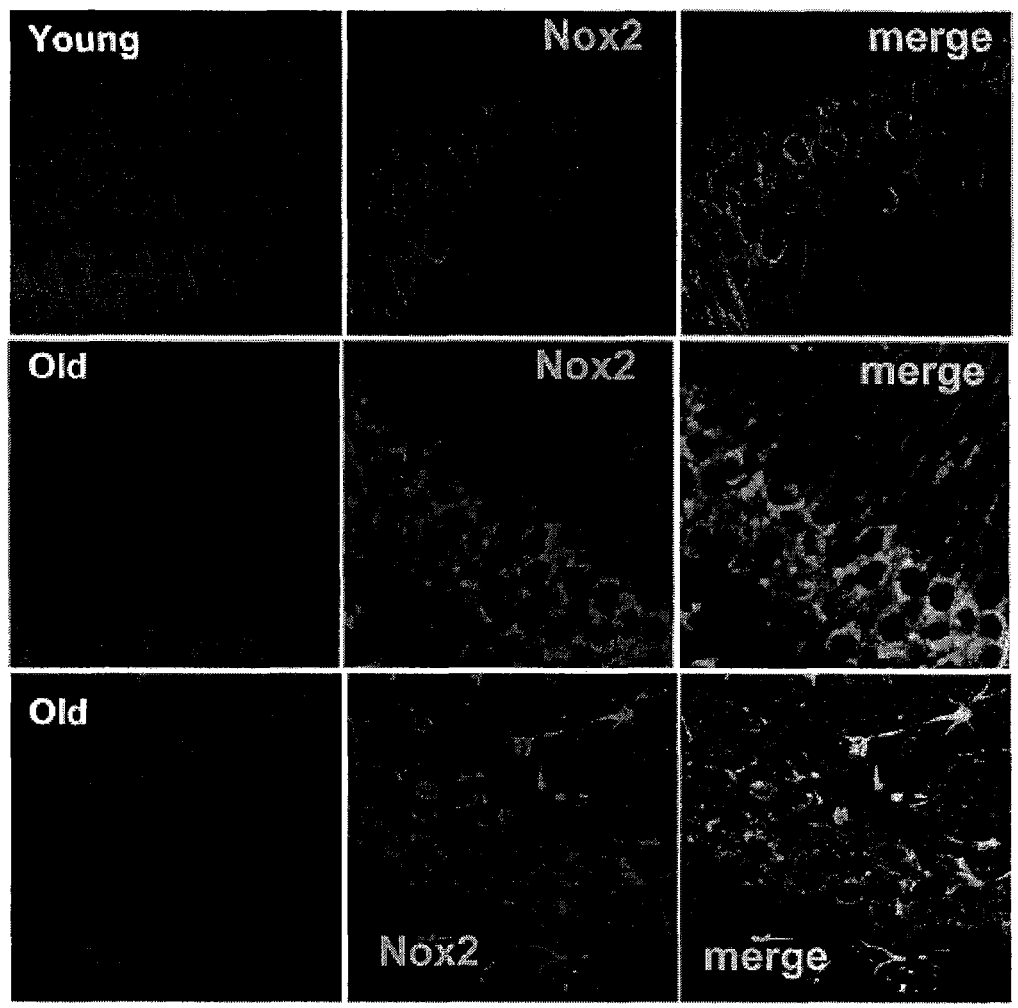
FIG. 32A illustrates nine panels of confocal images of cells showing that aging (old) mice showed increased immunostaining for Nox proteins; immunohistochemistry performed on brain slices from young and old animals revealed increased Nox2; Nox2 expression was increased in neurons and astrocytes in old animals; confocal imaging of the neuronal marker, MAP2 (red), astrocytes marker, GFAP (red), gp91$^{phox}$ (green) and merged images; antibodies were polyclonal anti-MAP2, polyclonal anti-GFAP, and monoclonal 54.1 gp91$^{phox}$.
Figure 32B:
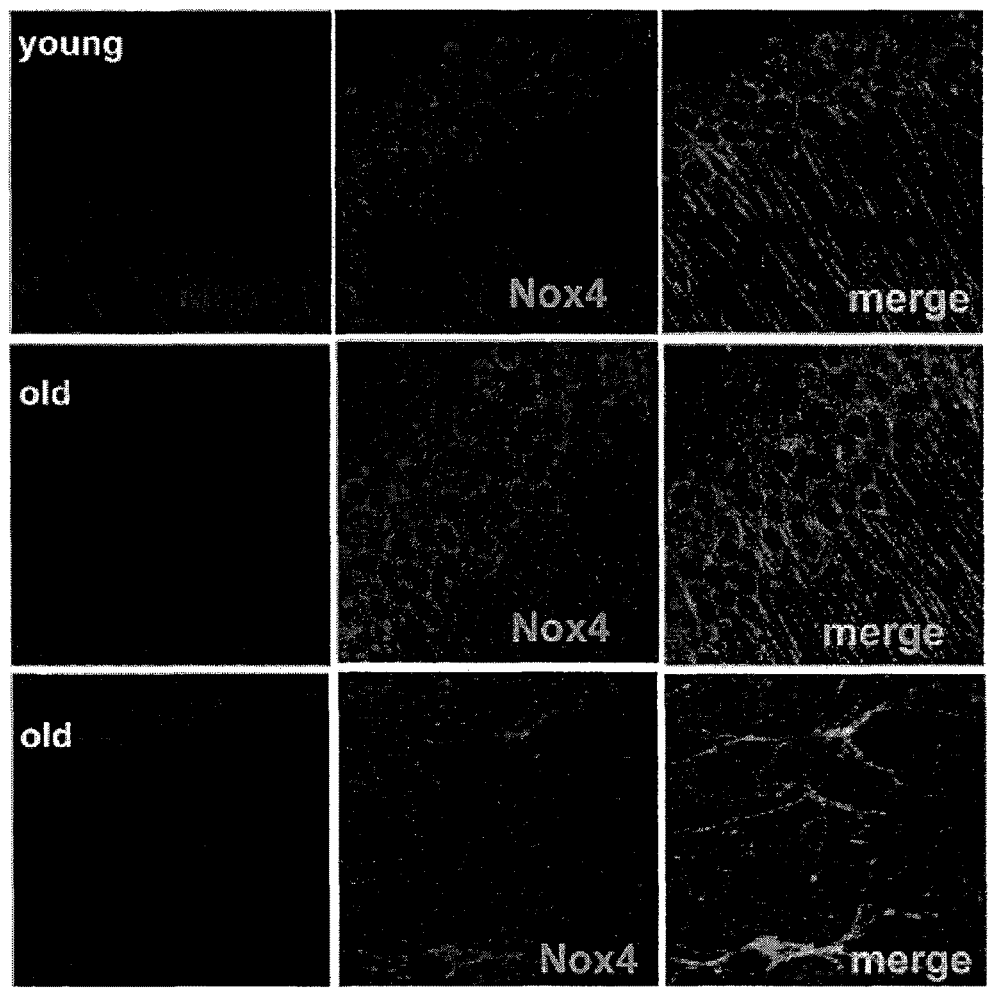
FIG. 32B illustrates nine panels of confocal images of cells showing that aging (old) mice showed increased immunostaining for Nox proteins; immunohistochemistry performed on brain slices from young and old animals revealed increased Nox4; Nox4 expression was increased in neurons and astrocytes in old animals; confocal imaging of the neuronal marker, MAP2 (red), GFAP (red), Nox4 (green) and merged images; antibodies were polyclonal anti-MAP2, polyclonal anti-GFAP, and monoclonal anti-Nox4 antibody, s described in detail in Example 3, below.

FIG. 32 illustrates data showing that aging (old) mice show increased immunostaining for Nox proteins. Immunohistochemistry performed on brain slices from young and old animals revealed increased Nox2. Nox2 expression was increased in neurons and astrocytes in old animals. Confocal imaging of the neuronal marker, MAP2 (red), $gp91^{phox}$ (green) and merged images. Antibodies were polyclonal anti-MAP2 (1:2000 Chemicon), and monoclonal 54.1 $gp91^{phox}$ (1:300).

Figure 33:
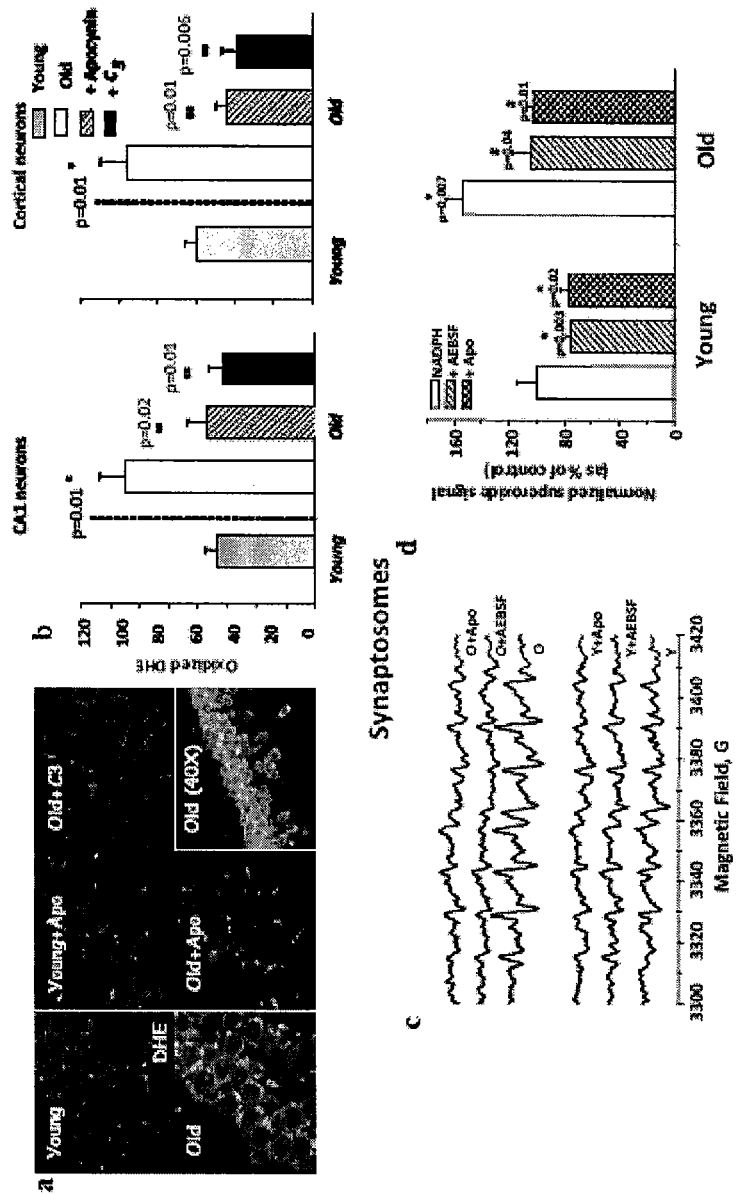
FIG. 33 illustrates four confocal images and graphics showing data of in vivo elevated levels of superoxide production in the pyramidal layer of CA1 in the aged hippocampus, which were prevented by oral administration of the brain-permeable SOD mimetic $C_3$, and by the Nox inhibitor apocynin, which is summarized in the graphic below the confocal images; and including graphic of Nox activity by oximetry with an inset graph showing the relationship of Nox activity and apocynin concentration, and an EPR of superoxide production by Nox.

Confocal imaging of in vivo superoxide production showed elevated levels of superoxide in the pyramidal layer of CA1 in the aged hippocampus, which were prevented by oral administration of the brain-permeable SOD mimetic $C_3$, and by the Nox inhibitor apocynin, as illustrated by the data in FIG. 33. Since the main Nox isoforms expressed in brain are Nox2 and Nox4, and apocynin does not affect Nox4 activity, we concluded that the source of superoxide being induced in the aged brain is Nox2.

Supporting this conclusion, Nox activity was increased in synaptosomes prepared from brains of old mice compared to young animals, as illustrated by the data in FIG. 33C, and was associated with superoxide production as detected by spin-trapping EPR spectroscopy. Nox enzymes are constitutively active in neurons in vivo and in synaptosomes, and it was found that their rate of $O_2$ consumption was equivalent to that of mitochondria, demonstrating that Nox is an important source of superoxide at the synapse and thus contributes to age-dependent deficits in synaptic plasticity.

The mechanisms of induction of Nox in brain are unknown, but studies in phagocytes show that inflammatory mediators are strong inducers of its activity. Since increased inflammatory cytokines have been described in the aged brain, with increased levels of IL-6 being the most consistent finding across species, we decided to study the effects of this interleukin in Nox induction in primary neuronal cultures and in vivo.

Exposure of cortical neurons to IL-6 (20 ng/ml, 1 h in the absence of astrocytes) increased the phosphorylation of the protein kinase Jak2, which transduces the signal from the activated IL-6 receptor, as illustrated by the data shown in FIG. 34A. These results confirm that the interleukin acts directly on neurons. Prolonged exposure (24 h) to the interleukin increased production of superoxide (as determined by DHE oxidation) and increased the expression of Nox2 in neurons, as illustrated by the data shown in FIG. 34B. The role of Nox2 activation in the increase in DHE oxidation was confirmed by co-exposure to the Nox inhibitor apocynin (0.5 mM) (FIG. 34B bottom panels).

Figure 34:
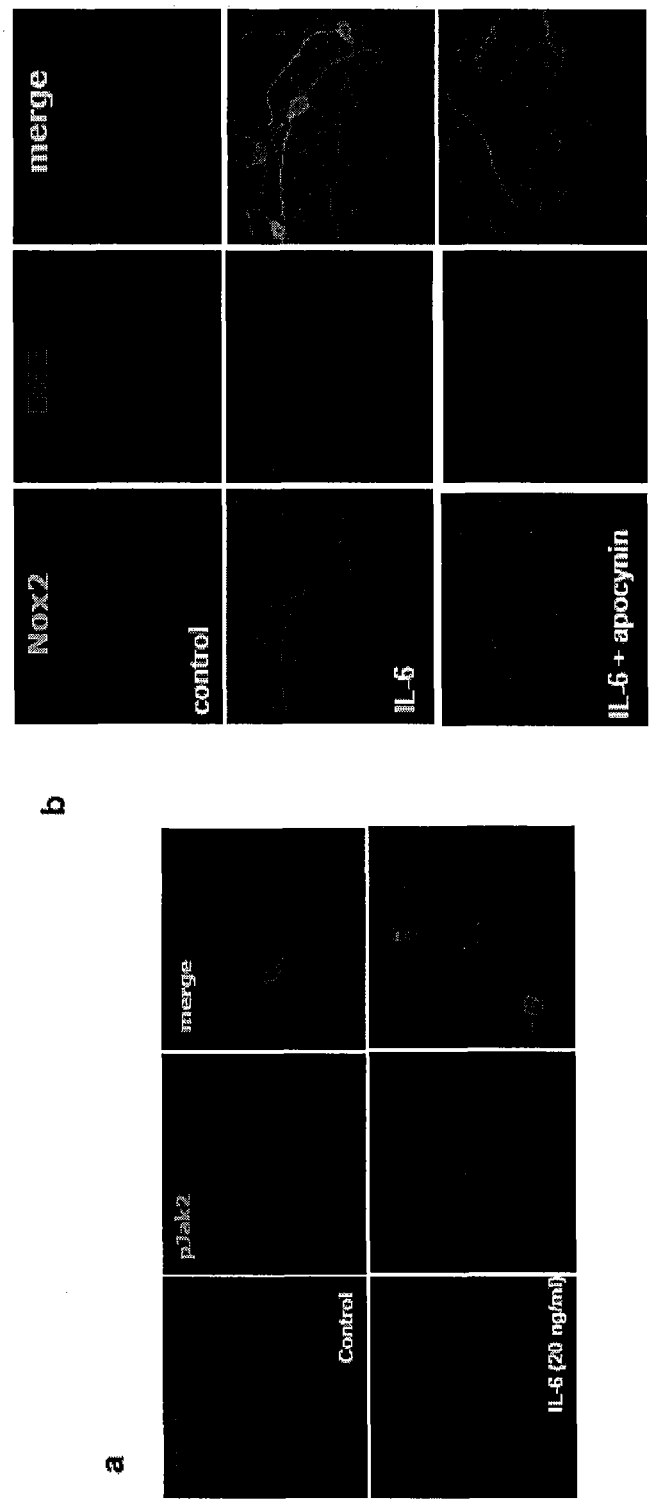
FIG. 34 illustrates confocal images of cortical neurons after exposure to IL-6.

For FIG. 34: primary neuronal cultures were developed on coverslips as described Kinney et al., 2006, supra. After 21 days in culture, coverslips containing neurons were separated from the astrocytic monolayers, washed in HCSS and subjected to IL-6 treatment for 1 hour (FIG. 34A) or treated with IL-6 for 24 h on top of the astrocyte monolayer (FIG. 34B). After treatment, the coverslips were fixed in paraformaldehyde and processed for double fluorescence immuno-cytochemistry using the following antibodies: anti-GAD67 (1:2000, Chemicon. Red) anti-phospho-Jak2 (1:100, Cell Signaling. Green), and anti-Nox2 (1:300, monoclonal 54.1 Green). For detection of ROS, DHE (1 µg/ml. Red) was applied for the last hour of treatment. Images were obtained using a Zeiss confocal microscope with a 40× water immersion objective. Secondary antibodies were conjugated to ALEXAFLUOR 488™ (green fluorescence) and ALEXAFLUOR 568™ (red fluorescence).

Figure 35:
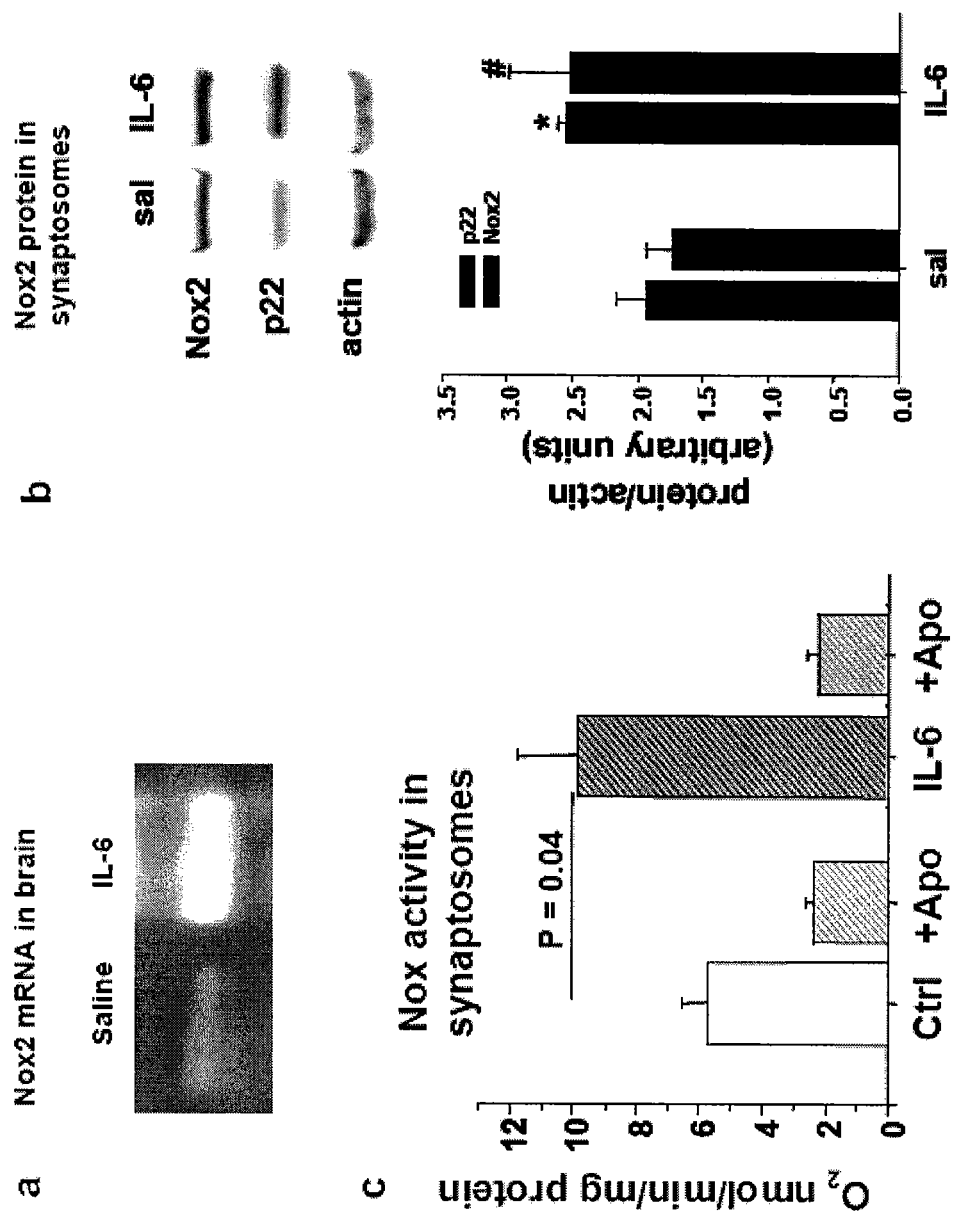
FIGS. 35 A-C illustrates an image and graphics showing data that IL-6 treatment in vivo increases Nox2 mRNA in brain as well as Nox protein and activity in synaptosomes.

FIG. 35 illustrates that IL-6 treatment in vivo increases Nox2 mRNA in brain, as well as Nox protein and activity in synaptosomes. Four month old C57Bl/6 were treated with either saline (saline or control) or with IL-6 (5 µg/kg) on two consecutive days, and brains were either processed for RNA (FIG. 35A) or for synaptosomal preparation (FIG. 35B and FIG. 35C). Nox2 mRNA was detected by RT-PCR as described herein. For detection of Nox2 and p22, antibodies against the corresponding proteins were used on immunoblots of 50 µg of synaptosomal proteins separated on 10% SDS-PAGE gels. Antibodies used were anti-Nox2 (54.1, 1:1000), anti p22 (44.1: 1:500), and anti-actin (1:30,000, Chemicon). Synaptosomal Nox activity was assayed as described above.

Example 4

Compositions and Methods of the Invention are Effective in the Amelioration of Aging and Frailty Syndrome (FS)

This example demonstrates that the compositions and methods of the invention are effective to ameliorate, treat or prevent frailty syndrome (FS), and the CNS neurodegenerative, cognitive, learning or memory impairments resulting therefrom. FS is a recognized condition seen particularly in older patients characterized by, e.g., low functional reserve, easy tiring, decrease of libido, mood disturbance, accelerated osteoporosis, decreased muscle strength, and high susceptibility to disease. This example demonstrates that eliminating IL-6 appears to block features of the frailty syndrome, and that this may be mediated by reducing superoxide levels.

Figure 40:
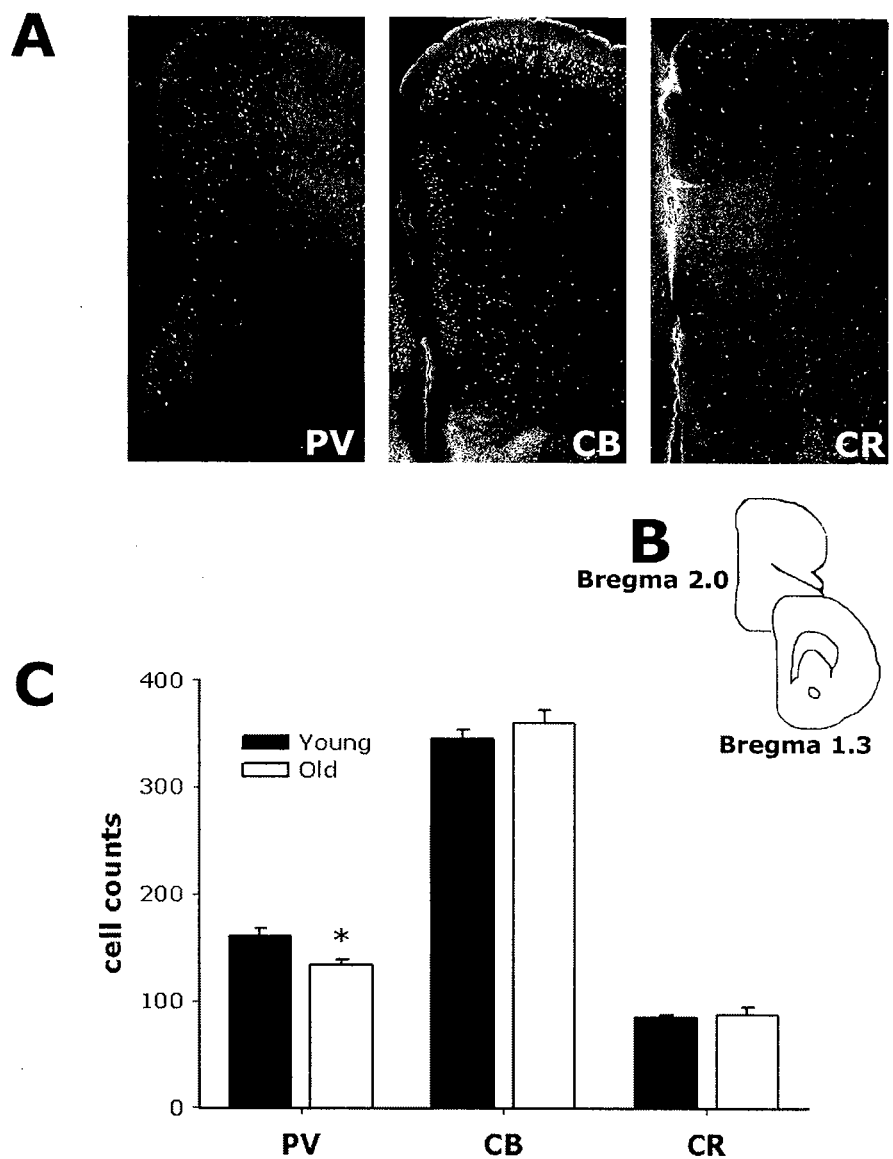
FIG. 40 illustrates data demonstrating age-related reduction in number of parvalbumin-interneurons in the prefrontal cortex: fluorescent staining for markers is shown in FIG. 40A; coronal sections comprising the regions between Bregma 2.0 and 1.3 are as shown in FIG. 40B, and the cumulative results for the expression of each CBP are shown in FIG. 40C, as described in detail in Example 4, below.

Age-related reduction in number of parvalbumin-interneurons in the prefrontal cortex is demonstrated by data shown in FIG. 40. The prefrontal cortex (including the pre-limbic and infra-limbic regions) was analyzed for the expression of the calcium binding proteins (CBP) parvalbumin (PV), calbindin (CB), and calretinin (CR). Fluorescent staining for these markers showed a different distribution for each CBP, as shown in FIG. 40A. Analysis of the number of cells expressing each CBP was performed across 6 consecutive coronal sections comprising the regions between Bregma 2.0 and 1.3, as shown in FIG. 40B, and the cumulative results for the expression of each CBP are shown in FIG. 40C. *=statistically significant ($P<0.001$) with respect to young by one-way ANOVA followed by Tukey's test. N=6 animals per condition.

Figure 41:
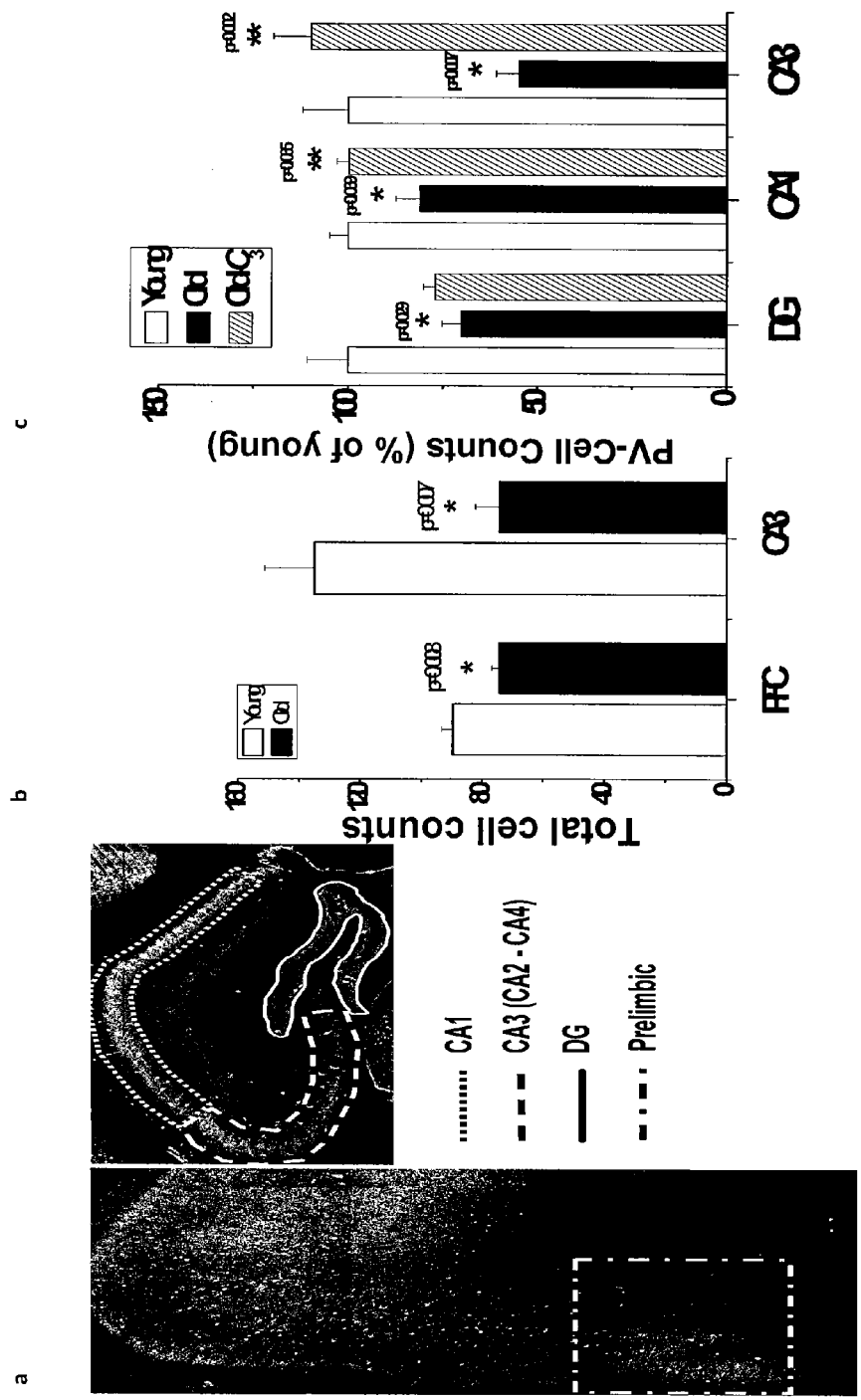
FIG. 41 illustrates data demonstrating age-related decrease of PV-interneurons in prefrontal and hippocampal regions: long-term chronic treatment with an SOD-mimetic prevents interneuron loss: coronal brain slices of young (YM) and old (OM) male mice were stained for parvalbumin and total PV-positive cell counts were evaluated across 4 slices of the prelimbic region (PFC) and hippocampal regions CA1, CA3 and dentate gyrus (DG), as shown in FIG. 41A; aging was accompanied by a statistically significant decrease in PV-interneuron number in all regions analyzed, as shown in FIG. 41B; treatment of animals from middle age with the SOD-mimetic C3 (OM+C3) prevented the reduction of PV-interneuron numbers in CA1 and CA3, but not in DG, as shown in FIG. 41C, as described in detail in Example 4, below.

Age-related decrease of PV-interneurons in prefrontal and hippocampal regions: long-term chronic treatment with an SOD-mimetic prevents interneuron loss is demonstrated by data shown in FIG. 41. Coronal brain slices of young (YM) and old (OM) male mice were stained for parvalbumin and total PV-positive cell counts were evaluated across 4 slices of the prelimbic region (PFC) and hippocampal regions CA1, CA3 and dentate gyrus (DG), as shown in FIG. 41A, and as described in detail in Example 3, above. Aging was accompanied by a statistically significant decrease in PV-interneuron number in all regions analyzed, as shown in FIG. 41B. A reduction of 17.1±6.8% ($p=0.008$) was observed in PFC, and of 45.1±17.7% in area CA3 ($p=0.002$), which was the most pronounced decrease of all regions analyzed. Treatment of animals from middle age with the SOD-mimetic C3 (OM+C3) prevented the reduction of PV-interneuron numbers in CA1 and CA3, but not in DG, as shown in FIG. 41C. Statistical significance was determined by ANOVA followed by Tukey's test. YM and OM: n=9 animals per group; OM+C3: n=7 animals.

Figure 42:
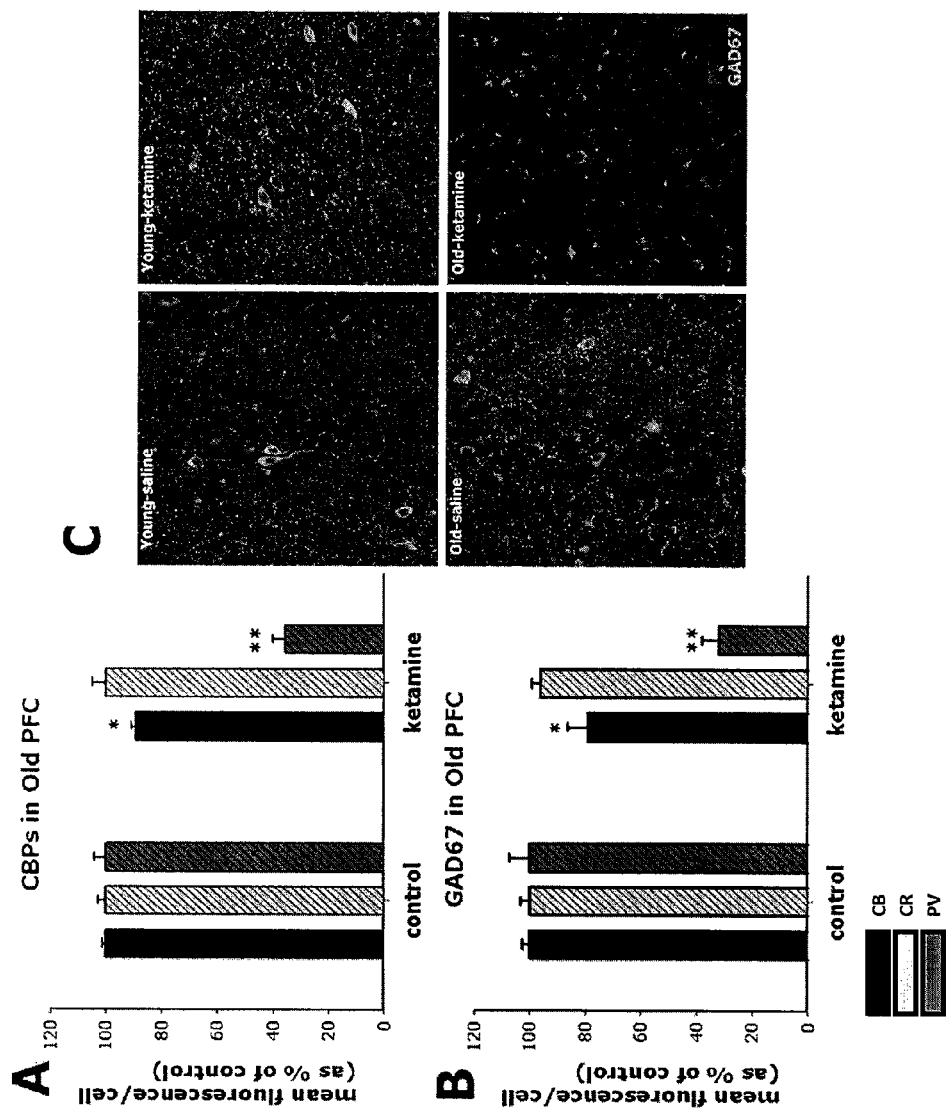
FIG. 42 illustrates data demonstrating that the aged prefrontal cortex is more vulnerable to the effects of ketamine on parvalbumin and calbindin interneurons: brain coronal sections from animals treated with saline or ketamine were double stained for each CBP and GAD67.

The aged prefrontal cortex is more vulnerable to the effects of ketamine on parvalbumin and calbindin interneurons, as demonstrated by data shown in FIG. 42. Brain coronal sections (50 mm) from animals (young and old) treated with saline or ketamine (15 mg/kg, i.p.) were double stained for each CBP and GAD67. The median fluorescence intensity per cell was obtained for each section and averaged across all sections of the animal to obtain the mean intensity per cell across the PFC of each animal. Results obtained for all animals were normalized by the average mean intensity per cell obtained for the saline treated controls and expressed as percentages of control conditions. FIG. 42A: Effect of ketamine on the average mean intensity per cell for each CBP in the PFC region. FIG. 42B: Analysis of the mean intensity per cell for GAD67 content analyzed in each CBP stained cell. FIG. 42C: Confocal images obtained with a 40× objective depicting the effects of ketamine on the immunofluorescence for PV and GAD67 in the PFC region of young and old animals (Bar=20 mm). *=statistically significant with respect to saline control (CB: $P<0.001$; GAD67 in CB cells: $P=0.024$; PV: $P<0.001$; GAD67 in PV cells: $P=0.003$) by ANOVA followed by Tukey's test.

Figure 43:
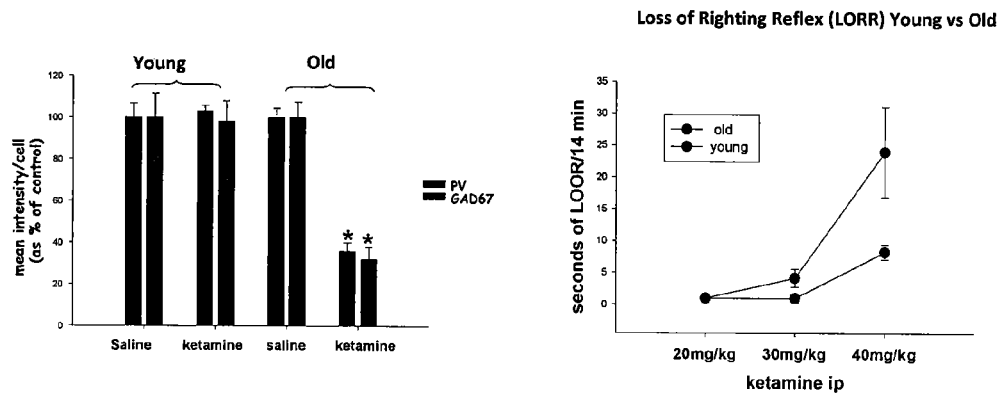
FIG. 43 illustrates data demonstrating that aging increases the vulnerability to Nox-dependent loss of phenotype of PV-interneurons and sensitivity to low doses of an anesthetic ketamine.

Aging increases the vulnerability to Nox-dependent loss of phenotype of PV-interneurons and sensitivity to low doses of an anesthetic (ketamine), as illustrated by data shown in FIG. 43. As shown in FIG. 43A, in addition to loss of PV-interneurons with aging, there is enhanced vulnerability of the remaining neurons to loss-of-phenotype (and loss of inhibitory function) in old mice in response to even sub-anesthetic doses of an anesthetic, in this case, ketamine (15 mg/kg i.p. on two consecutive days). Aging also increases the sensitivity to ketamine, demonstrated using a "loss of righting reflex (LORR) test, as shown in FIG. 43B, with significantly greater loss-of-righting reflex in old (versus young) animals at the same dose of ketamine.

Figure 44:
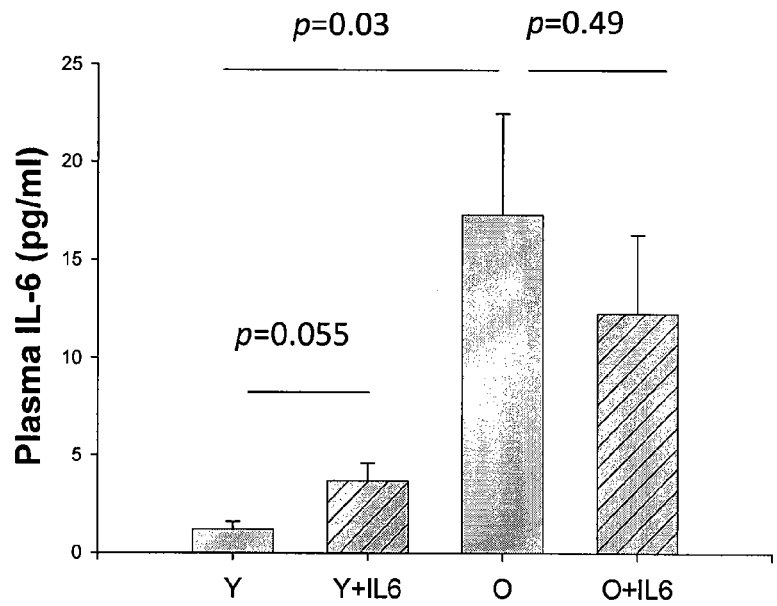
FIG. 44 illustrates data demonstrating that plasma IL-6 is increased with aging or after intraperitoneal (i.p.) administration of IL-6, IL-6 was assayed by ELISA, mice were then given a direct intraperitoneal (IP) injection IL-6 on two consecutive days, and plasma IL-6 was assayed 16 hours (hr) after the last injection, as described in detail in Example 4, below.

Plasma IL-6 is increased with aging or after intraperitoneal (i.p.) administration of IL-6, as illustrated by data shown in FIG. 44. Plasma levels of IL-6 are significantly increased in 24-month old C57B6 mice versus young (4 month) mice. IL-6 was assayed by ELISA (R&D Systems, Minneapolis, Minn.). Mice were then given a direct intraperitoneal (IP) injection of 3 µg/kg IL-6 on two consecutive days, and plasma IL-6 was assayed 16 hours (hr) after the last injection. IL-6 injection increased plasma IL-6 in young, but not old, mice. Since the half-life of IL-6 in plasma is 4 hr, the sustained increase in IL-6 after injection may indicate induction of new IL-6 synthesis in young mice, which may be suppressed by the high endogenous IL-6 levels in old mice. Higher doses of IL-6 (12 µg/kg) induced the sickness response and generalized inflammatory reaction, so 3 µg/kg/day for two consecutive days was used for all subsequent studies.

Figure 45:
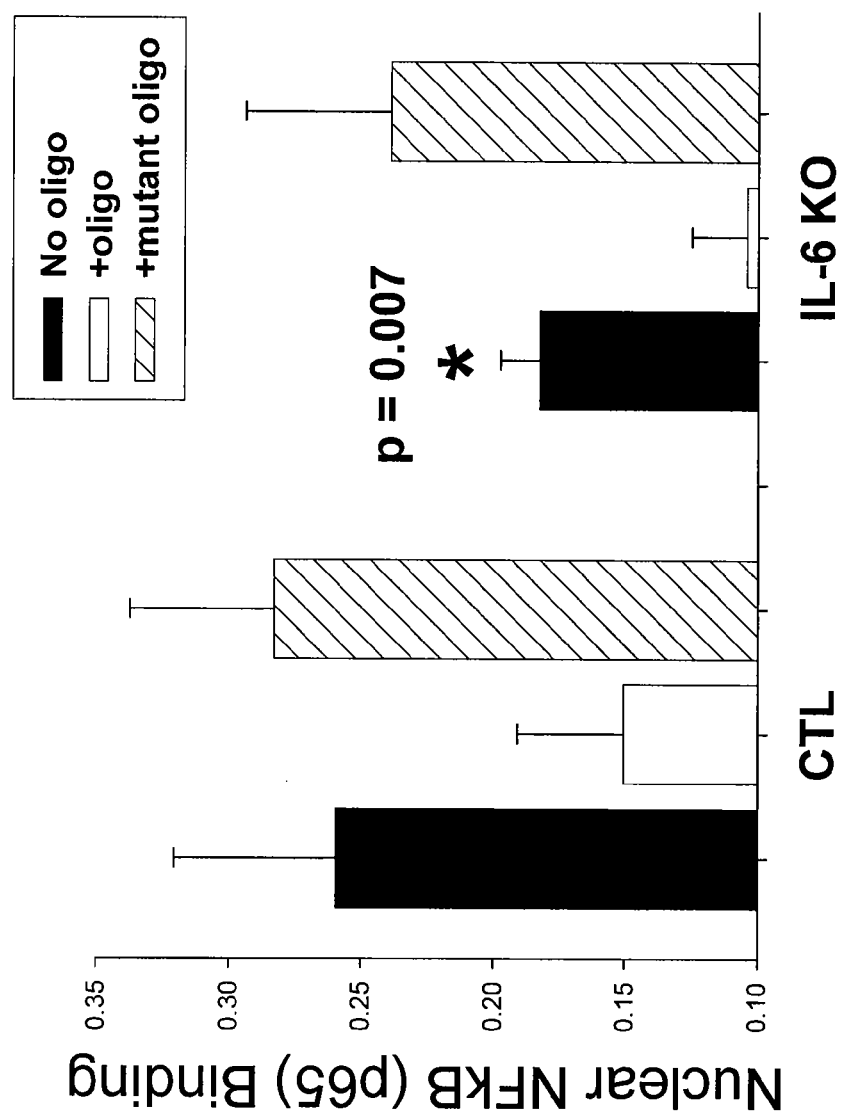
FIG. 45 illustrates data demonstrating that NFkB (p65) activity as measured in brain nuclear extracts from old wild-type (WT) ("CTL", or control) versus old IL-6–/– mice ("IL-6 KO", or IL-6 knockout) by an ELISA kit for the p65 subunit of NFkB, with "no oligo" and "mutant oligo" controls, as described in detail in Example 4, below.

NFkB (p65) activity was measured in brain nuclear extracts from old wild-type (WT) ("CTL", or control) versus old IL-6−/− mice ("IL-6 KO", or IL-6 knockout) by an ELISA kit for the p65 subunit of NFkB, with "no oligo" and "mutant oligo" controls, as illustrated by data shown in FIG. 45. Old IL-6−/− mice have significantly lower NFkB activity than old WT mice. Since NFkB regulates expression of Nox subunits including Nox2, p22phox and p47phox, among others, decreased NFkB activity in IL-6−/− mice would reduce expression of Nox isoforms in aging, as observed.

Figure 46:
FIG. 46 illustrates data demonstrating that RNA expression of IL-1β and TNFα was measured in brain extracts from old wild-type and old IL-6–/– mice, indicating that lack of IL-6 expression in the IL-6–/– mice does not modify expression of IL-1β or TNFα, as described in detail in Example 4, below.

RNA expression of IL-1b and TNFα was measured in brain extracts from old wild-type and old IL-6−/− mice (as in FIG. 45), as illustrated by data shown in FIG. 46, indicating that lack of IL-6 expression in the IL-6−/− mice does not modify expression of IL-1β or TNFα. Lane with X did not have RNA loaded. GAPDH RNA expression serves as internal control.

Figure 47:
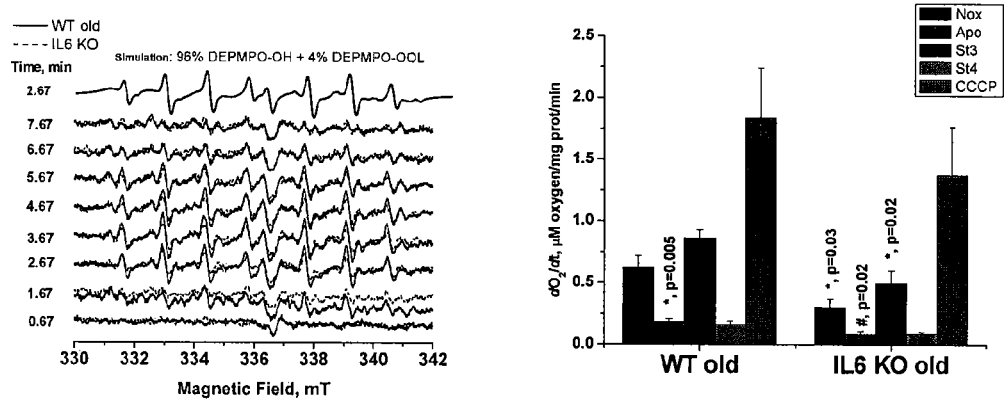
FIG. 47 illustrates data demonstrating that Nox-dependent superoxide production is lower in synaptosomes from IL-6-KO old mice compared to age-matched wild-type controls, as measured by EPR, with spectra illustrated in FIG. 47, left, as graphically illustrated in FIG. 47, right, as described in detail in Example 4, below.

Nox-dependent superoxide production is lower in synaptosomes from IL-6 deficient (IL-6-KO) old mice compared to age-matched (old) wild-type controls, as measured by EPR, with spectra illustrated in FIG. 47, left, as graphically illustrated in FIG. 47, right; demonstrating that IL-6 increases Nox-dependent superoxide production.

Figure 48:
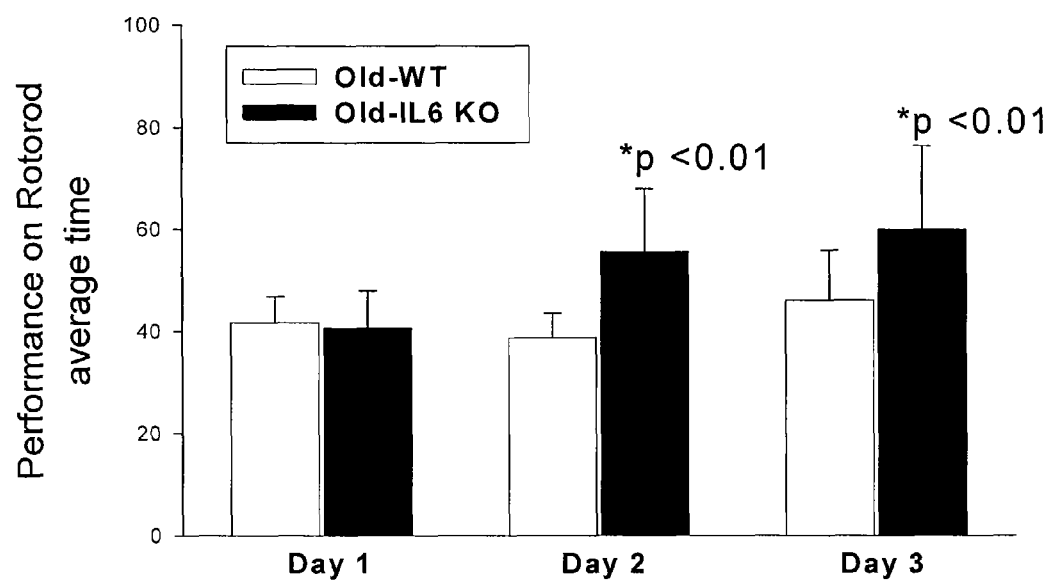
FIG. 48 illustrates data demonstrating that performance of IL-6 deficient old mice compared to age-matched (old) wild-type controls on a rotorod test showed that in day 2 and day 3 test samples the presence of IL-6 decreased the level of performance, as described in detail in Example 4, below.

Performance of IL-6 deficient (IL-6-KO) old mice compared to age-matched (old) wild-type controls on a rotorod test showed that in day 2 and day 3 test samples the presence of IL-6 decreased the level of performance, as illustrated by data shown in FIG. 48. The rotorod is designed to assess motor coordination, balance and equilibrium. The mouse can be placed on a rod and the rotorod accelerates gradually. Latencies for the mice to fall from the rod are recorded. A rotorod can be a semi-enclosed chamber which contains a beam made of ribbed plastic and flanked by round plates on either side to prevent any escape (e.g., Accuscan Instruments, Columbus, Ohio). The rod can be suspended at a height (e.g., 35 cm) above the floor. The mouse is placed on top of the beam facing away from the experimenter's view, in the orientation opposite to that of its rotation, so that forward locomotion is necessary for fall avoidance. The rotorod can be accelerated gradually without jerks from 0 to 35 rpm over a 2-minute trial. Latencies for the mice to fall from the rod can be recorded automatically by a computer. Each mouse can be given 2 to 5 trials with a 15-min inter-trial interval on each of 3 consecutive days.

IL-6 knockout (IL-6−/−) male mice retain reproductive fecundity into late-life compared as to wild-type controls; thus, the presence of IL-6 decreases fecundity in late-life. The number of litters and pups fathered was recorded for 4 IL-6−/− mice versus more than 10 control males. Six of the litters were fathered by IL-6−/− mice older than 20 months of age. No litters were fathered by WT mice past 14 mos of age.

| Genotype (C57BL6 background) | Gender | n | # of litters fathered after 14 mo of age | # of pups |
|---|---|---|---|---|
| WT | M | >10 | 0 | 0 |
| IL-6(−/−) | M | 4 | 13 | 70 |

Oldest father 24 mos+

A number of embodiments of the invention have been described. Nevertheless, it will be understood that various modifications may be made without departing from the spirit and scope of the invention. Accordingly, other embodiments are within the scope of the following claims.

What is claimed is:

1. A method for ameliorating, treating or preventing a central nervous system (CNS) inflammation in an individual,
   wherein the central nervous system (CNS) inflammation is due to a trauma, comprising:
   (a) (i) providing a pharmaceutically active agent consisting of a therapeutic monoclonal antibody that specifically binds an interleukin-6 receptor (IL-6-R) and blocks or inhibits IL-6-R binding with its ligand,
   wherein the therapeutic monoclonal antibody against the IL-6-R consists of a tocilizumab, and
   (ii) administering an effective amount of the pharmaceutically active agent to the individual in need thereof, thereby ameliorating, reversing, treating or preventing the trauma-induced central nervous system (CNS) inflammation in the individual; or (b) the method of (a), wherein the pharmaceutically active agent is formulated with a pharmaceutically acceptable excipient.

2. The method of claim 1, wherein the individual is a human.

3. The method of claim 1, wherein the pharmaceutically active agent comprises a pharmaceutical formulation.

4. The method of claim 3, wherein the pharmaceutical formulation is formulated for delivery to the brain or a neural cell, or for passing through the blood brain barrier (BBB).

5. The method of claim 3, wherein the pharmaceutical formulation is formulated for delivery across the blood brain barrier (BBB).

6. The method of claim 1, wherein the therapeutic monoclonal antibody is a humanized or a human antibody.

7. The method of claim 1, wherein the method ameliorates the trauma-induced central nervous system (CNS) inflammation in the individual.

8. The method of claim 1, wherein the method prevents the trauma-induced central nervous system (CNS) inflammation in the individual.

9. A method for ameliorating, treating or preventing a trauma-caused central nervous system (CNS) inflammation in an individual consisting of:

(a) administering an effective amount of a tocilizumab to the individual in need thereof, thereby ameliorating, reversing, treating or preventing the trauma-caused central nervous system (CNS) inflammation in the individual; or (b) the method of (a), wherein the tocilizumab is formulated with a pharmaceutically acceptable excipient.

10. The method of claim 9, wherein the tocilizumab is formulated as a pharmaceutical formulation.

11. The method of claim 10, wherein the pharmaceutical formulation is formulated for delivery to the brain or a neural cell, or for passing through the blood brain barrier (BBB).

12. The method of claim 10, wherein the pharmaceutical formulation is formulated for delivery across the blood brain barrier (BBB).

13. The method of claim 9, wherein the method ameliorates the trauma-induced central nervous system (CNS) inflammation in the individual.

14. The method of claim 9, wherein the method reverses the trauma-induced central nervous system (CNS) inflammation in the individual.

15. A method for ameliorating, reversing or treating a trauma-caused central nervous system (CNS) inflammation in an individual, wherein the method consists of:

(a) administering to the individual in need thereof an effective amount of a composition having only one active agent consisting of a tocilizumab, thereby ameliorating, reversing or treating the trauma-caused central nervous system (CNS) inflammation in the individual; or (b) the method of (a), wherein the tocilizumab is formulated with a pharmaceutically acceptable excipient.

16. The method of claim 5, wherein the tocilizumab is formulated as a pharmaceutical formulation.

17. The method of claim 16, wherein the pharmaceutical formulation is formulated for delivery to the brain or a neural cell, or for passing through the blood brain barrier (BBB).

18. The method of claim 16, wherein the pharmaceutical formulation is formulated for delivery across the blood brain barrier (BBB).

19. The method of claim 15, wherein the method ameliorates the trauma-induced central nervous system (CNS) inflammation in the individual.

20. The method of claim 15, wherein the method reverses the trauma-induced central nervous system (CNS) inflammation in the individual.

* * * * *

SEQUENCE LISTING

```
<160> NUMBER OF SEQ ID NOS: 1

<210> SEQ ID NO 1
<211> LENGTH: 26
<212> TYPE: PRT
<213> ORGANISM: artificial sequence
<220> FEATURE:
<223> OTHER INFORMATION: artificial peptide

<400> SEQUENCE: 1

Ala Ala Val Ala Leu Leu Pro Ala Val Leu Leu Ala Leu Leu Ala Pro
1               5                   10                  15

Val Gln Arg Lys Arg Gln Lys Leu Met Pro
            20                  25
```